US010709758B2

(12) United States Patent
Ballard et al.

(10) Patent No.: US 10,709,758 B2
(45) Date of Patent: Jul. 14, 2020

(54) PEPTIDE INHIBITORS OF CLOSTRIDIUM DIFFICILE TOXIN B (TCDB) TOXIN

(71) Applicant: The Board of Regents of the University of Oklahoma, Norman, OK (US)

(72) Inventors: Jimmy D. Ballard, Norman, OK (US); Jason L. Larabee, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 15/756,483

(22) PCT Filed: Sep. 2, 2016

(86) PCT No.: PCT/US2016/050038
§ 371 (c)(1),
(2) Date: Feb. 28, 2018

(87) PCT Pub. No.: WO2017/040885
PCT Pub. Date: Mar. 9, 2017

(65) Prior Publication Data
US 2018/0243365 A1   Aug. 30, 2018

Related U.S. Application Data

(60) Provisional application No. 62/214,082, filed on Sep. 3, 2015.

(51) Int. Cl.
| *A61K 38/10* | (2006.01) |
| *A61K 38/16* | (2006.01) |
| *A61K 38/00* | (2006.01) |
| *A61K 39/40* | (2006.01) |
| *C07K 14/33* | (2006.01) |
| *C07K 7/08* | (2006.01) |
| *C07K 7/00* | (2006.01) |
| *A61P 31/04* | (2006.01) |

(52) U.S. Cl.
CPC ............ *A61K 38/164* (2013.01); *A61K 38/10* (2013.01); *A61K 39/40* (2013.01); *A61P 31/04* (2018.01); *C07K 14/33* (2013.01)

(58) Field of Classification Search
CPC ...... A61K 38/10; A61K 38/16; A61K 38/164; A61K 38/00; A61K 39/40; C07K 14/33; C07K 14/00; C07K 7/08; C07K 7/00; A61P 31/04
USPC ....... 514/21.4, 21.3, 21.2, 1.1, 1.2; 530/300, 530/324, 325, 326
See application file for complete search history.

(56) References Cited

U.S. PATENT DOCUMENTS

| 4,673,574 | A | 6/1987 | Anderson |
| 5,057,540 | A | 10/1991 | Kensil et al. |
| 5,936,076 | A | 8/1999 | Higa et al. |
| 6,531,453 | B1 | 3/2003 | Taniguchi et al. |
| 7,402,572 | B2 | 7/2008 | Krieg et al. |
| 8,334,408 | B2 | 12/2012 | Cerundolo et al. |
| 8,431,361 | B2 * | 4/2013 | Ballard ................ C12N 15/70 435/252.3 |
| 8,895,514 | B2 | 11/2014 | Weinschenk et al. |
| 8,906,635 | B2 | 12/2014 | Jin et al. |
| 9,926,345 | B2 | 3/2018 | Melnyk et al. |
| 9,957,305 | B2 | 5/2018 | Ballard et al. |
| 2003/0054493 | A1 | 3/2003 | Williams et al. |
| 2003/0157135 | A1 | 8/2003 | Tsuji et al. |
| 2004/0242499 | A1 | 12/2004 | Uematsu et al. |
| 2007/0231336 | A1 | 10/2007 | Thomas, Jr. et al. |
| 2007/0269861 | A1 | 11/2007 | Williams et al. |
| 2009/0087478 | A1 | 4/2009 | Hansen et al. |
| 2010/0278868 | A1 | 11/2010 | Gardiner et al. |
| 2012/0070859 | A1 | 3/2012 | Ballard et al. |
| 2012/0269857 | A1 | 10/2012 | Cerundolo et al. |
| 2012/0282274 | A1 | 11/2012 | Jin et al. |
| 2013/0072881 | A1 | 3/2013 | Khandke et al. |
| 2013/0209503 | A1 | 8/2013 | Kapre et al. |
| 2013/0266583 | A1 | 10/2013 | Shone et al. |
| 2013/0330335 | A1 | 12/2013 | Bremel et al. |
| 2013/0337006 | A1 | 12/2013 | Garcon et al. |
| 2014/0234360 | A1 | 8/2014 | Kubler-Kielb et al. |
| 2015/0284814 | A1 * | 10/2015 | Barouch ................ C12Q 1/703 435/5 |
| 2015/0344861 | A1 * | 12/2015 | Kumar ............... C07K 14/3153 424/94.67 |

FOREIGN PATENT DOCUMENTS

| GB | 2220211 | A | 4/1990 |
| WO | 2004041857 | A2 | 5/2004 |
| WO | 2010094970 | A1 | 8/2010 |
| WO | 2011130650 | A2 | 10/2011 |
| WO | 2013038156 | A1 | 3/2013 |
| WO | 2013040254 | A2 | 3/2013 |
| WO | 2014176276 | A1 | 10/2014 |
| WO | 2015085318 | A1 | 6/2015 |
| WO | 2015085318 | A2 | 6/2015 |
| WO | 2017040885 | A1 | 3/2017 |

OTHER PUBLICATIONS

PCT/US2016/050038; "International Search Report and Written Opinion"; dated Jan. 24, 2017; 19 pages.

(Continued)

*Primary Examiner* — Julie Ha
(74) *Attorney, Agent, or Firm* — Hall Estill Law Firm

(57) ABSTRACT

Disclosed are synthetic peptides and peptide compositions, including peptide conjugates, that can ameliorate and/or block the cytotoxicity of *Clostridium difficile* toxin B(TcdB), and methods of their use for inhibiting the activity of *Clostridium difficile* toxin B(TcdB) and protecting against damage during *Clostridium difficile* toxin B(TcdB) disease, and/or for use as cell penetrating peptides for enhancing the delivery of particular heterogenous molecules into cells.

21 Claims, 32 Drawing Sheets

Specification includes a Sequence Listing.

(56) References Cited

OTHER PUBLICATIONS

Kiessling, R., et al.; "'Natural' killer cells in the mouse"; Eur. J. Immunol. 5 (1975) 112-117.
Kohler, G., et al.; "Pillars Article: Continuous cultures of fused cells secreting antibody of predefined specificity"; Nature 256:5517 (1975) 495-497.
Pearson, W.R., et al.; "Improved tolls for biological sequence comparison"; Proc. Natl. Acad. Sci. USA 85 (1988) 2444-2448.
Altschul, S.F., et al.; "Basic Local Alignment Search Tool"; J. Mol. Biol. 215 (1990) 403-410.
Gish, et al.; "Identification of protein coding regions by database similarity search"; Nature Genetics 3 (1993) 266-272.
Karlin, S., et al.; "Applications and statistics for multiple high-scoring segments in molecular sequences"; Proc. Natl. Acad. Sci. USA 90 (1993) 5873-5877.
Altschul, S., et al.; "Local Alignment Statistics"; Methods in Enzymology 266 (1996) 460-481.
Ballard, J.D., et al.; "Certified U.S. Appl. No. 60/389,685"; filed Jun. 17, 2002; 43 pages.
Persing, D.H., et al.; "Taking toll: lipid A mimetics as adjuvants and immunomodulators"; Trends in Microbiology 10:10 Suppl. (2002) 32-38.
Aslam, S., et al.; "Treatment of Clostridium difficile-associated disease: old therapies and new strategies"; Lancet Infect Dis 5 (2005) 549-558.
Devera, T.S., et al.; "Glycolipid-activated NKT cells support the induction of persistent plasma cell responses and antibody titers"; Eur J Immunol. 38:4 (2008) 1001-1011.
Piscataway, N.J.; "GenScript Upgrades OptimumGeneTM Gene Design System"; Nov. 3, 2008; (abstract only); 2 pages.
Vohra, P., et al.; "Induction of cytokines in a macrophage cell line by proteins of Clostridium difficile"; FEMS Immunol Med Microbiol 65 (2012) 96-104.
Thomas, S. (editor); "Vaccine Designs—Methods and Protocols—vol. 1—Vaccines for Human Diseases"; Methods in Molecular Biology (2016) 865 pages.
Bioclone Inc.; "Clostridium difficile toxin B"; Bioclone Inc.; (viewed Sep. 2018); (abstract only); 1 page.

* cited by examiner

A

B

SEQUENCE LISTING

```
<160> NUMBER OF SEQ ID NOS: 68

<210> SEQ ID NO 1
<211> LENGTH: 11
<212> TYPE: PRT
<213> ORGANISM: Clostridium difficile
<220> FEATURE:
<221> NAME/KEY: PEPTIDE
<222> LOCATION: (1)..(11)

<400> SEQUENCE: 1

Asn Val Phe Lys Gly Asn Thr Ile Ser Asp Lys
1               5                   10

<210> SEQ ID NO 2
<211> LENGTH: 20
<212> TYPE: PRT
<213> ORGANISM: Clostridium difficile
<220> FEATURE:
<221> NAME/KEY: PEPTIDE
<222> LOCATION: (1)..(20)

<400> SEQUENCE: 2

Asp Phe Ile Leu Met Ser Thr Asp Glu Glu Asn Lys Val Ser Gln Val
1               5                   10                  15

Lys Ile Arg Phe
            20

<210> SEQ ID NO 3
<211> LENGTH: 18
<212> TYPE: PRT
<213> ORGANISM: Clostridium difficile
<220> FEATURE:
```

```
<221> NAME/KEY: PEPTIDE
<222> LOCATION: (1)..(18)

<400> SEQUENCE: 3

Met Ser Thr Asp Glu Glu Asn Lys Val Ser Gln Val Lys Ile Arg Phe
1               5                   10                  15

Thr Asn

<210> SEQ ID NO 4
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 4

Ser Gln Val Lys Ile Arg Phe Thr Asn Val Phe Lys Gly Asn Thr Ile
1               5                   10                  15

Ser Asp Lys

<210> SEQ ID NO 5
<211> LENGTH: 17
<212> TYPE: PRT
<213> ORGANISM: Clostridium difficile
<220> FEATURE:
<221> NAME/KEY: PEPTIDE
<222> LOCATION: (1)..(17)

<400> SEQUENCE: 5

Arg Phe Thr Asn Val Phe Lys Gly Asn Thr Ile Ser Asp Lys Ile Ser
1               5                   10                  15

Phe

<210> SEQ ID NO 6
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 6

Asn Val Phe Lys Gly Asn Thr Ile Ser Asp Lys Ile Ser Phe Asn Ser
1               5                   10                  15

Phe Asp Lys

<210> SEQ ID NO 7
<211> LENGTH: 18
<212> TYPE: PRT
<213> ORGANISM: Clostridium difficile
<220> FEATURE:
<221> NAME/KEY: PEPTIDE
<222> LOCATION: (1)..(18)

<400> SEQUENCE: 7

Phe Asn Phe Ser Asp Lys Gln Asp Val Ser Ile Asn Lys Val Ile Ser
1               5                   10                  15

Thr Phe

<210> SEQ ID NO 8
<211> LENGTH: 19
<212> TYPE: PRT
<213> ORGANISM: Clostridium difficile
```

```
<220> FEATURE:
<221> NAME/KEY: PEPTIDE
<222> LOCATION: (1)..(19)

<400> SEQUENCE: 8

Lys Gln Asp Val Ser Ile Asn Lys Val Ile Ser Thr Phe Thr Pro Ser
1               5                   10                  15

Tyr Tyr Val

<210> SEQ ID NO 9
<211> LENGTH: 17
<212> TYPE: PRT
<213> ORGANISM: Clostridium difficile
<220> FEATURE:
<221> NAME/KEY: PEPTIDE
<222> LOCATION: (1)..(17)

<400> SEQUENCE: 9

Glu Gly Leu Leu Asn Tyr Asp Leu Gly Leu Ile Ser Leu Tyr Asn Glu
1               5                   10                  15

Lys

<210> SEQ ID NO 10
<211> LENGTH: 21
<212> TYPE: PRT
<213> ORGANISM: Clostridium difficile
<220> FEATURE:
<221> NAME/KEY: PEPTIDE
<222> LOCATION: (1)..(21)

<400> SEQUENCE: 10

Lys Pro Pro Ile Lys Asn Leu Ile Thr Gly Phe Thr Thr Ile Gly Asp
1               5                   10                  15

Asp Lys Tyr Tyr Phe
            20

<210> SEQ ID NO 11
<211> LENGTH: 20
<212> TYPE: PRT
<213> ORGANISM: Clostridium difficile
<220> FEATURE:
<221> NAME/KEY: PEPTIDE
<222> LOCATION: (1)..(20)

<400> SEQUENCE: 11

Lys Asn Leu Ile Thr Gly Phe Thr Thr Ile Gly Asp Asp Lys Tyr Tyr
1               5                   10                  15

Phe Asn Pro Asp
            20

<210> SEQ ID NO 12
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 12

Asp Asp Lys Tyr Tyr Phe Asn Pro Asp Asn Gly Gly Ala Ala Ser Val
1               5                   10                  15

Gly Glu Thr

<210> SEQ ID NO 13
```

```
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 13

Gln Thr Gly Val Phe Ser Thr Glu Asp Gly Phe Lys Tyr Phe Ala Pro
1               5                   10                  15

Ala Asp Thr

<210> SEQ ID NO 14
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 14

Thr Gly Arg Ala Phe Lys Gly Leu Asn Gln Ile Gly Asp Asp Lys Phe
1               5                   10                  15

Tyr Phe Asn

<210> SEQ ID NO 15
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 15

Asn Val Phe Lys Asp Lys Thr Leu Ala Asn Lys Leu Ser Phe Asn Phe
1               5                   10                  15

Ser Asp Lys

<210> SEQ ID NO 16
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Mutant of SEQ ID NO:6

<400> SEQUENCE: 16

Asn Val Phe Lys Asp Lys Thr Ile Ser Asp Lys Ile Ser Phe Asn Phe
1               5                   10                  15

Ser Asp Lys

<210> SEQ ID NO 17
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Mutant of SEQ ID NO:6

<400> SEQUENCE: 17

Asn Val Phe Lys Gly Asn Thr Leu Ala Asn Lys Leu Ser Phe Asn Phe
1               5                   10                  15

Ser Asp Lys
```

<210> SEQ ID NO 18
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Mutant of SEQ ID NO:6

<400> SEQUENCE: 18

Asn Val Phe Lys Asp Asn Thr Ile Ser Asp Lys Ile Ser Phe Asn Phe
1               5                   10                  15

Ser Asp Lys

<210> SEQ ID NO 19
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Mutant of SEQ ID NO:6

<400> SEQUENCE: 19

Asn Val Phe Lys Ser Asn Thr Ile Ser Asp Lys Ile Ser Phe Asn Phe
1               5                   10                  15

Ser Asp Lys

<210> SEQ ID NO 20
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Mutant of SEQ ID NO:6

<400> SEQUENCE: 20

Asn Val Phe Lys Gly Lys Thr Ile Ser Asp Lys Ile Ser Phe Asn Phe
1               5                   10                  15

Ser Asp Lys

<210> SEQ ID NO 21
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Mutant of SEQ ID NO:6

<400> SEQUENCE: 21

Asn Val Ala Lys Gly Asn Thr Ile Ser Asp Lys Ile Ser Ala Asn Ala
1               5                   10                  15

Ser Asp Lys

<210> SEQ ID NO 22
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Mutant of SEQ ID NO:6

<400> SEQUENCE: 22

Asn Val Trp Lys Gly Asn Thr Ile Ser Asp Lys Ile Ser Trp Asn Trp
1               5                   10                  15

Ser Asp Lys

<210> SEQ ID NO 23
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Mutant of SEQ ID NO:6

<400> SEQUENCE: 23

Asn Val Tyr Lys Gly Asn Thr Ile Ser Asp Lys Ile Ser Tyr Asn Tyr
1               5                   10                  15

Ser Asp Lys

<210> SEQ ID NO 24
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 24

Asn Val Phe Lys Gly Asn Thr Ile Ser Asp Lys Ile Ser Phe Asn Phe
1               5                   10                  15

<210> SEQ ID NO 25
<211> LENGTH: 14
<212> TYPE: PRT
<213> ORGANISM: Clostridium difficile
<220> FEATURE:
<221> NAME/KEY: PEPTIDE
<222> LOCATION: (1)..(14)

<400> SEQUENCE: 25

Asn Val Phe Lys Gly Asn Thr Ile Ser Asp Lys Ile Ser Phe
1               5                   10

<210> SEQ ID NO 26
<211> LENGTH: 11
<212> TYPE: PRT
<213> ORGANISM: Clostridium difficile
<220> FEATURE:
<221> NAME/KEY: PEPTIDE
<222> LOCATION: (1)..(11)

<400> SEQUENCE: 26

Asn Val Phe Lys Gly Asn Thr Ile Ser Asp Lys
1               5                   10

<210> SEQ ID NO 27
<211> LENGTH: 17
<212> TYPE: PRT
<213> ORGANISM: Clostridium difficile
<220> FEATURE:
<221> NAME/KEY: PEPTIDE
<222> LOCATION: (1)..(17)

<400> SEQUENCE: 27

Phe Lys Gly Asn Thr Ile Ser Asp Lys Ile Ser Phe Asn Phe Ser Asp
1               5                   10                  15

Lys

<210> SEQ ID NO 28
<211> LENGTH: 16
<212> TYPE: PRT
<213> ORGANISM: Clostridium difficile
<220> FEATURE:
<221> NAME/KEY: PEPTIDE
<222> LOCATION: (1)..(16)

<400> SEQUENCE: 28

Lys Gly Asn Thr Ile Ser Asp Lys Ile Ser Phe Asn Phe Ser Asp Lys
1               5                   10                  15

<210> SEQ ID NO 29
<211> LENGTH: 12
<212> TYPE: PRT
<213> ORGANISM: Clostridium difficile
<220> FEATURE:
<221> NAME/KEY: PEPTIDE
<222> LOCATION: (1)..(12)

<400> SEQUENCE: 29

Phe Lys Gly Asn Thr Ile Ser Asp Lys Ile Ser Phe
1               5                   10

<210> SEQ ID NO 30
<211> LENGTH: 10
<212> TYPE: PRT
<213> ORGANISM: Clostridium difficile
<220> FEATURE:
<221> NAME/KEY: PEPTIDE
<222> LOCATION: (1)..(10)

<400> SEQUENCE: 30

Gly Asn Thr Ile Ser Asp Lys Ile Ser Phe
1               5                   10

<210> SEQ ID NO 31
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 31

Ser Ser Lys Asp Lys Ile Val Ser Phe Lys Asn Gly Phe Thr Phe Asp
1               5                   10                  15

Ile Asn Asn

<210> SEQ ID NO 32
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 32

Ile Lys Lys Ser Asn Val Phe Asn Ser Phe Phe Asp Ser Ile Asn Gly
1               5                   10                  15

-continued

Lys Thr Asp

<210> SEQ ID NO 33
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 33

Phe Gly Asn Lys Phe Thr Ser Val Asp Asn Ser Lys Ile Lys Phe Ile
1               5                   10                  15

Asp Ser Asn

<210> SEQ ID NO 34
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 34

Ile Gly Val Phe Ser Asn Asp Lys Lys Asn Ile Asn Thr Ser Phe Asp
1               5                   10                  15

Phe Ser Lys

<210> SEQ ID NO 35
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 35

Lys Phe Val Phe Asp Asp Ile Lys Asn Ser Ser Ile Ser Asn Lys Thr
1               5                   10                  15

Phe Asn Gly

<210> SEQ ID NO 36
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 36

Gly Ser Ser Ser Ile Ile Asn Asp Asp Phe Lys Asn Val Thr Lys Asn
1               5                   10                  15

Lys Phe Phe

<210> SEQ ID NO 37
<211> LENGTH: 19
<212> TYPE: PRT
<213> ORGANISM: Artificial Sequence

```
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 37

Phe Lys Asp Asn Asn Ser Ile Ile Phe Asp Val Lys Gly Thr Asn Phe
1               5                   10                  15

Ser Ser Lys

<210> SEQ ID NO 38
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 38

Asp Lys Phe Ser Asn Ser Asn Lys Asp Lys Ile Ser Phe Gly Asn Val
1               5                   10                  15

Thr Phe Ile

<210> SEQ ID NO 39
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 39

Asn Phe Asn Ile Ser Val Ser Lys Asp Phe Phe Ser Gly Lys Thr Asn
1               5                   10                  15

Ile Asp Lys

<210> SEQ ID NO 40
<211> LENGTH: 19
<212> TYPE: PRT
<213> ORGANISM: Artificial Sequence
<220> FEATURE:
<221> NAME/KEY: PEPTIDE
<222> LOCATION: (1)..(19)
<223> OTHER INFORMATION: Completely synthesized in the lab using random
      combinations of amino acids of SEQ ID NO:6.

<400> SEQUENCE: 40

Ser Asn Lys Asn Phe Ser Gly Ile Val Phe Thr Asn Phe Asp Ile Asp
1               5                   10                  15

Lys Ser Lys

<210> SEQ ID NO 41
<211> LENGTH: 18
<212> TYPE: PRT
<213> ORGANISM: Clostridium difficile
<220> FEATURE:
<221> NAME/KEY: PEPTIDE
<222> LOCATION: (1)..(18)

<400> SEQUENCE: 41

Met Ser Thr Ser Glu Glu Asn Lys Val Ser Gln Val Lys Ile Arg Phe
```

```
1               5                   10                  15
Val Asn

<210> SEQ ID NO 42
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 42

Ser Gln Val Lys Ile Arg Phe Val Met Val Phe Lys Asp Lys Thr Leu
1               5                   10                  15

Ala Asn Lys

<210> SEQ ID NO 43
<211> LENGTH: 17
<212> TYPE: PRT
<213> ORGANISM: Clostridium difficile
<220> FEATURE:
<221> NAME/KEY: PEPTIDE
<222> LOCATION: (1)..(17)

<400> SEQUENCE: 43

Arg Phe Val Asn Val Phe Lys Asp Lys Thr Leu Ala Asn Lys Leu Ser
1               5                   10                  15

Phe

<210> SEQ ID NO 44
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 44

Asn Val Phe Lys Asp Lys Thr Leu Ala Asn Lys Leu Ser Phe Asn Phe
1               5                   10                  15

Ser Asp Lys

<210> SEQ ID NO 45
<211> LENGTH: 17
<212> TYPE: PRT
<213> ORGANISM: Clostridium difficile
<220> FEATURE:
<221> NAME/KEY: PEPTIDE
<222> LOCATION: (1)..(17)

<400> SEQUENCE: 45

Arg Tyr Leu Glu Glu Ser Asn Lys Lys Ile Leu Gln Lys Ile Arg Ile
1               5                   10                  15

Lys

<210> SEQ ID NO 46
<211> LENGTH: 22
<212> TYPE: PRT
<213> ORGANISM: Clostridium difficile
<220> FEATURE:
<221> NAME/KEY: PEPTIDE
<222> LOCATION: (1)..(22)

<400> SEQUENCE: 46
```

Glu Glu Ser Asn Lys Lys Ile Leu Gln Lys Ile Arg Ile Lys Gly Ile
1               5                   10                  15

Leu Ser Asn Thr Gln Ser
            20

<210> SEQ ID NO 47
<211> LENGTH: 20
<212> TYPE: PRT
<213> ORGANISM: Clostridium difficile
<220> FEATURE:
<221> NAME/KEY: PEPTIDE
<222> LOCATION: (1)..(20)

<400> SEQUENCE: 47

Ser Asn Lys Lys Ile Leu Gln Lys Ile Arg Ile Lys Gly Ile Leu Ser
1               5                   10                  15

Asn Thr Gln Ser
            20

<210> SEQ ID NO 48
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 48

Lys Gly Ile Leu Ser Asn Thr Gln Ser Phe Asn Lys Met Ser Ile Asp
1               5                   10                  15

Phe Lys Asp

<210> SEQ ID NO 49
<211> LENGTH: 22
<212> TYPE: PRT
<213> ORGANISM: Clostridium difficile
<220> FEATURE:
<221> NAME/KEY: PEPTIDE
<222> LOCATION: (1)..(22)

<400> SEQUENCE: 49

Ser Phe Asn Lys Met Ser Ile Asp Phe Lys Asp Ile Lys Lys Leu Ser
1               5                   10                  15

Leu Gly Tyr Ile Met Ser
            20

<210> SEQ ID NO 50
<211> LENGTH: 21
<212> TYPE: PRT
<213> ORGANISM: Clostridium difficile
<220> FEATURE:
<221> NAME/KEY: PEPTIDE
<222> LOCATION: (1)..(21)

<400> SEQUENCE: 50

Ser Leu Gly Tyr Ile Met Ser Asn Phe Lys Ser Phe Asn Ser Glu Asn
1               5                   10                  15

Glu Leu Asp Arg Asp
            20

<210> SEQ ID NO 51
<211> LENGTH: 20
<212> TYPE: PRT
<213> ORGANISM: Clostridium difficile
<220> FEATURE:

```
<221> NAME/KEY: PEPTIDE
<222> LOCATION: (1)..(20)

<400> SEQUENCE: 51

Ser Asn Phe Lys Ser Phe Asn Ser Glu Asn Glu Leu Asp Arg Asp His
1               5                   10                  15

Leu Gly Phe Lys
            20

<210> SEQ ID NO 52
<211> LENGTH: 20
<212> TYPE: PRT
<213> ORGANISM: Clostridium difficile
<220> FEATURE:
<221> NAME/KEY: PEPTIDE
<222> LOCATION: (1)..(20)

<400> SEQUENCE: 52

Lys Phe Ser Asn Ser Glu Asn Glu Leu Asp Arg Asp His Leu Gly Phe
1               5                   10                  15

Lys Ile Ile Asp
            20

<210> SEQ ID NO 53
<211> LENGTH: 20
<212> TYPE: PRT
<213> ORGANISM: Clostridium difficile
<220> FEATURE:
<221> NAME/KEY: PEPTIDE
<222> LOCATION: (1)..(20)

<400> SEQUENCE: 53

Arg Asp His Leu Gly Phe Lys Ile Ile Asp Asn Lys Thr Tyr Tyr Tyr
1               5                   10                  15

Asp Glu Asp Ser
            20

<210> SEQ ID NO 54
<211> LENGTH: 18
<212> TYPE: PRT
<213> ORGANISM: Clostridium difficile
<220> FEATURE:
<221> NAME/KEY: PEPTIDE
<222> LOCATION: (1)..(18)

<400> SEQUENCE: 54

Ile Ala Asn Ser Glu Glu Asp Asn Gln Pro Gln Val Lys Ile Arg Phe
1               5                   10                  15

Val Asn

<210> SEQ ID NO 55
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 55

Pro Gln Val Lys Ile Arg Phe Val Asn Val Phe Lys Ser Asp Thr Ala
1               5                   10                  15

Ala Asp Lys

<210> SEQ ID NO 56
```

```
<211> LENGTH: 17
<212> TYPE: PRT
<213> ORGANISM: Clostridium difficile
<220> FEATURE:
<221> NAME/KEY: PEPTIDE
<222> LOCATION: (1)..(17)

<400> SEQUENCE: 56

Arg Phe Val Asn Val Phe Lys Ser Asp Thr Ala Ala Asp Lys Leu Ser
1               5                   10                  15

Phe

<210> SEQ ID NO 57
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 57

Asn Val Phe Lys Ser Asp Thr Ala Ala Asp Lys Leu Ser Phe Asn Phe
1               5                   10                  15

Ser Asp Lys

<210> SEQ ID NO 58
<211> LENGTH: 18
<212> TYPE: PRT
<213> ORGANISM: Clostridium difficile
<220> FEATURE:
<221> NAME/KEY: PEPTIDE
<222> LOCATION: (1)..(18)

<400> SEQUENCE: 58

Phe Asn Phe Ser Asp Lys Gln Asp Val Ser Val Ser Lys Ile Ile Ser
1               5                   10                  15

Thr Phe

<210> SEQ ID NO 59
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 59

Lys Asp Phe Lys Trp Asp Ile Lys Gly Asn Asp Ile Ile Leu Val Arg
1               5                   10                  15

Lys Lys Ile

<210> SEQ ID NO 60
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 60

Ile Ile Leu Val Arg Lys Lys Ile Asn Gly Phe Asn Ser Thr Ile Leu
1               5                   10                  15

Leu Lys Asp
```

```
<210> SEQ ID NO 61
<211> LENGTH: 19
<212> TYPE: PRT
<213> ORGANISM: Clostridium difficile
<220> FEATURE:
<221> NAME/KEY: PEPTIDE
<222> LOCATION: (1)..(19)

<400> SEQUENCE: 61

Lys Lys Ile Asn Gly Phe Asn Ser Thr Ile Leu Leu Lys Asp Thr Ile
1               5                   10                  15

Asp Asn Asn

<210> SEQ ID NO 62
<211> LENGTH: 20
<212> TYPE: PRT
<213> ORGANISM: Clostridium difficile
<220> FEATURE:
<221> NAME/KEY: PEPTIDE
<222> LOCATION: (1)..(20)

<400> SEQUENCE: 62

Lys Asp Thr Ile Asp Asn Asn Ser Tyr Phe Asn Tyr Val Thr Leu Ile
1               5                   10                  15

Phe Asn Asp Lys
            20

<210> SEQ ID NO 63
<211> LENGTH: 13
<212> TYPE: PRT
<213> ORGANISM: Human immunodeficiency virus-1
<220> FEATURE:
<221> NAME/KEY: PEPTIDE
<222> LOCATION: (1)..(13)
<223> OTHER INFORMATION: TAT

<400> SEQUENCE: 63

Gly Arg Lys Lys Arg Arg Gln Arg Arg Pro Pro Gln
1               5                   10

<210> SEQ ID NO 64
<211> LENGTH: 21
<212> TYPE: PRT
<213> ORGANISM: Artificial Sequence
<220> FEATURE:
<221> NAME/KEY: PEPTIDE
<222> LOCATION: (1)..(21)
<223> OTHER INFORMATION: Pep-1

<400> SEQUENCE: 64

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 65
<211> LENGTH: 21
<212> TYPE: PRT
<213> ORGANISM: Artificial Sequence
<220> FEATURE:
<221> NAME/KEY: PEPTIDE
<222> LOCATION: (1)..(21)
<223> OTHER INFORMATION: Transportan

<400> SEQUENCE: 65

Ala Gly Tyr Leu Leu Gly Lys Ile Asn Leu Lys Ala Leu Ala Ala Leu
1               5                   10                  15
```

Ala Lys Lys Ile Leu
            20

<210> SEQ ID NO 66
<211> LENGTH: 16
<212> TYPE: PRT
<213> ORGANISM: Drosophila melanogaster
<220> FEATURE:
<221> NAME/KEY: PEPTIDE
<222> LOCATION: (1)..(16)
<223> OTHER INFORMATION: Penetratin

<400> SEQUENCE: 66

Arg Gln Ile Lys Ile Trp Phe Gln Asn Arg Arg Met Lys Trp Lys Lys
1               5                   10                  15

<210> SEQ ID NO 67
<211> LENGTH: 11
<212> TYPE: PRT
<213> ORGANISM: Artificial Sequence
<220> FEATURE:
<223> OTHER INFORMATION: Completely synthesized in the lab, mutant of
      SEQ ID NO:1.
<220> FEATURE:
<221> NAME/KEY: Variant
<222> LOCATION: (1)..(1)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (2)..(2)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (3)..(3)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val or L-phe,
      L-met, L-leu, L-ile, D-phe, D-met, D-leu and D-ile
<220> FEATURE:
<221> NAME/KEY: VARIANT
<222> LOCATION: (4)..(4)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (5)..(5)
<223> OTHER INFORMATION: Xaa can be gly, L-ala, L-ser, D-ala, and D-ser
<220> FEATURE:
<221> NAME/KEY: VARIANT
<222> LOCATION: (6)..(6)
<223> OTHER INFORMATION: Xaa can be L-asn, L-asp, L-gln, L-his, L-ser,
      L-thr, D-asn, D-asp, D-gln, D-his, D-ser, and D-thr
<220> FEATURE:
<221> NAME/KEY: VARIANT
<222> LOCATION: (7)..(7)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT

```
<222> LOCATION: (8)..(8)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (9)..(9)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (10)..(10)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (11)..(11)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val

<400> SEQUENCE: 67

Xaa Xaa Xaa Xaa Xaa Xaa Xaa Xaa Xaa Xaa Xaa
1               5                   10

<210> SEQ ID NO 68
<211> LENGTH: 19
<212> TYPE: PRT
<213> ORGANISM: Artificial Sequence
<220> FEATURE:
<223> OTHER INFORMATION: Completely synthesized in the lab, mutant of
      SEQ ID NO:6.
<220> FEATURE:
<221> NAME/KEY: variant
<222> LOCATION: (1)..(1)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (2)..(2)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (3)..(3)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val or L-phe,
      L-met, L-leu, L-ile, D-phe, D-met, d-leu, and D-ile
<220> FEATURE:
<221> NAME/KEY: VARIANT
<222> LOCATION: (4)..(4)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
```

```
<222> LOCATION: (5)..(5)
<223> OTHER INFORMATION: Xaa can be gly, L-ala, L-ser, D-ala, and D-ser
      or L-gly, L-asn, D-gly, D-asn
<220> FEATURE:
<221> NAME/KEY: VARIANT
<222> LOCATION: (6)..(6)
<223> OTHER INFORMATION: Xaa can be L-asn, L-asp, L-gln, L-his, L-ser,
      L-thr, D-asn, D-asp, D-gln, D-his, D-ser, and D-thr or L-gly,
      L-asn, D-gly, D-asn
<220> FEATURE:
<221> NAME/KEY: VARIANT
<222> LOCATION: (7)..(7)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (8)..(8)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (9)..(9)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (10)..(10)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (11)..(11)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (12)..(12)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (13)..(13)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (14)..(14)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (15)..(15)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
```

```
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (16)..(16)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (17)..(17)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (18)..(18)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val
<220> FEATURE:
<221> NAME/KEY: VARIANT
<222> LOCATION: (19)..(19)
<223> OTHER INFORMATION: Xaa can be gly, L-ala, L-arg, L-asn, L-asp,
      L-cys, L-glu, L-gln, L-his, L-ile, L-leu, L-lys, L- met, L-phe,
      L-pro, L-ser, L-thr, L-trp, L-tyr, L-val, D-ala, D-arg, D-asn,
      D-asp, D-cys, D-glu, D-gln, D-his, D-ile, D-leu, D-lys, D-met,
      D-phe, D-pro, D-ser, D-thr, D-trp, D-tyr, and D-val

<400> SEQUENCE: 68

Xaa Xaa Xaa Xaa Xaa Xaa Xaa Xaa Xaa Xaa Xaa Xaa Xaa Xaa Xaa Xaa
1               5                   10                  15

Xaa Xaa Xaa
```

PEPTIDE INHIBITORS OF CLOSTRIDIUM DIFFICILE TOXIN B (TCDB) TOXIN

CROSS-REFERENCE TO RELATED APPLICATIONS

The present application is a national stage application of a PCT application having International Application No. PCT/US2016/050038, filed Sep. 2, 2016, which claims priority to U.S. Provisional Application having U.S. Ser. No. 62/214,082, filed Sep. 3, 2015, which claims the benefit under 35 U.S.C. 119(e), the disclosure of which is hereby expressly incorporated herein by reference.

GOVERNMENT SUPPORT

This invention was made with government support under Grant Nos. AI119048 and AI121925 granted by the National Institutes of Health. The government has certain rights in the invention.

BACKGROUND

*Clostridium difficile* (*C. difficile*) causes debilitating antibiotic associated diarrhea in hospital patients and is a pathogen in which alternatives to antibiotic therapies are necessitated. *C. difficile* infections (CDI) are dependent on the production of the intracellular toxins, including TcdB, whose sequence and toxicity varies among different strains of *C. difficile*. The most recent reports estimate nearly 500,000 cases of *C. difficile* infection in the US every year, with total deaths approaching 30,000 annually. Treatment options are very expensive and obviously are not ideal or even very effective given the steady rise in the number and severity of *C. difficile* infections. There are a number of anti-toxin technologies available or proposed for treating *C. difficile* infections. These include (1) humanized monoclonal antibodies against TcdA and TcdB (from Merck, in Phase III trials) which are effective against multiple ribotypes of *C. difficile* and reduce rates of *C. difficile* recurrence (however, these are likely to be cost-prohibitive except in severe cases), (2) fecal microbiota transplantation (FMT), which is a cost effective treatment for patients with recurring *C. difficile* disease, but is not used to treat primary infection, (3) toxoid vaccines of TcdB and TcdA toxins, which are in phase-III clinical trials at Sanofi (e.g., Cdiffense trial), and which may be highly effective, but will only be used on a specific group of individuals and not in treatments for active disease or community-acquired *C. difficile*, and (4) atoxigenic *C. difficile* which has been used to compete with toxic strains of *C. difficile* in the intestinal tract.

Currently there are no peptide-based inhibitors approved for treatment of bacterial toxins, including *C. difficile* toxins. However, such a drug could reach a large patient market, as noted above. In 2014 there were 500-600 peptides in preclinical trials, 40 in phase-I trials, 74 in phase-II trials, and 14 in phase-III trials. These trials included both use of peptides as vaccines and for treatment of acute conditions. About 100 therapeutic peptides, including diagnostics are on the market in the US, Europe and Japan. Examples of major peptides in this market are Goserelin/Zoladex and Leuroprolide used to treat breast and prostate cancer and Octreotide used to treat various tumors. Annual sales are between $US 1.2 and 1.4 billion. Thus there is a growing precedent for considering peptides as therapeutics. A therapy that targets TcdB along with variant forms of this toxin would be an ideal approach to counter CDI and could serve as alternative to antibiotics. It is to such peptide-based therapeutics for the treatment of CDIs that the present disclosure is directed.

BRIEF DESCRIPTION OF THE DRAWINGS

Several embodiments of the present disclosure are hereby illustrated in the appended drawings. It is to be noted however, that the appended drawings only illustrate several typical embodiments and are therefore not intended to be considered limiting of the scope of the present disclosure.

FIG. 28 shows dose-dependent inhibition of TcdB by a synthetic peptide derived from positions 1774-1795 of the TcdA toxin, designated $TcdA_{1774-1795}$. The amino acid sequence of $TcdA_{1774-1795}$ is shown in Table 6 (SEQ ID NO:49). The bar graph shows the percent of viable CHO-K1 cells after treatment for 24 h with TcdB in the presence of 50 μM and 50 μM of the $TcdA_{1774-1795}$ peptide. Data are presented as mean (n=3)±S.D.

FIGS. 29A, 29B, 29C, and 29D depict results showing the cell penetrating activities of PepB2 in CHO-K1 cells subjected to flow cytometry analysis after exposing the cells for 30 min at 37° C. to 100 nM $CROP_{AF488}$ in the presence and absence of 50 μM PepB2. For quenching experiments, cells were exposed to 0.2% trypan blue immediately before flow cytometry analysis. The signal that is not quenched represents quantity taken up by cells. Histograms (righthand) represent fluorescent signal associated with cells before and after quenching. In the bar graphs, flow cytometry results are presented as median fluorescence intensity (MFI) from 3 experiments.

FIGS. 30A, 30B, 30C and 30D depict results showing the cell penetrating activities of PepB2 in CHO-K1 cells subjected to flow cytometry analysis after exposing the cells for 30 min at 37° C. to 125 nM $transferrin_{AF488}$ in the presence and absence of 50 μM PepB2. For quenching experiments, cells were exposed to 0.2% trypan blue immediately before flow cytometry analysis. The signal that is not quenched represents quantity taken up by cells. Histograms (righthand) represent fluorescent signal associated with cells before and after quenching. In the bar graphs, flow cytometry results are presented as MFI from 3 experiments.

FIGS. 31A, 31B, 31C and 31D depict results showing the cell penetrating activities of PepB2 in CHO-K1 cells subjected to flow cytometry analysis after exposing the cells for 30 min at 37° C. to 100 μg/ml $dextran_{AF488}$ in the presence and absence of 50 μM PepB2. For quenching experiments, cells were exposed to 0.2% trypan blue immediately before flow cytometry analysis. The signal that is not quenched represents quantity taken up by cells. Histograms (righthand) represent fluorescent signal associated with cells before and after quenching. In the bar graphs, flow cytometry results are presented as MFI from 3 experiments.

FIGS. 32A, 32B, 32C and 32D depict results showing the cell penetrating activities of PepB2 in CHO-K1 cells subjected to flow cytometry analysis after exposing the cells for 30 min at 37° C. to 100 nM $dsRNA_{fluorescein}$ in the presence and absence of 50 μM PepB2. For quenching experiments, cells were exposed to 0.2% trypan blue immediately before flow cytometry analysis. The signal that is not quenched represents quantity taken up by cells. Histograms (righthand) represent fluorescent signal associated with cells before and after quenching. In the bar graphs, flow cytometry results are presented as MFI from 3 experiments.

FIGS. 33A, 33B and 33C depict results showing the cell penetrating activities of PepB2 and PepB1 in CHO-K1 cells subjected to flow cytometry analysis after exposing the cells for 30 min at 37° C. to biotinylated PepB1 and PepB2 synthesized and loaded with Alexa Fluor 488 streptavidin ($streptavidin_{AF488}$). This mixture was prepared with 50 μM biotinylated peptide and 2 μg/ml $streptavidin_{AF488}$. After a 10 min incubation, the mixture was added to the CHO-K1 cells (E) Histograms represent fluorescent signal associated with cells before and after quenching with 0.2% trypan blue. Bar graphs are flow cytometry results presented as MFI from 3 experiments. The results demonstrate that PepB2 is able to bind and carry streptavidin into cells; PepB1 is also able to carry streptavidin into cells, but at a much lower level than that observed for PepB2.

FIG. 34 shows an analysis of the cell penetrating activities of the peptide variants shown in Table 2. 100 μg/ml $dextran_{AF488}$ was combined with 50 μM of the mutant peptides and exposed to CHO-K1 cells for 30 min at 37° C. The cells were then analyzed by flow cytometry and the results are presented in a bar graph as MFI.

FIG. 35 shows an analysis of the cell penetrating activities of the peptide variants shown in Table 2. 100 nM $CROP_{AF488}$ was combined with 50 μM of the mutant peptides and exposed to CHO-K1 cells for 30 min at 37° C. The cells were then analyzed by flow cytometry and the results are presented in a bar graph as MFI.

FIG. 36 shows an analysis of the cell penetrating activities of the peptide variants shown in Table 2. 100 nM $CROP_{AF488}$, was combined with 50 μM of the mutant peptides and exposed to CHO-K1 cells for 30 min at 37° C. The cells were then analyzed by flow cytometry and the results are presented in a bar graph as MFI.

FIG. 37 shows an analysis of the cell penetrating activities of the peptide variants shown in Table 2. 100 nM $dSRNA_{fluorescein}$ was combined with 50 μM of the mutant peptides and exposed to CHO-K1 cells for 30 min at 37° C. The cells were then analyzed by flow cytometry and the results are presented in a bar graph as MFI.

FIG. 38 shows an analysis of the cell penetrating activities of the peptide variants shown in Table 2. 100 nM $dsRNA_{fluorescein}$ was combined with 50 μM of the mutant peptides and exposed to CHO-K1 cells for 30 min at 37° C. The cells were then analyzed by flow cytometry and the results are presented in a bar graph as MFI.

FIG. 39 shows the TcdB-inhibiting activity several cell penetrating peptides (Penetratin, TAT, Pep-1, and Transportan 10) that were screened to determine if any possessed TcdB inhibitory activity. The bar graph represents the percent of viable CHO-K1 cells after treatment for 24 h with 37 μM of TcdB in the presence and absence of various CPPs. CPP were used at the following concentrations: 100 μM TAT, 65 μM Pep-1, 80 μM Penetratin and 80 μM Transportan 10. The CPP Penetratin was found to be inhibitory against TcdB.

FIG. 40 shows the percentage of viable CHO-K1 cells after treatment for 24 h with various TcdB concentrations in the presence and absence of 80 μM of Penetratin.

FIG. 41 shows a flow cytometry analysis of CHO-K1 cells exposed for 10 minutes at 37° C. to 20 nM $TcdB_{AF488}$ in the presence and absence of 80 μM of Penetratin. For quenching experiments, cells were exposed to 0.2% trypan blue immediately before flow cytometry analysis. The signal that is not quenched represents TcdB taken up by cells. Histograms (righthand) represent $TcdB_{AF488}$ that associates with cells before and after quenching. In the bar graphs, flow cytometry results are presented as MFI from 3 experiments.

DETAILED DESCRIPTION

Figure 1:
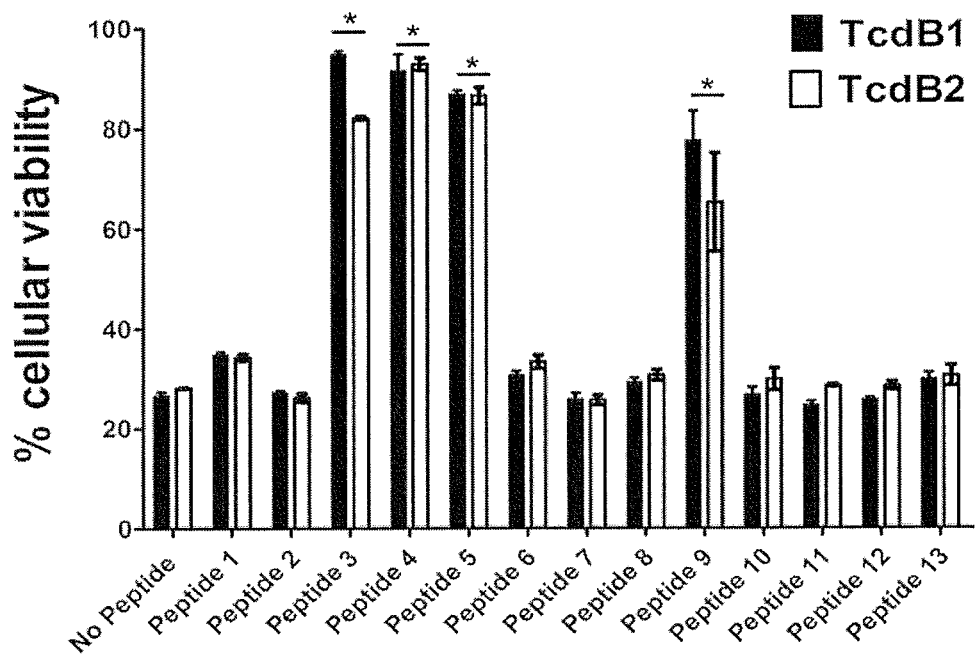
FIG. 1 is a graphical depiction of inhibitory action of various TcdB2-derived peptides against TcdB1 and TcdB2 toxins. Peptides from TcdB2 were synthesized and screened for inhibition of TcdB1 or TcdB2 activity in CHO-K1 cells. The bar graph represents the percent of viable cells after treatment for 24 h with 0.2 pM of TcdB1 or TcdB2 in the presence and absence of 50 μM of peptide. Data are presented as mean (n=3)±S.D. Asterisks indicate significant increase above toxin treated controls. *, p<0.001.

The present disclosure includes, in at least certain embodiments, synthetic peptides and peptide compositions, including peptide conjugates, that can ameliorate and/or block the cytotoxicity of *C. difficile* TcdB, and to methods of their use, for example to inhibit the activity of TcdB and protect against damage during *C. difficile* disease. The present disclosure includes peptides derived from a carboxyl-terminal region of TcdB2 toxin that inhibits the cytotoxicity of both TcdB1 (previously known as $TcdB_{003}$, and $TcdB_{HIST}$, toxinotype 0) and TcdB2 toxins (previously known as $TcdB_{027}$ and $TcdB_{HV}$, toxinotype III. Certain peptides and variants thereof of the present disclosure have also been discovered to be able to function as cell penetrating peptides (CPPs) thus can be used in methods for enhancing the delivery of particular heterogenous molecules, including proteins, peptides, DNA, and therapeutic molecules, into cells. The present disclosure further includes, in at least one embodiment, the use of a CPP known as Penetratin as an inhibitor of TcdB activity.

Before further describing various embodiments of the present disclosure in more detail by way of exemplary description, examples, and results, it is to be understood that the inventive concepts are not limited in application to the details of methods and compositions as set forth in the following description. The embodiments of the present disclosure are capable of being practiced or carried out in various ways. As such, the language used herein is intended to be given the broadest possible scope and meaning; and the embodiments are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the disclosure. However, it will be apparent to a person having ordinary skill in the art that the embodiments of the present disclosure may be practiced without these specific details. In other instances, features which are well known to persons of ordinary skill in the art have not been described in detail to avoid unnecessary complication of the description.

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular.

All patents, published patent applications, and non-patent publications mentioned in the specification are indicative of the level of skill of those skilled in the art to which the present disclosure pertains. All patents, published patent applications, and non-patent publications referenced in any portion of this application are herein expressly incorporated by reference in their entirety to the same extent as if each individual patent or publication was specifically and individually indicated to be incorporated by reference.

All of the compositions and methods of production and application thereof disclosed herein can be made and executed without undue experimentation in light of the present disclosure. While the compositions and methods of the present disclosure have been described in terms of particular embodiments, it will be apparent to those of skill in the art that variations may be applied to the compositions and/or methods and in the steps or in the sequence of steps of the method described herein without departing from the concept, spirit, and scope of the inventive concepts. All such similar substitutes and modifications apparent to those having ordinary skill in the art are deemed to be within the spirit, scope, and concept of the inventive concepts as defined herein.

As utilized in accordance with the methods and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

As used herein, any reference to "one embodiment," "an embodiment," "some embodiments," "one example," "for example," or "an example" means that a particular element, feature, structure or characteristic described in connection with the embodiment is included in at least one embodiment. The appearance of the phrase "in some embodiments" or "one example" in various places in the specification is not necessarily all referring to the same embodiment, for example.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±15%, ±10%, or ±9%, or ±8%, or ±7%, or +6%, or ±5%, or ±4%, or ±3%, or ±2%, or +1%, or +0.5%, or ±0.1% from the specified value, as such variations are appropriate to perform the disclosed methods and as understood by persons having ordinary skill in the art.

As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein, all numerical values or ranges include fractions of the values and integers within such ranges and fractions of the integers within such ranges unless the context clearly indicates otherwise (e.g., when used in reference to the number of amino acid residues in a peptide). Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example.

The term "pharmaceutically acceptable" refers to compounds and compositions which are suitable for administration to humans and/or animals without undue adverse side effects such as toxicity, irritation and/or allergic response commensurate with a reasonable benefit/risk ratio.

By "biologically active" is meant the ability to modify the physiological system of a cell or an organism without reference to how the active agent has its physiological effects.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 75 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species (e.g., the peptide compound) is at least 75% (w/w) pure, or at least 80% (w/w) pure, or at least 85% (w/w) pure, or at least 90% (w/w) pure, or at least 91% (w/w) pure, or at least 92% (w/w) pure, or at least 93% (w/w) pure, or at least 94% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

The terms "subject" and "patient" are used interchangeably herein and will be understood to refer to a warm blooded animal, particularly a mammal. Non-limiting examples of animals within the scope and meaning of this term include dogs, cats, rats, mice, guinea pigs, chinchillas, horses, goats, cattle, sheep, zoo animals, Old and New World monkeys, non-human primates, and humans, and any other animal susceptible to infections by *C. difficile*.

"Treatment" refers to therapeutic treatments. "Prevention" refers to prophylactic or preventative treatment measures. The term "treating" refers to administering the composition to a patient for therapeutic purposes. The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of an active agent which is sufficient to exhibit a detectable effect (therapeutic or otherwise) without excessive adverse side effects (such as toxicity, irritation and allergic response) commensurate with a reasonable benefit/risk ratio when used in the manner of the inventive concepts. The effective amount for a subject will depend upon the type of subject, the subject's size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

More particularly, an effective amount of a peptide compound of the present disclosure refers to an amount which is effective in controlling, reducing, or inhibiting a *C. difficile* infection. The term "controlling" is intended to refer to all processes wherein there may be a slowing, interrupting, arresting, or stopping of the progression of the infection and does not necessarily indicate a total elimination of the infection symptoms. In at least one embodiment the peptide compound is effective in controlling, reducing, or inhibiting the effects of TcdB toxin.

The term "effective amount" is further meant to define an amount resulting in the improvement of any parameters or clinical symptoms characteristic of a *C. difficle* infection. The actual dose will vary with the patient's overall condition, the seriousness of the symptoms, and counter indications. As used herein, the term "effective amount" also means the total amount of each active component of the pharmaceutical composition or method that is sufficient to show a meaningful patient benefit, i.e., reduction of a *C. difficile* infection. When applied to an individual active ingredient, administered alone, the term refers to that ingredient alone. When applied to a combination, the term refers to combined amounts of the active ingredients that result in the therapeutic effect, whether administered in combination, serially or simultaneously.

The term "ameliorate" means a detectable or measurable improvement in a subject's condition, disease or symptom thereof. A detectable or measurable improvement includes a subjective or objective decrease, reduction, inhibition, suppression, limit or control in the occurrence, frequency, severity, progression, or duration of the condition or disease, or an improvement in a symptom or an underlying cause or a consequence of the disease, or a reversal of the disease. A successful treatment outcome can lead to a "therapeutic effect," or "benefit" of ameliorating, decreasing, reducing, inhibiting, suppressing, limiting, controlling or preventing the occurrence, frequency, severity, progression, or duration of a disease or condition, or consequences of the disease or condition in a subject.

A decrease or reduction in worsening, such as stabilizing the condition or disease, is also a successful treatment outcome. A therapeutic benefit therefore need not be complete ablation or reversal of the disease or condition, or any one, most or all adverse symptoms, complications, consequences or underlying causes associated with the disease or condition. Thus, a satisfactory endpoint may be achieved when there is an incremental improvement such as a partial decrease, reduction, inhibition, suppression, limit, control, or prevention in the occurrence, frequency, severity, progression, or duration, or inhibition or reversal of the condition or disease (e.g., stabilizing), over a short or long duration of time (hours, days, weeks, months, etc.). Effectiveness of a method or use, such as a treatment that provides a potential therapeutic benefit or improvement of a condition or disease, can be ascertained by various methods and testing assays.

The following abbreviations may be used herein for amino acids: alanine:ala:A; arginine:arg:R; asparagine:asn:N; aspartic acid:asp:D; cysteine:cys:C; glutamic acid:glu:E; glutamine:gln:Q; glycine:gly:G; histidine:his:H; isoleucine:ile:I; leucine:leu:L; lysine:lys:K; methionine:met:M; phenylalanine:phe:F; proline:pro:P; serine:ser:S; threonine:thr:T; tryptophan:trp:W; tyrosine:tyr:Y; and valine:val:V.

The term "peptide" is used herein to designate a series of amino acid residues, connected one to the other typically by peptide bonds between the alpha-amino and carbonyl groups of the adjacent amino acids to form an amino acid sequence. In certain embodiments, the peptides can range in length from 11 to 15 to 25 to 40 to 60 to 75 to 100 amino acids, for example, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids. The term "polypeptide" or "protein" is used herein to designate a series of amino acid residues, connected one to the other typically by peptide bonds between the alpha-amino and carbonyl groups of the adjacent amino acids, wherein the length is longer than a single peptide. A peptide conjugate refers to a a compound comprising a peptide of the present disclosure which is conjugated (e.g., covalently linked) to a carrier molecule such as a protein or other polymeric molecule, e.g., a serum albumin molecule, wherein the peptide retains its activity (e.g., inhibitory) even when conjugated to the carrier molecule. A "fusion protein" or "fusion polypeptide" refers to proteins or polypeptides (and may be used interchangeably) which have been created by recombinant or synthetic methods to combine peptides in a serial configuration. The peptides of the present disclosure may be produced using any nucleotide sequence which encodes the desired amino acid sequence.

Where used herein the term "anti-TcdB activity" refers to an inhibitory activity against at least one TcdB toxin type, e.g., TcdB1 and/or TcdB2. The term "cell penetrating peptide" where used herein refers to a peptide which is able to translocate across a cell's plasma membrane without a toxic effect on the cell into which the peptide penetrates (unless, for example, it carries a cytotoxic payload).

As used herein "immunogenic composition" refers to a composition containing, for example, peptides, polypeptides, fusion proteins, or carrier molecules with peptides or polypeptides conjugated thereto, which elicits an immune response, such as the production of antibodies in a host cell, or host organism. The immunogenic composition may optionally contain an adjuvant. In certain embodiments, the immunogenic composition is a vaccine.

Where used herein, the term "antigenic fragment" refers to a fragment of an antigenic peptide described herein which is also able to elicit an immunogenic response.

The terms "polynucleotide sequence" or "nucleic acid," as used herein, include any polynucleotide sequence which encodes a peptide or fusion protein (or polypeptide) including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The polynucleotide sequence encoding a peptide or fusion protein, or encoding a therapeutically-effective variant thereof can be substantially the same as the coding sequence of the endogenous coding sequence as long as it encodes an immunogenically-active peptide or fusion protein. Further, the peptide or fusion protein may be expressed using polynucleotide sequence(s) which differ in codon usage due to the degeneracies of the genetic code or allelic variations. Moreover, the peptides and fusion proteins of the present disclosure and the nucleic acids which encode them include peptide/protein and nucleic acid variants which comprise additional substitutions (conservative or non-conservative). For example, the immunogenic peptide variants include, but are not limited to, variants that are not exactly the same as the sequences disclosed herein, but which have, in addition to the substitutions explicitly described for various sequences listed herein, additional substitutions of amino acid residues (conservative or non-conservative) which substantially do not impair the activity or properties of the variants described herein. Examples of such conservative amino acid substitutions may include, but are not limited to, ala to gly, ser, or thr; arg to gln, his, or lys; asn to asp, gln, his, lys, ser, or thr; asp to asn or glu; cys to ser; gln to arg, asn, glu, his, lys, or met; glu to asp, gln, or lys; gly to pro or ala; his to arg, asn, gln, or tyr; ile to leu, met, or val; leu to ile, met, phe, or val; lys to arg, asn, gln, or glu; met to gln, ile, leu, or val; phe to leu, met, trp, or tyr; ser to ala, asn, met, or thr; thr to ala, asn, ser, or met; trp to phe or tyr; tyr to his, phe or trp; and val to ile, leu, or met. One of ordinary skill in the art would readily know how to make, identify, select or test such variants for inhibitory or immunogenic activity against a TcdB toxin (e.g., TcdB2). Particular examples of conservative amino acid substitutions include, but are not limited to, gly:ala substitutions; val:ile:leu substitutions; asn:glu:his substitutions; asp:glu substitutions; ser:thr:met substitutions; lys:arg:hist substitutions; and phe:tyr:trp substitutions. Other types of substitutions, variations, additions, deletions and derivatives that result in functional variant peptides are also encompassed by the present disclosure, and one of skill in the art would readily know how to make, identify, or select such variants or derivatives, and how to test for anti-TcdB or immunogenic activity of those variants. Further, one of ordinary skill in the art may optimize the expression of the peptides of the present disclosure to improve expression by any methods known in the art, including but not limited to, by removing cryptic splice sites, by adapting the codon usage by introducing a Kozak consensus sequence before the start codon, by changing the codon usage, or any combination thereof. Any suitable promoter sequence may be used with the peptide-encoding nucleic acids.

The term "homologous" or "% identity" as used herein means a nucleic acid (or fragment thereof) or a peptide having a degree of homology to the corresponding natural reference nucleic acid or peptide that may be in excess of 60%, or in excess of 65%, or in excess of 70%, or in excess of 75%, or in excess of 80%, or in excess of 85%, or in excess of 90%, or in excess of 91%, or in excess of 92%, or in excess of 93%, or in excess of 94%, or in excess of 95%, or in excess of 96%, or in excess of 97%, or in excess of 98%, or in excess of 99%, or other specific percentages described herein. For example, in regard to peptides, the percentage of homology or identity as described herein is typically calculated as the percentage of amino acid residues found in the smaller of the two sequences which align with identical amino acid residues in the sequence being compared, when four gaps per 100 amino acids may be introduced to assist in that alignment (as set forth by Dayhoff, in Atlas of Protein Sequence and Structure, Vol. 5, p. 124, National Biochemical Research Foundation, Washington, D.C. (1972)). In one embodiment, the percentage homology as described above is calculated as the percentage of the components found in the smaller of the two sequences that may also be found in the larger of the two sequences (with the introduction of gaps), with a component being defined as a sequence of four, contiguous amino acids. Also included as substantially homologous is any protein product which may be isolated by virtue of cross-reactivity with antibodies to the native protein product. Sequence identity or homology can be determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990, 87, 2264-2268, modified as in Karlin & Altschul, Proc. Natl. Acad. Sci. USA 1993, 90, 5873-5877.

In at least one embodiment "% identity" represents the number of amino acids or nucleotides which are identical at corresponding positions in two sequences of a peptide or nucleic acids encoding similar peptides. For example, two amino acid sequences each having 11 residues will have at least 63% identity when at least 7 of the amino acids at corresponding positions are the same, at least 72% identity when at least 8 of the amino acids at corresponding positions are the same, at least 81% identity when at least 9 of the amino acids at corresponding positions are the same, and at least 90% identity when at least 10 of the amino acids at corresponding positions are the same. In another example, two amino acid sequences each having 15 residues will have at least 60% identity when at least 9 of the amino acids at corresponding positions are the same, at least 66% identity when at least 10 of the amino acids at corresponding positions are the same, at least 73% identity when at least 11 of the amino acids at corresponding positions are the same, at least 80% identity when at least 12 of the amino acids at corresponding positions are the same, at least 86% identity when at least 13 of the amino acids at corresponding positions are the same, and at least 93% identity when at least 14 of the amino acids at corresponding positions are the same. In another example, two amino acid sequences each having 19 residues will have at least 73% identity when at least 14 of the amino acids at corresponding positions are the same, at least 78% identity when at least 15 of the amino acids at corresponding positions are the same, at least 84% identity when at least 16 of the amino acids at corresponding positions are the same, at least 89% identity when at least 17 of the amino acids at corresponding positions are the same, and at least 94% identity when at least 18 of the amino acids at corresponding positions are the same.

Similarly, two amino acid sequences each having 20 residues will have at least 95% identity when 19 of the amino acids at corresponding positions are the same, or at least 90% identity when at least 18 of the amino acids at corresponding positions are the same, or at least 85% identity when at least 17 of the amino acids at corresponding positions are the same, or at least 80% identity when at least 16 of the amino acids at corresponding positions are the same. In other non-limiting examples, two amino acid sequences each having 100 residues will have 95% identity when 95 of the amino acids at corresponding positions are the same. Two amino acid sequences each having 100 residues will have at least 90% identity when at least 90 of the amino acids at corresponding positions are the same. Further, where a sequence is described herein as having "at least X % identity to" a reference sequence, this is intended to include, unless indicated otherwise, all percentages greater than X %, such as for example, (X+1)%, (X+2)%, (X+3)%, (X+4)%, and so on, up to 100%.

The terms "polynucleotide sequence" or "nucleic acid," as used herein, include any polynucleotide sequence which encodes a peptide product including polynucleotides in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the anti-sense strand. The peptide may be expressed using polynucleotide sequence(s) which differ in codon usage due to the degeneracies of the genetic code or allelic variations.

The terms "infection," "transduction," and "transfection" are used interchangeably herein and mean introduction of a gene, nucleic acid, or polynucleotide sequence into cells such that the encoded peptide or protein is expressed. The polynucleotides which encode peptides or proteins of the present disclosure may comprise additional sequences, such as additional coding sequences within the same transcription unit, controlling elements such as promoters, ribosome binding sites, transcription terminators, polyadenylation sites, additional transcription units under control of the same or different promoters, sequences that permit cloning, expression, homologous recombination, and transformation of a host cell, and any such construct as may be desirable to provide embodiments of the present disclosure.

In certain embodiments, the present disclosure includes expression vectors capable of expressing one or more peptide molecules described herein. Expression vectors for different cell types are well known in the art and can be selected without undue experimentation. Generally, the DNA encoding the fusion polypeptide is inserted into an expression vector, such as a plasmid, in proper orientation and correct reading frame for expression. If necessary, the DNA may be linked to the appropriate transcriptional and translational regulatory control nucleotide sequences recognized by the desired host, although such controls are generally available in the expression vector. The vector is then introduced into the host through standard techniques. Guidance can be found e.g., in Sambrook et al. Molecular Cloning: A Laboratory Manual, 3d ed., Cold Spring Harbor Laboratory Press, N.Y. 2001)).

In at least certain embodiments, the peptide compounds of the present disclosure, whether synthetically or recombinantly produced, may be used as a pharmaceutical composition when combined with a pharmaceutically acceptable carrier. Such a composition may contain, in addition to the peptide and carrier, diluents, fillers, salts, buffers, stabilizers, solubilizers, and other materials well known in the art. Suitable carriers, vehicles and other components of the formulation are described, for example, in *Remington: The Science and Practice of Pharmacy*, 21$^{st}$ ed. The term "pharmaceutically acceptable" means a non-toxic material that does not interfere with the effectiveness of the biological activity of the peptides. The characteristics of the carrier will depend on the route of administration.

The pharmaceutical compositions of the present disclosure may be in the form of liposomes in which isolated peptide is combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

An effective amount of the peptide compound used in the treatment described herein can be determined by the attending diagnostician, as one skilled in the art, by the use of conventional techniques and by observing results obtained under analogous circumstances. In determining the therapeutically effective dose, a number of factors may be considered by the attending diagnostician, including, but not limited to: the species of the subject; its size, age, and general health; the specific *C. difficile* infection involved; the degree of or involvement or the severity of the *C. difficile* infection; the response of the individual subject; the particular compound administered; the mode of administration; the bioavailability characteristic of the preparation administered; the dose regimen selected; the use of concomitant medication; and other relevant circumstances. An effective amount of a compound of the present disclosure also refers to an amount of the peptide compound which is effective in controlling or reducing the *C. difficile* infection.

An effective amount of a composition of the present disclosure will generally contain sufficient active ingredient (i.e., the peptide compound) to deliver from about 0.1 µg/kg to about 100 mg/kg (weight of active ingredient/body weight of patient). Particularly, the composition will deliver at least 0.5 µg/kg to 50 mg/kg, and more particularly at least 1 µg/kg to 10 mg/kg.

Practice of the method of the present disclosure may include administering to a subject an effective amount of the peptide compound in any suitable systemic or local formulation, in an amount effective to deliver the dosages listed above. In one embodiment, an effective, particular therapeutic dosage of the peptide compound is 1 µg/kg to 10 mg/kg of the peptide. The dosage can be administered on a one-time basis, or (for example) from one to five times per day or once or twice per week, or continuously via a venous drip, depending on the desired therapeutic effect. In one therapeutic method of the present disclosure, the peptide compound is provided in an IV infusion in the range of from 1 mg/kg-10 mg/kg of body weight once a day.

In practicing the method of treatment or use of the present disclosure, an effective amount of the peptide compound is administered to a mammal having an active *C. difficile* infection. The peptide compound may be administered in accordance with the method of the present disclosure either alone or in combination with other therapies.

Administration of the peptide compound used in the pharmaceutical composition or to practice the method of the present disclosure can be carried out in a variety of conventional ways, such as, but not limited to, orally, by inhalation, rectally, or by cutaneous, subcutaneous, intraperitoneal, vaginal, or intravenous injection. Oral formulations may be formulated such that the peptide compound passes through a portion of the digestive system before being released, for example it may not be released until reaching the small intestine, or the colon.

When an effective amount of the peptide compound is administered orally, the compound may be in the form of a tablet, capsule, powder, solution or elixir. The pharmaceutical composition may additionally contain a solid carrier such as a gelatin or an adjuvant. The tablet, capsule, and powder particularly contains from about 0.05 to 95% of the peptide compound by dry weight. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition particularly contains from about 0.005 to 95% by weight of peptide. For example, a dose of 10-1000 mg once to twice a day could be administered orally.

For oral administration, the peptide compounds can be formulated into solid or liquid preparations such as capsules, pills, tablets, lozenges, melts, powders, suspensions, or emulsions. Solid unit dosage forms can be capsules of the ordinary gelatin type containing, for example, surfactants, lubricants and inert fillers such as lactose, sucrose, and cornstarch or they can be sustained release preparations.

In another embodiment, the peptide compounds of the present disclosure can be tableted with conventional tablet bases such as lactose, sucrose, and cornstarch in combination with binders, such as acacia, cornstarch, or gelatin, disintegrating agents such as potato starch or alginic acid, and a lubricant such as stearic acid or magnesium stearate. Liquid preparations are prepared by dissolving the peptide compound in an aqueous or non-aqueous pharmaceutically acceptable solvent which may also contain suspending agents, sweetening agents, flavoring agents, and preservative agents as are known in the art.

For parenteral administration, for example, the peptide compounds may be dissolved in a physiologically acceptable pharmaceutical carrier and administered as either a solution or a suspension. Illustrative of suitable pharmaceutical carriers are water, saline, dextrose solutions, fructose solutions, ethanol, or oils of animal, vegetative, or synthetic origin. The pharmaceutical carrier may also contain preservatives, and buffers as are known in the art.

When an effective amount of the peptide compound is administered by intravenous, cutaneous or subcutaneous injection, the peptide compound may be in the form of a pyrogen-free, parenterally acceptable aqueous solution or suspension. The preparation of such parenterally acceptable peptide solutions, having due regard to pH, isotonicity, stability, and the like, is within the skill in the art. A particular pharmaceutical composition for intravenous, cutaneous, or subcutaneous injection may contain, in addition to the peptide compound, an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical compositions of the present disclosure may also contain stabilizers, preservatives, buffers, antioxidants, or other additive known to those of skill in the art.

As noted above, the compositions can also include an appropriate carrier. For topical use, any of the conventional excipients may be added to formulate the peptide compound into a lotion, ointment, powder, cream, spray, or aerosol. For surgical implantation, the peptide compound may be combined with any of the well-known biodegradable and bio-erodible carriers, such as polylactic acid and collagen formulations. Such materials may be in the form of solid implants, sutures, sponges, wound dressings, and the like. In any event, for local use of the materials, the peptide compound is usually present in the carrier or excipient in a weight ratio of from about 1:1000 to 1:20,000, but is not limited to ratios within this range. Preparation of compositions for local use is detailed in *Remington: The Science and Practice of Pharmacy*, 21$^{st}$ ed.

As noted, particular amounts and modes of administration are able to be determined by one skilled in the art. One skilled in the art of preparing formulations can readily select the proper form and mode of administration depending upon the particular characteristics of the peptide compound selected, the *C. difficile* infection to be treated, the stage of the *C. difficile* infection, and other relevant circumstances using formulation technology known in the art, described, for example, in *Remington: The Science and Practice of Pharmacy*, 21$^{st}$ ed. The pharmaceutical compositions of the presently disclosed inventive concepts can be manufactured utilizing techniques known in the art. Typically the effective amount of the peptide compound will be admixed with a pharmaceutically acceptable carrier.

The amount of the peptide compound in the pharmaceutical composition of the present disclosure will depend upon the nature and severity of the condition being treated, and on the nature of prior treatments which the patient has undergone. Ultimately, the attending physician will decide the amount of peptide compound with which to treat each individual patient. Without wishing to be held to a specific dosage, it is contemplated that the various pharmaceutical compositions used to practice the method of the present disclosure may contain, but are not limited to, about 0.1 mg to about 100 mg of the peptide compound per kg body weight per dose.

The duration of an intravenous therapy using the pharmaceutical composition of the present disclosure will vary, depending on the severity of the *C. difficile* infection being treated and the condition and potential idiosyncratic response of each individual patient. In at least one embodiment, it is contemplated that the duration of each application of the peptide compound may be in the range of 1 to 4 hours and given once every 12 or 24 hours by continuous intravenous administration. Other antibiotics, intravenous fluids, cardiovascular and respiratory support could also be provided if requested by the attending physician in a manner known to one of ordinary skill in the art.

Additional pharmaceutical methods may be employed to control the duration of action of the peptide compound. Increased half-life and controlled release preparations may be achieved through the use of polymers to conjugate, complex with, or absorb the peptide described herein. The controlled delivery and/or increased half-life may be achieved by selecting appropriate macromolecules (for example, polysaccharides, polyesters, polyamino acids, homopolymers polyvinyl pyrrolidone, ethylenevinylacetate, methylcellulose, or carboxymethylcellulose, and acrylamides such as N-(2-hydroxypropyl) methacrylamide, proteins (e. g., bovine serum albumin or human serum albumin) and the appropriate concentration of macromolecules as well as the methods of incorporation, in order to control release.

Another possible method useful in controlling the duration of action by controlled release preparations and half-life is incorporation of the peptide molecule or its functional derivatives into particles of a polymeric material such as polyesters, polyamides, polyamino acids, hydrogels, poly (lactic acid), ethylene vinylacetate copolymers, copolymer micelles of, for example, PEG and poly(1-aspartamide).

It is also possible to entrap the peptide compounds in microcapsules prepared, for example, by coacervation techniques or by interfacial polymerization (for example, hydroxymethylcellulose or gelatine-microcapsules and poly-(methylmethacylate) microcapsules, respectively), in colloidal drug delivery systems (for example, liposomes, albumin microspheres, macroemulsions, nano-particles, and nanocapsules), or in macroemulsions. Such techniques are well known to persons having ordinary skill in the art.

When the peptide composition is to be used as an injectable material, it can be formulated into a conventional injectable carrier. Suitable carriers include biocompatible and pharmaceutically acceptable phosphate buffered saline solutions, which are particularly isotonic.

For reconstitution of a lyophilized product in accordance with the present disclosure, one may employ a sterile diluent, which may contain materials generally recognized for approximating physiological conditions and/or as required by governmental regulation. In this respect, the sterile diluent may contain a buffering agent to obtain a physiologically acceptable pH, such as sodium chloride, saline, phosphate-buffered saline, and/or other substances which are physiologically acceptable and/or safe for use. In general, the material for intravenous injection in humans should conform to regulations established by the Food and Drug Administration, which are available to those in the field. The pharmaceutical composition may also be in the form of an aqueous solution containing many of the same substances as described above for the reconstitution of a lyophilized product.

The peptide compounds of the present disclosure can also be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

As mentioned above, the peptide compounds of the present disclosure may be incorporated into pharmaceutical preparations which may be used for therapeutic purposes. However, the term "pharmaceutical preparation" is intended in a broader sense herein to include preparations containing a peptide composition in accordance with present disclosure, used not only for therapeutic purposes but also for reagent or diagnostic purposes as known in the art. The pharmaceutical preparation intended for therapeutic use should contain a "pharmaceutically acceptable" or "effective amount" of the peptide compound, i.e., that amount necessary for a therapeutic response in a patient or subject in need of such treatment. If the pharmaceutical preparation is to be employed as a reagent or diagnostic, then it should contain reagent or diagnostic amounts of the peptide compound.

In certain embodiments the peptides and peptide conjugates of the present disclosure can be used as vaccines to elicit an antibody response against a TcdB toxin. The optimum amount of each one or more peptide compound to be included in the vaccine and the optimum dosing regimen can be determined by one skilled in the art without undue experimentation. For example, the peptide or its variant may be prepared for intravenous (i.v.) injection, sub-cutaneous (s.c.) injection, intradermal (i.d.) injection, intraperitoneal (i.p.) injection, or intramuscular (i.m.) injection. The peptides may be substantially pure, or combined with one or more immune-stimulating adjuvants (as discussed elsewhere herein) or used in combination with immune-stimulatory cytokines, or be administered with a suitable delivery system, for example liposomes. Adjuvants are substances that non-specifically enhance or potentiate the immune response (e.g., immune responses mediated by CTLs and helper-T (TH) cells to an antigen, and would thus be considered useful in the composition of the present disclosure when used as a vaccine. Suitable adjuvants include, but are not limited to 1018 ISS, aluminium salts such as but not limited to alum (potassium aluminum sulfate), aluminum hydroxide, aluminum phosphate, or aluminum sulfate, Amplivax, AS15, BCG, CP-870,893, CpG7909, CyaA, Mologen's dSLIM, GM-CSF, IC30, IC31, Imiquimod, ImuFact IMP321, interferon-alpha or -beta, IS Patch, ISS, ISCOMs, JuvImmune, LipoVac, MF59, monophosphoryl lipid A, and other non-toxic LPS derivatives, Montanide IMS 1312, Montanide ISA 206, Montanide ISA 50\1, Montanide ISA-51, OK-432, and OM-174. Other pharmaceutically suitable adjuvants include nontoxic lipid A-related adjuvants such as, by way of non-limiting example, nontoxic monophosphoryllipid A (see, e.g., Persing et al., Trends Microbial. 10:s32-s37 (2002)), for example, 3 De-0-acylated monophosphoryllipid A (MPL) (see, e.g., United Kingdom Patent Application No. GB 2220211). Other useful adjuvants include QS21 and QuilA that comprise a triterpene glycoside or saponin isolated from the bark of the *Quillaja saponaria* Molina tree found in South America (U.S. Pat. No. 5,057,540). Other suitable adjuvants include polymeric or monomeric amino acids such as polyglutamic acid or polylysine, liposomes, and CpG (U.S. Pat. No. 7,402,572). Other examples of adjuvants that may be used in the compositions disclosed herein include but are not limited to those disclosed in U.S. Pat. No. 8,895,514.

Cytotoxic T-cells (CTLs) recognize an antigen in the form of a peptide bound to an MHC molecule (e.g., class I or II) rather than the intact foreign antigen itself. The MHC molecule itself is located at the cell surface of an antigen presenting cell (APC). Thus, an activation of CTLs is only possible if a trimeric complex of peptide antigen, MHC molecule, and APC is present. Correspondingly, certain embodiments of the present disclosure include compositions including APCs having the peptides displayed thereon via MHC molecules.

In other embodiments, the composition may include sugars, sugar alcohols, amino acids such as glycine, arginine, glutamic acid and others as framework former. The sugars may be mono-, di- or trisaccharides. These sugars may be used alone, as well as in combination with sugar alcohols. Examples of sugars include glucose, mannose, galactose, fructose or sorbose as monosaccharides, saccharose, lactose, maltose or trehalose as disaccharides and raffinose as a trisaccharide. A sugar alcohol may be, for example, mannitol and/or sorbitol. Furthermore, the compositions may include physiological well tolerated excipients such as antioxidants like ascorbic acid or glutathione, preserving agents such as phenol, m-cresol, methylparaben, propylparaben, chlorobutanol, thiomersal (thimerosal) or benzalkoniumchloride, and solubilizers such as polyethyleneglycols (PEGs), e.g., PEG 3000, 3350, 4000 or 6000, or c yclodextrins, e.g., hydroxypropyl-cyclodextrin, sulfobutylethyl-cyclodextrin or γ-cyclodextrin, or dextrans or poloxamers, e.g., poloxamer 407, poloxamer 188, Tween 20 or Tween 80.

In other embodiments, the present disclosure includes a kit comprising (a) a container that contains one or more pharmaceutical peptide compositions as described herein, in solution or in lyophilized form; (b) optionally, a second container containing a diluent or reconstituting solution for the lyophilized formulation; and (c) optionally, instructions for (i) use of the solution or (ii) reconstitution and/or use of the lyophilized formulation. The kit may further comprise one or more of (iii) a buffer, (iv) a diluent, (v) a filter, (vi) a needle, or (v) a syringe. The container is (in a particular, non-limiting embodiment) a bottle, a vial, a syringe or test tube; and it may be a multi-use container. The container may be formed from a variety of materials such as glass or plastic. The kit and/or container may contain instructions on or associated with the container that indicates directions for reconstitution and/or use. For example, the label may indicate that the lyophilized formulation is to be reconstituted to peptide concentrations as described above. The label may further indicate that the formulation is useful or intended for subcutaneous or intramuscular administration. The container holding the formulation may be a multi-use vial, which allows for repeat administrations (e.g., from 2-6 administrations) of the reconstituted formulation. The kit may further comprise a second container comprising a suitable diluent (e.g., sodium bicarbonate solution). The kit may further include other materials desirable from a commercial and user standpoint, including other buffers, diluents, filters, needles, syringes, and package inserts with instructions for use.

An antibody that specifically binds to an immunogenic peptide (and to a fusion polypeptide, dimeric peptide, full length or mature protein, or bacteria expressing the protein) may belong to any immunoglobulin class, for example IgG, IgE, IgM, IgD, or IgA. For characterizing the immunogenic peptides and immunogenic fusion polypeptides constructed with the peptides described herein, use of polyclonal and/or monoclonal antibodies may be desired. The antibody may be obtained from or derived from an animal, for example, fowl (e.g., chicken) and mammals, which include but are not limited to a mouse, rat, chinchilla, hamster, rabbit, or other rodent, a cow, horse, sheep, goat, camel, human, or other primate. As described herein, polyclonal antisera are obtained from an animal by immunizing the animal with an immunogenic composition comprising an immunogenic peptide, plurality of immunogenic peptides or a fusion polypeptide or plurality of fusion polypeptides.

The level to which antibodies bind to an immunogenic peptide or fusion polypeptide as described herein can be readily determined using any one or more immunoassays that are routinely practiced by persons having ordinary skill in the art. By way of non-limiting example, immunoassays include ELISA, immunoblot, radioimmunoassay, immunohistochemistry, and fluorescence activated cell sorting (FACS).

Non-human animals that may be immunized with any one of the immunogenic peptides, or fusion polypeptides, or immunogenic compositions comprising the same include by way of non-limiting example, mice, rats, rabbits, hamsters, ferrets, dogs, cats, camels, sheep, cattle, pigs, horses, goats, chickens, llamas, and non-human primates (e.g., cynomolgus macaque, chimpanzee, rhesus monkeys, orangutan, and baboon). Adjuvants typically used for immunization of non-human animals include but are not limited to Freund's complete adjuvant, Freund's incomplete adjuvant, montanide ISA, Ribi Adjuvant System (RAS) (GlaxoSmithKline, Hamilton, Mont.), and nitrocellulose-adsorbed antigen. In general, after the first injection, a subject receives one or more booster immunizations according to a particular (but non-limiting) schedule that may vary according to, inter alia, the immunogen, the adjuvant (if any) and/or the particular subject species. In animal subjects, the immune response may be monitored by periodically bleeding the animal, separating the sera from the collected blood, and analyzing the sera in an immunoassay, such as an ELISA assay, to determine the specific antibody titer. When an adequate antibody titer is established, the animal subject may be bled periodically to accumulate the polyclonal antisera. Polyclonal antibodies that bind specifically to the immunogen may then be purified from immune antisera, for example, by affinity chromatography using protein A or protein G immobilized on a suitable solid support, as understood by persons having ordinary skill in the art. Affinity chromatography may be performed wherein an antibody specific for an Ig constant region of the particular immunized animal subject is immobilized on a suitable solid support. Affinity chromatography may also incorporate use of one or more immunogenic peptides, or fusion proteins, which may be useful for separating polyclonal antibodies by their binding activity to a particular immunogenic peptide. Monoclonal antibodies that specifically bind to an immunogenic peptide and/or fusion protein and immortal eukaryotic cell lines (e.g., hybridomas) that produce monoclonal antibodies having the desired binding specificity, may also be prepared, for example, using the technique of Kohler and Milstein ((Nature, 256:495-97 (1976), Eur. J. Immunol. 6:511-19 (1975)) and improvements thereto.

The immunogenic compositions described herein may be formulated by combining a plurality of immunogenic peptides and/or a plurality of fusion polypeptides and/or carrier molecule-linked immunogenic peptides with at least one pharmaceutically acceptable excipient. As described herein the immunogenic compositions may further comprise a pharmaceutically suitable adjuvant. Typically, all immunogenic peptides or all fusion polypeptides intended to be administered to a subject are combined in a single immunogenic composition, which may include at least one pharmaceutically acceptable excipient and which may further include at least one pharmaceutically suitable adjuvant. Alternatively, for example, multiple immunogenic compositions may be formulated separately for separate administration, which could be by any route described herein or in the art and which could be sequential or concurrent.

The immunogenic compositions described herein may be formulated as sterile aqueous or non-aqueous solutions, suspensions or emulsions, which as described herein may additionally comprise a physiologically acceptable excipient (which may also be called carrier) and/or a diluent. The immunogenic compositions may be in the form of a solid, liquid, or gas (aerosol). Alternatively, immunogenic compositions described herein may be formulate d as a lyophilate (i.e., a lyophilized composition), or may be encapsulated within liposomes using technology well known in the art. As noted elsewhere herein, the immunogenic compositions may also contain other components, which may be biologically active or inactive. Such components include, but are not limited to, buffers (e.g., neutral buffered saline or phosphate buffered saline), carbohydrates (e.g., glucose, mannose, sucrose or dextrans), mannitol, proteins (such as albumin), polypeptides or amino acids such as glycine, antioxidants, chelating agents such as EDTA or glutathione, stabilizers, dyes, flavoring agents, and suspending agents and/or preservatives. In general, as discussed herein, the type of excipient is selected on the basis of the mode of administration. The compositions and preparations described herein may be formulated for any appropriate manner of administration, including, for example, topical, buccal, lingual, oral, intranasal, intrathecal, rectal, vaginal, intraocular, subconjunctival, transdermal, sublingual or parenteral administration.

Vaccine dosage size may generally be determined in accordance with accepted practices in the art. The dose may depend upon the body mass, weight, or blood volume of the subject being treated. In general, the amount of an immunogenic peptide or peptides, or fusion polypeptide, or carrier molecule composition as described herein that is present in a dose, is in a range of, for example (but not limited to), about 1 µg to about 100 mg, from about 10 µg to 50 mg, from about 50 µg to 10 mg comprising an appropriate dose) for a 5-50 k g subject. Booster immunizations may be administered multiple times (e.g., two times or three times or four times or more), at desired time intervals ranging from, for example, about 2 weeks to about 26 weeks, such as 2, 4, 8, 12, 16, or 26 week intervals. The time intervals between different doses (e.g., between the primary dose and second dose, or between the second dose and a third dose) may not be the same, and the time interval between each two doses may be determined independently. Non-limiting embodiments of therapeutically effective amounts of peptides or fusion polypeptides of the presently disclosed inventive concepts will generally contain sufficient active substance to deliver from about 0.1 µg/kg to about 100 mg/kg (weight of active substance/body weight of the subject). Particularly, the composition will deliver about 0.5 µg/kg to about 50 mg/kg, and more particularly about 1 µg/kg to about 10 mg/kg.

Peptides of the present disclosure include, but are not limited to, amino acid sequences which include the 11-amino acid sequence NVFKGNTISDK (SEQ ID NO:1) and which have inhibitory activity against a TcdB toxin (anti-TcdB activity) and/or cell penetrating activity. In at least certain embodiments the peptides of the present disclosure comprise or consist of 15-100 amino acids, and more particularly 15-50 amino acids (e.g., 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids), including SEQ ID NO: 1 or variants thereof. In the peptides which include SEQ ID NO:1 or variants thereof and comprise 15 or more amino acids, the additional 4 or more amino acids (up to, for example 89, additional amino acids) may extend from the N-terminal and/or C-terminal end of the amino acid sequence SEQ ID NO: 1. The 4 to 89 additional amino acids that may be included in the larger peptide which contains SEQ ID NO:1 (or a variant thereof) may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val, wherein the larger peptide has anti-TcdB activity. In certain embodiments, the peptides of the present disclosure include variants of SEQ ID NO:1 which may include substitutions, such as conservative substitutions, or any amino acid in a D or L configuration (such as listed above), wherein the variant peptide has anti-TcdB activity and/or cell penetrating activity. Examples of substitutions include but are not limited to those described elsewhere herein. The NVFKGNTISDK amino acid sequence may be an N-terminal portion or a C-terminal portion of the larger peptide, or may comprise an internal portion of the larger peptide. In certain embodiments the portion of the variant peptides which corresponds to SEQ ID NO:1 has at least 60% or greater sequence identity (as defined elsewhere herein) with SEQ ID NO:1.

In at least certain embodiments, the anti-TcdB peptides of the present disclosure which include SEQ ID NO:1 (or variants thereof) comprise at least 6 additional amino acids which extend (in either direction) from the NVFKGN-TISDK amino acid sequence. For example, in at least one embodiment, the peptide comprises 6 or more additional amino acids extending from the N-terminal or the C-terminal end of SEQ ID NO:1, and no additional amino acids extending from the other end. In at least one embodiment, the peptide comprises 1 or more additional amino acids extending from the N-terminal or the C-terminal end of SEQ ID NO:1, and 5 or more additional amino acids extending from the other end of SEQ ID NO:1. In at least one embodiment, the peptide comprises 2 or more additional amino acids extending from the N-terminal or the C-terminal end of SEQ ID NO:1, and 4 or more additional amino acids extending from the other end of SEQ ID NO: 1. In at least one embodiment, the peptide comprises 3 or more additional amino acids extending from the N-terminal or the C-terminal end of SEQ ID NO:1, and 3 or more additional amino acids extending from the other end of SEQ ID NO:1.

Peptides of the present disclosure also include, but are not limited to, amino acid sequences which include the 19-amino acid sequence NVFKGNTISDKISFNFSDK (SEQ ID NO:6, also referred to herein as peptide PepB2) and which have anti-TcdB activity and/or cell penetrating activity. In at least certain embodiments the peptides of the present disclosure comprise or consist of 20-100 amino acids, and more particularly 20-50 amino acids (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids), including SEQ ID NO: 6 or variants thereof. In the peptides which include SEQ ID NO:6 or variants thereof and comprise 20 or more amino acids, the additional 1 or more amino acids (up to, for example 81, additional amino acids) may extend from the N-terminal and/or C-terminal end of the amino acid sequence SEQ ID NO:6. The 1 to 81 additional amino acids that may be included in the larger peptide which contains SEQ ID NO:6 (or a variant thereof) may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val, wherein the larger peptide has anti-TcdB activity. In certain embodiments, the peptides of the present disclosure include variants of SEQ ID NO:6 which may include substitutions, such as conservative substitutions, or any amino acid in a D or L configuration (such as listed above), wherein the variant peptide has anti-TcdB activity and/or cell penetrating activity. Examples of substitutions include but are not limited to those described elsewhere herein. The NVFKGNTISDK-ISFNFSDK amino acid sequence may be an N-terminal portion or a C-terminal portion of the larger peptide, or may comprise an internal portion of the larger peptide. In certain embodiments the portion of the variant peptides which corresponds to SEQ ID NO:6 has at least 60% or greater sequence identity (as defined elsewhere herein) with SEQ ID NO:6. In certain embodiments, the present disclosure includes truncated versions of the peptides based on SEQ ID NO:6 or the variants thereof, including for example, peptides with truncations of one, two, or three of the N-terminal amino acid residues (e.g., wherein one or more of positions 1, 2, or 3 are deleted), and/or of one, two, or three of the C-terminal amino acid residues (i.e., wherein one or more of positions 17, 18, or 19 are deleted).

Peptides of the present disclosure also include, but are not limited to, amino acid sequences which include the 19-amino acid sequence SQVKIRFTNVFKGNTISDK (SEQ ID NO:4) and which have anti-TcdB activity and/or cell penetrating activity. In at least certain embodiments the peptides of the present disclosure comprise or consist of 20-100 amino acids, and more particularly 20-50 amino acids (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids), including SEQ ID NO: 4 or variants thereof. In the peptides which include SEQ ID NO:4 or variants thereof and comprise 20 or more amino acids, the additional 1 or more amino acids (up to, for example 81, additional amino acids) may extend from the N-terminal and/or C-terminal end of the amino acid sequence SEQ ID NO:4. The 1 to 81 additional amino acids that may be included in the larger peptide which contains SEQ ID NO:4 (or a variant thereof) may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val, wherein the larger peptide has anti-TcdB activity. In certain embodiments, the peptides of the present disclosure include variants of SEQ ID NO:4 which may include substitutions, such as conservative substitutions, or any amino acid in a D or L configuration (such as listed above), wherein the variant peptide has anti-TcdB activity and/or cell penetrating activity. Examples of substitutions include but are not limited to those described elsewhere herein. The SQVKIRFTNVFKGNTISDK amino acid sequence may be an N-terminal portion or a C-terminal portion of the larger peptide, or may comprise an internal portion of the larger peptide. In certain embodiments the portion of the variant peptides which corresponds to SEQ ID NO:4 has at least 60% or greater sequence identity (as defined elsewhere herein) with SEQ ID NO:4. In certain embodiments, the present disclosure includes truncated versions of the peptides based on SEQ ID NO:4 or the variants thereof, including for example, peptides with truncations of one, two, or three of the N-terminal amino acid residues (e.g., wherein one or more of positions 1, 2, or 3 are deleted), and/or of one, two, or three of the C-terminal amino acid residues (i.e., wherein one or more of positions 17, 18, or 19 are deleted).

Peptides of the present disclosure also include, but are not limited to, amino acid sequences which include the 17-amino acid sequence RFTNVFKGNTISDKISF (SEQ ID NO:5) and which have anti-TcdB activity and/or cell penetrating activity. In at least certain embodiments the peptides of the present disclosure comprise or consist of 18-100 amino acids, and more particularly 20-50 amino acids (e.g., 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids), including SEQ ID NO: 5 or variants thereof. In the peptides which include SEQ ID NO:5 or variants thereof and comprise 18 or more amino acids, the additional 1 or more amino acids (up to, for example 83, additional amino acids) may extend from the N-terminal and/or C-terminal end of the amino acid sequence SEQ ID NO:5. The 1 to 83 additional amino acids that may be included in the larger peptide which contains SEQ ID NO:5 (or a variant thereof) may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val, wherein the larger peptide has anti-TcdB activity. In certain embodiments, the peptides of the present disclosure include variants of SEQ ID NO:5 which may include substitutions, such as conservative substitutions, or any amino acid in a D or L configuration (such as listed above), wherein the variant peptide has anti-TcdB activity and/or cell penetrating activity. Examples of substitutions include but are not limited to those described elsewhere herein. The RFTNVFKGNTISDKISF amino acid sequence may be an N-terminal portion or a C-terminal portion of the larger peptide, or may comprise an internal portion of the larger peptide. In certain embodiments the portion of the variant peptides which corresponds to SEQ ID NO:5 has at least 60% or greater sequence identity (as defined elsewhere herein) with SEQ ID NO:5. In certain embodiments, the present disclosure includes truncated versions of the peptides based on SEQ ID NO:5 or the variants thereof, including for example, peptides with truncations of one, two, or three of the N-terminal amino acid residues (e.g., wherein one or more of positions 1, 2, or 3 are deleted), and/or of one, two, or three of the C-terminal amino acid residues (i.e., wherein one or more of positions 15, 16, or 17 are deleted).

Peptides of the present disclosure also include, but are not limited to, amino acid sequences which include the 19-amino acid sequence SNKNFSGIVFTNFDIDKSK (SEQ ID NO:40) and which have anti-TcdB activity and/or cell penetrating activity. In at least certain embodiments the peptides of the present disclosure comprise or consist of 20-100 amino acids, and more particularly 20-50 amino acids (e.g., 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids), including SEQ ID NO: 40 or variants thereof. In the peptides which include SEQ ID NO:40 or variants thereof and comprise 20 or more amino acids, the additional 1 or more amino acids (up to, for example 81, additional amino acids) may extend from the N-terminal and/or C-terminal end of the amino acid sequence SEQ ID NO:40. The 1 to 81 additional amino acids that may be included in the larger peptide which contains SEQ ID NO:40 (or a variant thereof) may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val, wherein the larger peptide has anti-TcdB activity. In certain embodiments, the peptides of the present disclosure include variants of SEQ ID NO:40 which may include substitutions, such as conservative substitutions, or any amino acid in a D or L configuration (such as listed above), wherein the variant peptide has anti-TcdB activity and/or cell penetrating activity. Examples of substitutions include but are not limited to those described elsewhere herein. The SNKNFSGIVFTNFDIDKSK amino acid sequence may be an N-terminal portion or a C-terminal portion of the larger peptide, or may comprise an internal portion of the larger peptide. In certain embodiments the portion of the variant peptides which corresponds to SEQ ID NO:40 has at least 60% or greater sequence identity (as defined elsewhere herein) with SEQ ID NO:40. In certain embodiments, the present disclosure includes truncated versions of the peptides based on SEQ ID NO:40 or the variants thereof, including for example, peptides with truncations of one, two, or three of the N-terminal amino acid residues (e.g., wherein one or more of positions 1, 2, or 3 are deleted), and/or of one, two, or three of the C-terminal amino acid residues (i.e., wherein one or more of positions 17, 18, or 19 are deleted).

Peptides of the present disclosure also include, but are not limited to, amino acid sequences which include the 22-amino acid sequence SFNKMSIDFKDIKKLSLGYIMS (SEQ ID NO:49) and which have anti-TcdB activity and/or cell penetrating activity. In at least certain embodiments the peptides of the present disclosure comprise or consist of 23-100 amino acids, and more particularly 23-50 amino acids (e.g., 23, 24, 25, 26, 27, 28, 29, 30, 31, 32, 33, 34, 35, 36, 37, 38, 39, 40, 41, 42, 43, 44, 45, 46, 47, 48, 49, or 50 amino acids), including SEQ ID NO: 49 or variants thereof. In the peptides which include SEQ ID NO:49 or variants thereof and comprise 23 or more amino acids, the additional 1 or more amino acids (up to, for example 78, additional amino acids) may extend from the N-terminal and/or C-terminal end of the amino acid sequence SEQ ID NO:49. The 1 to 78 additional amino acids that may be included in the larger peptide which contains SEQ ID NO:49 (or a variant thereof) may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, LtThr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val, wherein the larger peptide has anti-TcdB activity. In certain embodiments, the peptides of the present disclosure include variants of SEQ ID NO:49 which may include substitutions, such as conservative substitutions, or any amino acid in a D or L configuration (such as listed above), wherein the variant peptide has anti-TcdB activity and/or cell penetrating activity. Examples of substitutions include but are not limited to those described elsewhere herein. The SFNKMSIDFKDIKKLSLGYIMS amino acid sequence may be an N-terminal portion or a C-terminal portion of the larger peptide, or may comprise an internal portion of the larger peptide. In certain embodiments the portion of the variant peptides which corresponds to SEQ ID NO:49 has at least 60% or greater sequence identity (as defined elsewhere herein) with SEQ ID NO:49. In certain embodiments, the present disclosure includes truncated versions of the peptides based on SEQ ID NO:49 or the variants thereof, including for example, peptides with truncations of one, two, three, or four of the N-terminal amino acid residues (e.g., wherein one or more of positions 1, 2, 3, or 4 are deleted), and/or of one, two, three, or four of the C-terminal amino acid residues (i.e., wherein one or more of positions 19, 20, 21, or 22 are deleted).

Peptides of the present disclosure also include, but are not limited to, amino acid sequences which include the 21-amino acid sequence KPPIKNLITGFTTIGDDKYYF (SEQ ID NO:10) and which have anti-TcdB activity and/or cell penetrating activity. In at least certain embodiments the peptides of the present disclosure comprise or consist of 22-100 amino acids, and more particularly 22-50 amino acids (e.g., 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acids), including SEQ ID NO: 10 or variants thereof. In the peptides which include SEQ ID NO:10 or variants thereof and comprise 22 or more amino acids, the additional 1 or more amino acids (up to, for example 79, additional amino acids) may extend from the N-terminal and/or C-terminal end of the amino acid sequence SEQ ID NO:10. The 1 to 79 additional amino acids that may be included in the larger peptide which contains SEQ ID NO:10 (or a variant thereof) may be selected from, but are not limited to, the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val, wherein the larger peptide has anti-TcdB activity. In certain embodiments, the peptides of the present disclosure include variants of SEQ ID NO:10 which may include substitutions, such as conservative substitutions, or any amino acid in a D or L configuration (such as listed above), wherein the variant peptide has anti-TcdB activity and/or cell penetrating activity. Examples of substitutions include but are not limited to those described elsewhere herein. The SFNKMSIDFKDIKKLSLGYIMS amino acid sequence may be an N-terminal portion or a C-terminal portion of the larger peptide, or may comprise an internal portion of the larger peptide. In certain embodiments the portion of the variant peptides which corresponds to SEQ ID NO:10 has at least 60% or greater sequence identity (as defined elsewhere herein) with SEQ ID NO:10. In certain embodiments, the present disclosure includes truncated versions of the peptides based on SEQ ID NO:10 or the variants thereof, including for example, peptides with truncations of one, two, three, or four of the N-terminal amino acid residues (e.g., wherein one or more of positions 1, 2, 3, or 4 are deleted), and/or of one, two, three, or four of the C-terminal amino acid residues (i.e., wherein one or more of positions 18, 19, 20, or 21 are deleted).

In at least one embodiment, the present disclosure is directed to a peptide comprising an amino acid sequence $X_1 X_2 X_3 X_4 X_5 X_6 X_7 X_8 X_9 X_{10} X_{11}$ (SEQ ID NO:67), wherein each of $X_1$, $X_2$, $X_3$, $X_4$, $X_7$, $X_8$, $X_9$, $X_{10}$, and $X_{11}$ is independently selected from the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val; $X_5$ is selected from the group consisting of gly, L-ala, L-ser, D-ala, and D-ser; $X_6$ is selected from the group consisting of L-asn, L-asp, L-gln, L-his, L-ser, L-thr, D-asn, D-asp, D-gln, D-his, D-ser, and D-thr; and wherein the peptide has anti-TcdB activity and/or cell penetrating activity. $X_3$ may be selected from the group consisting of L-phe, L-met, L-leu, L-ile, D-phe, D-met, d-leu, and D-ile. $X_5$ may be gly and $X_6$ may be asn. The peptide may have a length of from 15 to 50 to 100 amino acids (inclusive). For example, in certain embodiments, the peptide comprises 2, 3, 4, 5, 6, 7, 8, 9, 10, 11, or 12 amino acids extending from the N-terminal and/or C-terminal ends of SEQ ID. NO:67. The portion of the peptide comprising SEQ ID NO:67 may have from 63% identity up to 100% identity with SEQ ID NO: 1. In certain embodiments the peptide and a pharmaceutically-acceptable carrier together comprise a pharmaceutical composition.

In other non-limiting embodiments, PepB2-type TcdB Inhibitors and/or cell penetrating peptides of the present disclosure include, but are not limited to, peptides comprising or having an amino acid sequence: $X_1 X_2 X_3 X_4 X_5 X_6 X_7 X_8 X_9 X_{10} X_{11} X_{12} X_{13} X_{14} X_{15} X_{16} X_{17} X_{18} X_{19}$ (SEQ ID NO:68), wherein each of $X_1$, $X_2$, $X_3$, $X_4$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, and $X_{19}$ is independently selected from the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val; $X_5$ is selected from the group consisting of gly, L-ala, L-ser, D-ala, and D-ser; and $X_6$ is selected from the group consisting of L-asn, L-asp, L-gln, L-his, L-ser, L-thr, D-asn, D-asp, D-gln, D-his, D-ser, and D-thr; and wherein the peptide has anti-TcdB activity and/or cell penetrating activity. In certain embodiments $X_3$ may be selected from the group consisting of L-phe, L-met, L-leu, L-ile, D-phe, D-met, d-leu, and D-ile. In certain embodiments $X_5$ and $X_6$ and may be gly and asn (D or L), respectively. The peptide may have a length of from 20 to 50 to 100 amino acids (inclusive). For example, in certain embodiments, the peptide comprises 2, 3, 4, 5, 6, 7, 8, 9, 10, 11, or 12 amino acids extending from the N-terminal and/or C-terminal ends of SEQ ID. NO:68. The portion of the peptide comprising SEQ ID NO:68 may have from 63% identity up to 100% identity with SEQ ID NO: 6. In certain embodiments the peptide and a pharmaceutically-acceptable carrier together comprise a pharmaceutical composition.

Other amino acid motifs which could substitute for the GN motif in SEQ ID NOS:1, 6, 67, and 68 to form a beta-turn include, but are not limited to, PDG, SDG, LDG, RDG, LTG, SDN, RDN, and PDN, or any two-residue or three-residue amino acid sequence which forms a beta-turn in the peptide. Therefore, in certain embodiments, SEQ ID NO:1, and thus the peptides disclosed herein which comprise SEQ ID NO:1, could be substituted with a 12 amino acid sequence which is identical to SEQ ID NO:1 (including potential substitutions listed above) except wherein $G_5N_6$ is replaced with one of PDG, SDG, LDG, RDG, LTG, SDN, RDN, or PDN, or with any two-residue or three-residue amino acid sequence which forms a beta-turn in the peptide. Further, in certain embodiments, SEQ ID NO:6, and thus the peptides disclosed herein which comprise SEQ ID NO:6, could be substituted with a 20 amino acid sequence which is identical to SEQ ID NO:6 (including potential substitutions listed above) except wherein $G_5N_6$ is replaced with one of PDG, SDG, LDG, RDG, LTG, SDN, RDN, or PDN, or with any two-residue or three-residue amino acid sequence which forms a beta-turn in the peptide. Further, in certain embodiments, $X_5X_6$ of SEQ ID NO:67 can be replaced with (1) a sequence $X_5X_6X_{6a}$, wherein $X_5X_6X_{6a}$ is PDG, SDG, LDG, RDG, LTG, SDN, RDN, or PDN, or (2) any two-residue or three-residue amino acid sequence which forms a beta-turn in the peptide. Further, in certain embodiments, $X_5X_6$ of SEQ ID NO:68 can be replaced with (1) a sequence $X_5X_6X_{6a}$, wherein $X_5X_6X_{6a}$ is PDG, SDG, LDG, RDG, LTG, SDN, RDN, or PDN, or (2) any two-residue or three-residue amino acid sequence which forms a beta-turn in the peptide.

Various embodiments of the present disclosure will be more readily understood by reference to the following examples and description, which as noted above are included merely for purposes of illustration of certain aspects and embodiments of the present disclosure, and are not intended to be limiting. The following detailed examples and methods describe how to make and use various peptides, peptide conjugates, and other peptide compositions of the present disclosure and are to be construed, as noted above, only as illustrative, and not limitations of the disclosure in any way whatsoever. Those skilled in the art will promptly recognize appropriate variations from the materials and procedures described herein.

EXPERIMENTAL

TcdB toxin is a major virulence factor that contributes to many of the pathologies in *C. difficile* infection. The TcdB toxin is a 2366 amino acid protein that binds to cell surface receptors (CSPG4, PVRL3), undergoes endocytosis, translocates into the cytosol following autoprocessing, and glucosylates small GTPases within the cell. Each of these intoxication activities are ascribed to specific sequences within TcdB and each activity can be recapitulated with fragments of the toxin. Small-angle X-ray scattering, electron microscopy, and biochemical analyses indicate TcdB is organized into 4 domains, with an amino-terminal glucosylation domain (amino acid positions 1-543), a cysteine-protease domain (positions 544-801), a cell-entry/translocation domain (positions 801-1650), and a carboxyl-terminal cell-binding domain (positions 1651-2366).

In the present work, TcdB toxicity was inhibited by targeting a region of the protein found to be important for structural stability. Preliminary results indicated that amino acids 1753-1851 of the TcdB2 variant form of TcdB ($TcdB2_{1753-1851}$) influence structural integrity. Further work was conducted to investigate if peptides derived from this region could disrupt intramolecular interactions and inactivate TcdB. We screened a panel of synthetic peptides based on $TcdB2_{1753-1851}$ and identified peptides that inactivated both TcdB2 and the related TcdB1 toxin protein. These data are described below.

Methods

Toxins and Peptides

Peptides used in the present work were synthesized and purified to 90% purity by GenScript (Piscataway, N.J.). Peptide quality was assessed by HPLC and MS. As noted, recombinant TcdB1 and TcdB2 were produced in a *Bacillus megaterium* system (MoBiTec, Göttingen, Germany). *B. megaterium* was transformed with pC-His1622-TcdB1 (gift from B. Lacy) or pC-His1622-TcdB2 following the instructions provided by the manufacturer (MoBiTec, Göttingen, Germany). Transformed *B. megaterium* was then grown at 37° C. in LB medium supplemented with 10 μg/ml tetracycline. After reaching an $A_{600}$ of 0.3, the culture was induced with 0.5% D-xylose for 5 h. Following induction, *B. megaterium* was isolated by centrifugation, and pellets were suspended in 20 mM HEPES (pH 8.0), 500 mM NaCl, and 20 mM imidazole. Next, the cells were lysed, and $Ni^{2+}$ affinity chromatography was used to purify TcdB to approximately 90% as determined by SDS-PAGE. The GTD-encoding region of the tcdb gene (nucleotides 1-1629; amino acids 1-543) from TcdB1 (codon-optimized for *Escherichia coli*) was cloned into the pDest15 vector. The pDest15 vector allowed for the expression of the $GTD_{TcdB1}$ with an amino-terminal GST tag in *E. coli*. After this plasmid was transformed into *E. coli* (BL21 star DE3), the cultures were grown to an $A_{600}$ of 0.8 and induced with 300 μM isopropyl 1-thio-β-D-galactopyranoside for 16 h at 16° C. GST-tagged $GTD_{TcdB1}$ was then purified by affinity chromatography to approximately 90% purity as assessed by SDS-PAGE. Conjugation of PepB2 to BSA was performed by GenScript (Piscataway, N.J.) and is described in more detail below.

Assays

Cell based assays and experiments were performed using one or more cell rounding assays, cell viability assays, transepithelial electrical resistance assays, flow cytometry analyses, and confocal microscopy, as described in detail below.

Cell Rounding Assay

CHO-K1 cells were cultured at 37° C. in the presence of 6% $CO_2$ with F12-K containing 10% FBS, 100 units/ml penicillin, and 100 μg/ml streptomycin. These cells were seeded in 24-well plates at a density of $5.0\times10^4$ cells/well and allowed to attach overnight. On the next day, TcdB in the presence and absence of PepB2 was added to complete culture media and then added to cells. The cells were incubated with the toxin or toxin/peptide mixture for 2 h, and then fixed for 10 min with PBS containing 4% formaldehyde. The fixed cells were then imaged and non-rounded and rounded cells were counted. For each data point, approximately 200 cells were counted from 6 fields taken from 2 separate wells.

Cytotoxicity Assay

These assays use the ability of TcdB or TcdA proteins to reduce CHO-K1 cell (ATCC) viability as a method to quantify toxin activity over a range of concentrations. In these experiments, CHO-K1 cells were cultured at 37° C. in the presence of 6% $CO_2$ with F12-K containing 10% FBS, 100 units/ml penicillin, and 100 μg/ml streptomycin. Prior to these assays, CHO-K1 cells were seeded in 96-well plates at a density of $1.0\times10^4$ cells/well and allowed to attach overnight. Next, TcdA or TcdB in the presence and absence of peptide was added to complete culture media and then added to cells. For the experiments with *Bacillus anthracis* LT, RAW 264.7 cells were grown in DMEM (ATCC) containing 10% fetal bovine serum (ATCC) and then seeded in 96-well plates at a density of $2.0\times10^4$ cells/well. The cells were allowed to attach overnight and then exposed to LT (protective antigen and lethal factor) with and without peptide. For all these cytotoxicity assays, cells were incubated with the toxin or toxin/peptide mixture for 24 h, and then cell viability was measured by the CCK-8 assay (Sigma), a WST-8 dye-based colorimetric reaction.

Transepithelial Electrical Resistance (TER)

TER was measured in a human carcinoma cell line (T84; ATCC). T84 cells were cultured in media consisting of a 1:1 mixture of F12-K (ATCC) and DMEM (ATCC; modified with 4 mM L-glutamine, 4500 mg/L glucose, 1 mM sodium pyruvate, and 1500 mg/L sodium bicarbonate). This 1:1 mixture of culture media also included 5% FBS, 100 units/ml penicillin, and 100 μg/ml streptomycin. T84 cells were seeded at a density of $6.0\times10^4$ cells/well in a transwell plate with a growth area of 0.3 $cm^2$ and a membrane composed of tissue culture treated polyethylene terephthalate with a pore size of 3 μm. These cells were cultured until tight junctions formed (about 1 week) and then exposed to TcdB1 in the presence and absence of PepB2 or PepB1. Electrical resistance values for the T84 cells were then recorded at the time points indicated on the graph.

Circular Dichroism The CD spectra of these peptides were recorded on a JASCO J715 Spectropolarimeter (Jasco, Corp., Tokyo, Japan) in a cuvette with a path length of 0.1-cm. Each spectrum was recorded at a wavelength range of 200-260 nm at 0.1 nm intervals with 3 accumulations per spectrum. The peptides were tested at a concentration of 40 µM in PBS at 25° C.

Immunoblot of Intracellular Rac1

CHO-K1 cell were cultured at 37° C. in the presence of 6% $CO_2$ with F12-K containing 10% FBS, 100 units/ml penicillin, and 100 µg/ml streptomycin. CHO-K1 cells were seeded in 24-well plates at a density of $5.0 \times 10^4$ cells/well and allowed to attach overnight. TcdB was then combined with peptide in complete culture medium and added to cells. Following this exposure, total proteins were extracted by removing culture media and adding cold lysis buffer (1% SDS, 50 mm Tris-HCl (pH 7.4), 5 mm EDTA, and a protease inhibitor mixture). After lysing the cells, the protein extract was passed through a 22-gauge needle 10 times and then centrifuged for 5 min at 20,000×g. Proteins extracts (10 µg/well) were combined with sample buffer (62.5 mm Tris-HCl (pH 6.8), 2% SDS, 10% glycerol, 5% β-mercaptoethanol, and 0.001% bromphenol blue) and heated at 95° C. for 7 min. Proteins were then separated by 12% SDS-PAGE and transferred to a PVDF membrane by electroblotting. The membrane was blocked with 5% nonfat milk in wash buffer (20 mm Tris-HCl (pH 7.5), 100 mm NaCl, and 0.1% Tween 20). The membranes were then probed overnight at 4° C. with a mouse monoclonal antibody against total Rac1 (EMD Millipore, catalog number: 05-389) or a mouse monoclonal antibody recognizing non-glucosylated Rac1 (BD Bioscience, catalog number: 610651). The membrane was then washed and incubated with a secondary antibody conjugated to horseradish peroxidase. After another set of washes, the blots were developed with an enhanced chemiluminescent protein development system (GE Healthcare) and exposed to film.

In Vitro Glucosylation Assay

To determine how peptides described herein (e.g., PepB2) influence the glucosylation activity of TcdB, 400 nM of purified GST-Rac1 and 40 µM of UDP-glucose were combined with a range of concentrations of TcdB1 (1.2 nM-24 nM) or $GTD_{TcdB1}$ (0.5 nM-25 nM). These reactions were set up in 20 µL volumes in a buffer consisting of 50 mM HEPES (pH 7.5), 100 mM KCl, 2 mM $MgCl_2$, 1 mM $MnCl_2$, and 100 µg/ml bovine serum albumin (BSA). The reactions were carried out at 37° C. for 1 hour and were stopped by heating the samples at 95° C. for 7 mM in sample buffer (62.5 mm Tris-HCl (pH 6.8), 2% SDS, 10% glycerol, 5% β-mercaptoethanol, and 0.001% bromphenol blue). Twenty-five percent of the contents of each reaction was subjected to electrophoresis with a 10% SDS-polyacrylamide gel and then transferred to a PVDF membrane by electroblotting. The membrane was blocked with 5% nonfat milk in wash buffer. The membranes were then incubated overnight at 4° C. with a mouse monoclonal antibody against total Rac1 (EMD Millipore, catalog number: 05-389) or a mouse monoclonal antibody recognizing non-glucosylated Rac1 (BD Bioscience, catalog number: 610651). The membrane was then washed, incubated with a secondary antibody conjugated to horseradish peroxidase, and developed with enhanced chemiluminescent protein development system (GE Healthcare). The signal was then quantified by densitometry analysis of digitized images using ImageJ 1.37V software (Wayne Rasband, National Institutes of Health).

In Vitro Autoprocessing Assay

TcdB autoprocessing was activated by incubating 37 pM of TcdB1 with 500 µM of inositol hexaphosphate (IP6) for 1 h at 37° C. in a buffer consisting of 50 mM HEPES (pH 7.5), 150 mM NaCl, and 20 mM DTT. After stopping the reaction by heating the samples at 95° C. for 7 min in sample buffer (62.5 mm Tris-HCl (pH 6.8), 2% SDS, 10% glycerol, 5% β-mercaptoethanol, and 0.001% bromphenol blue), cleavage of TcdB was evaluated by immunoblot. The immunoblot was performed by first separating the different forms of TcdB by 8% SDS-PAGE and then transferring the proteins to a PVDF membrane by electroblotting. After blocking the membrane with 5% nonfat milk in wash buffer, the membranes were probed overnight at 4° C. with antibodies against the amino-terminal of TcdB (R&D Systems, catalog number: AF6246). The membrane was then washed, exposed to secondary antibody conjugated to horseradish peroxidase, and developed with enhanced chemiluminescent protein development system (GE Healthcare). The signal was then quantified by densitometry analysis of digitized images using ImageJ 1.37V software (Wayne Rasband, National Institutes of Health).

Flow Cytometry

In these experiments, CHO-K1 cells (ATCC) were cultured in F12-K with 10% FBS in tissue culture treated T-75 flasks at 37° C. in the presence of 6% $CO_2$. Before flow cytometry analysis, cells were detached using a non-enzymatic cell dissociation buffer (ThermoFisher Scientific, catalog number: 13150-016) and counted with a hemocytometer. Next, $4.0 \times 10^5$ cells were suspended in 300 µl of media (F12-K with 10% FBS) and were exposed to TcdB1 labeled with Alexa Fluor 488 ($TcdB1_{AF488}$) at 37° C. TcdB1 was labeled with Alexa Fluor 488 dye via primary amines (ThermoFisher Scientific, catalog number: A10235). Cell associated fluorescence was quantified using a FACSCalibur flow cytometer (University of Oklahoma Health Sciences Center). The resulting data were analyzed using FLOWJO software (Tree Star, San Carlos, Calif.). Cellular uptake was determined using 0.2% trypan blue to quench extracellular fluorescent signal immediately before flow cytometry analysis.

Confocal Microscopy

CHO-K1 cells (ATCC) were seeded in 12 well plates at a density of $5.0 \times 10^4$ cells per well in F12-K containing 10% FBS (ATCC) and allowed to attach overnight. Prior to toxin addition, cells were exposed to 75 nM of LysoTracker Red DND-99 (ThermoFisher Scientific, catalog number: L7528) in complete media for 30 minutes. In LysoTracker containing cell culture media, cells were then exposed to 20 nM $TcdB1_{AF488}$ alone or in combination with 50 µM PepB1 or 50 µM PepB2. The live cells were then imaged using a Leica SP2 MP Confocal with a 63×HCX APO 0.9 NA dipping lens (University of Oklahoma Health Sciences Center).

Differential Scanning Fluorimetry (DSF)

The thermal stability ($T_m$) of purified TcdB1 was determined in the presence and absences of PepB2. A $T_m$ value is the temperature at the midpoint of the transition from folded to unfolded and is found by plotting the first derivative of fluorescence versus temperature. These assays were performed by combining TcdB1 with SYPRO Orange and then monitoring fluorescence emissions as SYPRO Orange binds to hydrophobic regions of proteins that become exposed during temperature-induced unfolding. An Applied Biosystems 7500 real-time PCR system was used to monitor fluorescence emission of the protein/dye mixture as temperature was stepped from 25° C. to 99° C. These reactions were performed in quadruplicate with 740 nM of TcdB1 in a buffer comprising 20 mM HEPES (pH 8.0) and 150 mM NaCl. These reactions were carried out with 500 µM of PepB2 or PepB1 peptide. The presence of PepB2 or PepB1 did not contribute to fluorescence emissions.

BSA Conjugation

PepB2 was covalently attached to BSA either at the amino-terminal end of the PepB2 peptide (forming BSA-N-PepB2) or at the carboxyl-terminal of PepB2 (forming PepB2-C-BSA) by GenScript (Piscataway, NJ). Conjugation of the amino-terminal of PepB2 to BSA was performed using glutaraldehyde. Conjugation of the caryboxyl-terminal of PepB2 to BSA was achieved using EDC (1-ethyl-3-(-3-dimethylaminopropyl) carbodiimide hydrochloride). After the conjugation reactions, BSA-N-PepB2 and PepB2-C-BSA were dialyzed in PBS to remove free peptide. SDS-PAGE was employed to demonstrate that unconjugated peptide was removed from PepB2-C-BSA.

Results

TcdB2 Peptides Inhibit Cytotoxicity

Previous work identified TcdB amino acid residues 1652-1851 as a region that mediates protein-protein interactions and influences the exposure of neutralizing epitopes in TcdB2 (previously termed $TcdB_{O27}$ and $TcdB_{HV}$). A series of 10 water-soluble peptides spanning amino acids 1753-1851 of TcdB2 (Table 1) were designed and tested for inhibitory activity against TcdB1 and TcdB2 using CHO-K1 cells (which are highly sensitive to TcdB). In addition to the 1753-1851-derived peptides, 3 peptides (numbered 11-13) derived from the proximal 1851-2366 region of TcdB2 were included for comparison. This screen identified a total of 4 peptides (FIG. 1) which had inhibitory activity against both TcdB1 and TcdB2 toxins. Three of the inhibitory peptides (numbers 3-5, SEQ ID NOS: 4-6, respectively) had a common 11-amino acid sequence NVFKGNTISDK (SEQ ID NO:1) derived from amino acids 1769-1779 of TcdB2. These three inhibitory peptides having the mutual sequence SEQ ID NO:1 were derived from the 1761-1787 region of TcdB2. A fourth peptide, number 9 (SEQ ID NO:10), having weaker inhibitory activity was derived from residues 1846-1866.

Figure 2:
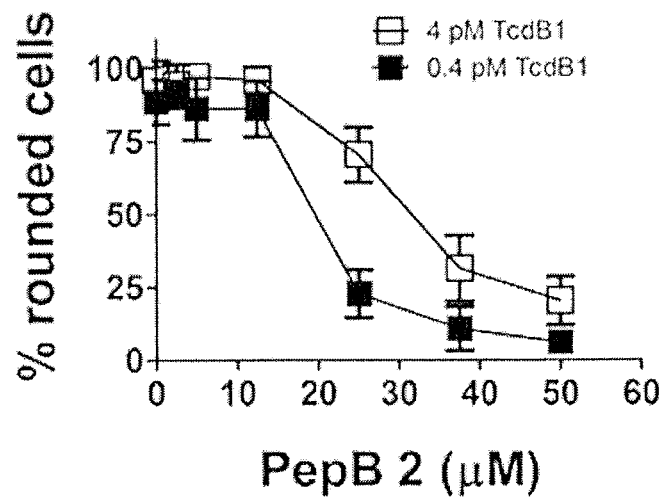
FIG. 2 shows results of a cell rounding assay examining different concentrations of PepB2 that inhibit 4 pM or 0.4 pM of TcdB1. The graph represents the percent of cells rounding after 2 h and is presented as the mean from 6 different fields±S.D. shows TcdB inhibition with a peptide derived from TcdB2 but not TcdB1.
Figure 3:
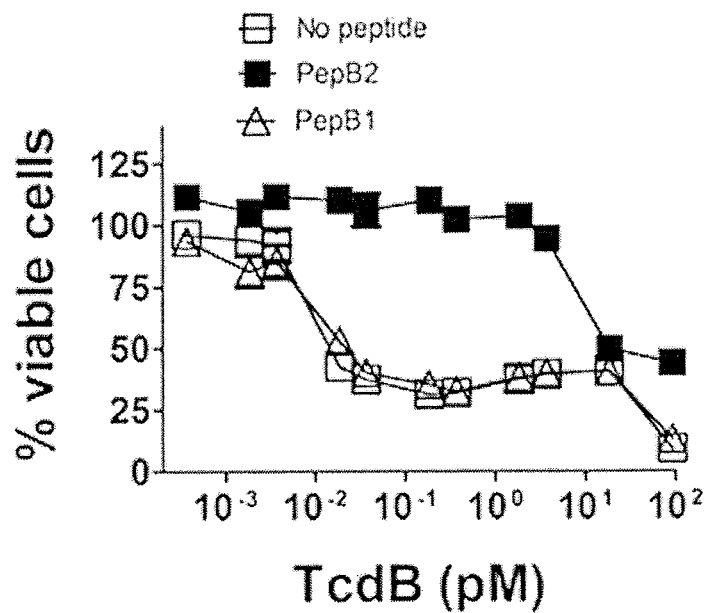
FIG. 3 shows results of a cytotoxicity assay demonstrating PepB2 protects CHO-K1 cells from a wide range of TcdB1 or TcdB2 concentrations. The graph represents the percent of viable cells after treatment for 24 h with TcdB1 in the presence and absence of 50 μM of PepB2 or PepB1. Data are presented as mean (n=3)±S.D.
Figure 4:
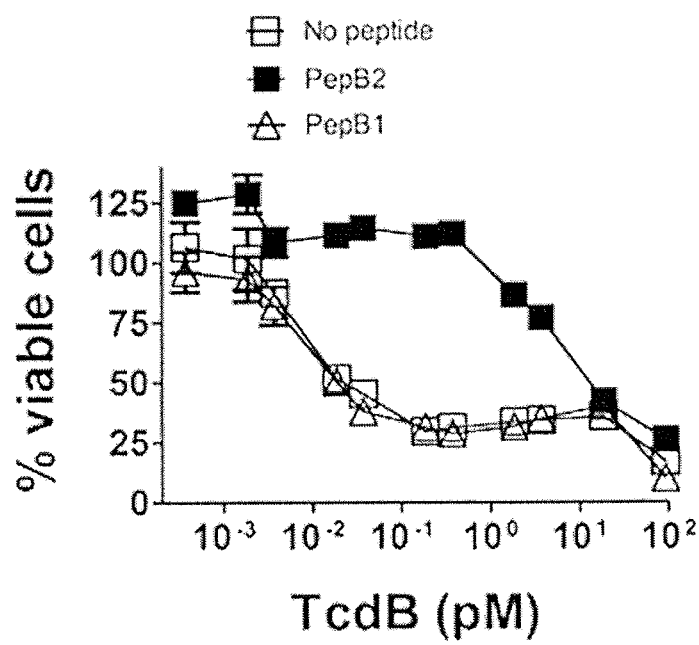
FIG. 4 shows results of a cytotoxicity assay demonstrating PepB2 protects CHO-K1 cells from a wide range of TcdB2 concentrations. The graph represents the percent of viable cells after treatment for 24 h with TcdB2 in the presence and absence of 50 μM of PepB2 or PepB1. Data are presented as mean (n=3)±S.D.
Figure 5:
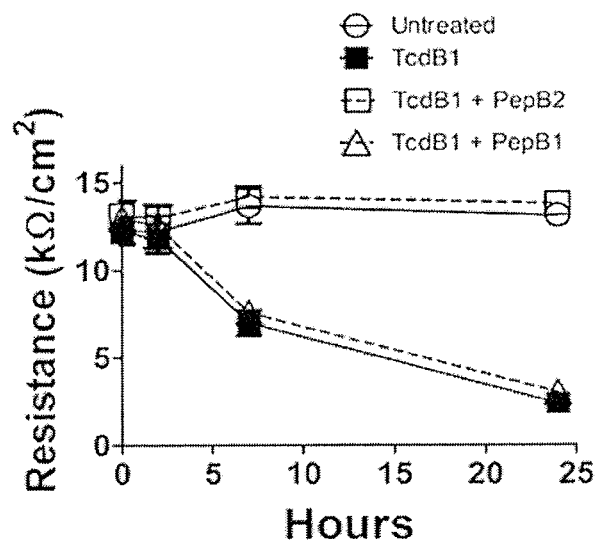
FIG. 5 shows that PepB2 prevents TcdB-induced damage to tight junctions as shown by measuring transepithelial resistance in T84 cells. T84 cells were grown in a transwell plate until the formation of tight junctions and then exposed to 40 pM of TcdB1 in the presence and absence of 50 μM of PepB2 or PepB1. Electrical resistance values were then recorded at the indicated time points. Data are presented as mean (n=4)±S.D. A decrease in resistance values indicates that tight junctions are disrupted.

The next set of experiments focused on the inhibitory activity of Peptide 5 (also referred to herein as PepB2) which comprises the 19 amino acids 1769-1787 of TcdB2 (NVFK-GNTISDKISFNFSDK-SEQ ID NO:6) was further investigated. In the first experiment, PepB2 was tested to determine the minimal inhibitory concentration. This initial study demonstrated 25 µM to 50 µM of PepB2 was necessary to protect CHO-K1 cells from TcdB1 after 2 h (FIG. 2). A peptide named PepB1 made from residues 1769-1787 of TcdB1 (having the amino acid sequence NVFKDKT-LANKLSFNFSDK—SEQ ID NO:15), which are homologous to the PepB2 amino acid sequence SEQ ID NO:6 in TcdB2, was also studied. The PepB1 sequence differs from PepB2 at amino acid positions 5, 6, 8, 9, 10, and 12, and lacks TcdB inhibitory activity. Next, the ability of PepB2 to provide long-term protection from TcdB1 and TcdB2 over a range of toxin concentrations (FIGS. 3-4) was examined. In these experiments, CHO-K1 cells were exposed to TcdB, plus or minus PepB2, and then the number of cells protected by PepB2 (or PepB1) was quantified after 24 h. Results from this study demonstrated that PepB2 increased the 50% toxic concentration (TC50) of TcdB1 500 fold and the TC50 of TcdB2 200 fold (FIGS. 3-4). In addition to the effects on CHO-K1 cells, TcdB exposure to a polarized human epithelial cell line (T84 cells) damaged the cytoskeleton and tight junctions in the T84 cells causing disruption of transepithelial resistance. PepB2 was found to block TcdB mediated disruption of transepithelial resistance (FIG. 5). In contrast to PepB2, peptide PepB1 based on the homologous region of TcdB1, did not inhibit the cytotoxicity of TcdB1 or TcdB2 (FIGS. 3-5). A similar level of protection from TcdB by PepB2 was observed in HELA cells (not shown).

Figure 6:
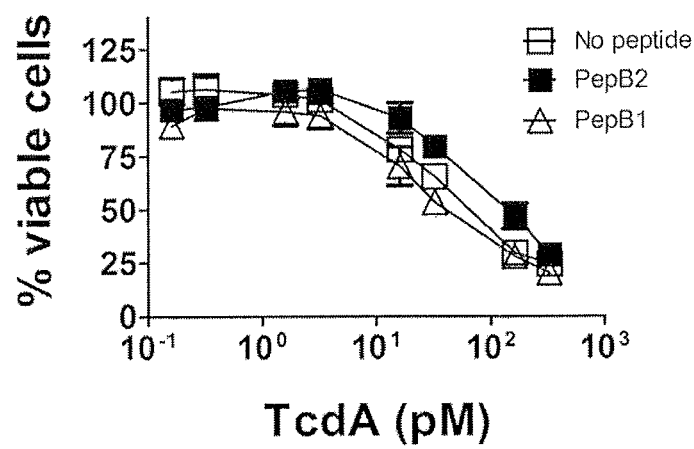
FIG. 6 provides results of cell viability assays showing that PepB2 does not inhibit TcdA toxin or *Bacillus anthracia* lethal toxin (LT). (A) PepB2 does not reduce TcdA induced cytotoxicity in CHO-K1 cells. The graph represents the percent of viable cells after treatment for 24 h with TcdA in the presence and absence of 50 μM of PepB2 or PepB1. Data are presented as mean (n=3)±S.D. (B) PepB2 does not reduce the cytotoxicity activity of LT in RAW 264.7 cells. The graph depicts the amount of viable RAW 264.7 cells after the cells are exposed to LT for 24 hours with 50 μM of PepB2 or PepB1. Data are presented as mean (n=3)±S.D.
Figure 6:
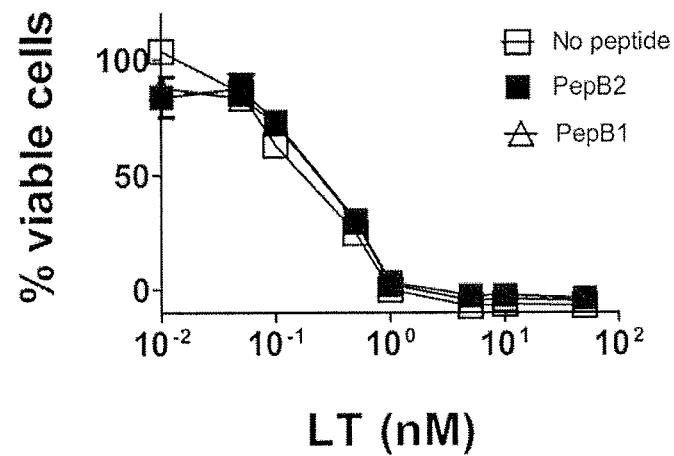

To test PepB2 for toxin specificity, the peptide was incorporated into cytotoxicity assays using *C. difficile* TcdA and *Bacillus anthracis* lethal toxin (LT). Results from these experiments showed that PepB2 did not reduce the toxicity exhibited by either TcdA toxin or *Bacillus anthracis* lethal toxin (FIG. 6).

TABLE 1

TcdB2-derived peptides. Activity against TcdB1 and TcdB2 is shown in FIG. 1.

| Peptide | TcdB2 Position | Amino Acid Sequence | SEQ ID NO: |
|---|---|---|---|
| 1 | 1748-1767 | DFILMSTDEENKVSQVKIRF | 2 |
| 2 | 1752-1769 | MSTDEENKVSQVKIRFTN | 3 |
| 3 | 1761-1779 | SQVKIRFT<u>NVFKGNTISDK</u> | 4 |
| 4 | 1766-1782 | RFT<u>NVFKGNTISDK</u>ISF | 5 |
| 5 (PepB2) | 1769-1787 | <u>NVFKGNTISDK</u>ISFNFSDK | 6 |
| 6 | 1782-1799 | FNFSDKQDVSINKVISTF | 7 |
| 7 | 1787-1805 | KQDVSINKVISTFTPSYYV | 8 |
| 8 | 1806-1822 | EGLLNYDLGLISLYNEK | 9 |
| 9 | 1846-1866 | KPPIKNLITGFTTIGDDKYYF | 10 |
| 10 | 1850-1869 | KNLITGFTTIGDDKYYFNPD | 11 |
| 11 | 1861-1879 | DDKYYFNPDNGGAASVGET | 12 |
| 12 | 1895-1913 | QTGVFSTEDGFKYFAPADT | 13 |
| 13 | 1962-1980 | TGRAFKGLNQIGDDKFYFN | 14 |

Substitutions of Specific Amino Acids in PepB2

Figure 7:
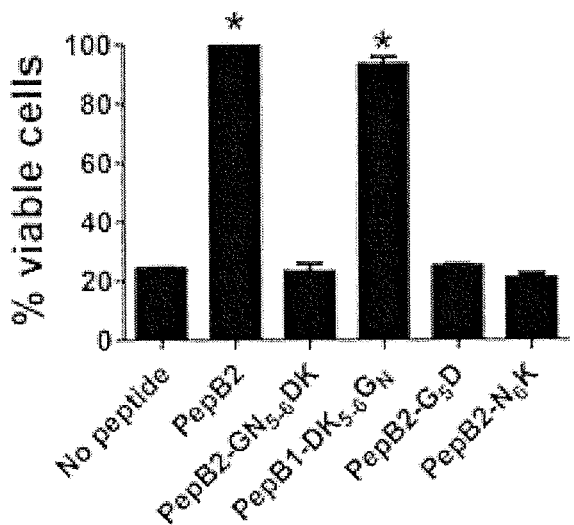
FIG. 7 shows comparative TcdB inhibitory activity of various PepB2 variants. The bar graph shows the percent of viable CHO-K1 cells after treatment for 24 h with 0.4 pM of TcdB1 in the presence of 50 μM of each variant peptides. Amino acid sequences of the peptides are shown in Table 2. Data are presented as mean (n=3)±S.D. Asterisks indicate significant increase above toxin treated controls. *, p<0.001.

Experiments were next designed to examine how substitutions in specific amino acids affected PepB2 activity. To guide these experiments, we took advantage of sequence differences between PepB2 and PepB1 (see alignment in Table 2). A series of peptides were designed in which amino acids that differ between PepB2 and PepB1 were altered to reflect those found in the reciprocal peptide. These variant PepB2 and PepB1 peptides were then tested for their ability to inhibit TcdB cytotoxicity (FIG. 7). When $GN_{5-6}$ from PepB2 was replaced with $DK_{5-6}$ from PepB1 (PepB2-$GN_{5-6}$DK), the inhibitory activity of the resulting peptide was lost. Inhibitory activity was gained in PepB1 by the reciprocal substitution producing PepB1-$DK_{5-6}$GN. To determine if $G_5$ is necessary for the activity of PepB2, we substituted $G_5$ with the $D_5$ from PepB1 (PepB2-$G_5$D) and found that inhibitor activity was lost. The PepB2 activity was also lost when the $G_5$ was replaced with an S residue (PepB2-$G_5$S). We also replaced $N_6$ in PepB2 with the $K_6$ from PepB1 (PepB2-$N_6$K) and found that TcdB inhibitory activity also disappeared. Results from this line of investigation revealed that TcdB inhibitory activity was lost when either or both of $G_5$ and $N_6$ from PepB2 was replaced with the corresponding amino acid ($D_5$ or $K_6$) from PepB1. Collectively, these data indicate that in at least certain embodiments, the GN motif at positions 5 and 6 play an important role in the inhibitory activity of PepB2 against TcdB.

TABLE 2

Amino Acid substitutions in PepB2 and PepB1

| Peptide | Amino Acid Sequence | SEQ ID NO: |
|---|---|---|
| PepB2 | NVFKGNTISDKISFNFSDK | 6 |
| PepB1 | NVFKDKTLANKLSFNFSDK | 15 |
| PepB2-$GN_{5-6}$DK | NVFKDKTISDKISFNFSDK | 16 |
| PepB1-$DK_{5-6}$GN | NVFKGNTLANKLSFNFSDK | 17 |
| PepB2-$G_5$D | NVFKDNTISDKISFNFSDK | 18 |
| PepB2-$G_5$S | NVFKSNTISDKISFNFSDK | 19 |
| PepB2-$N_6$K | NVFKGKTISDKISFNFSDK | 20 |

Figure 8:
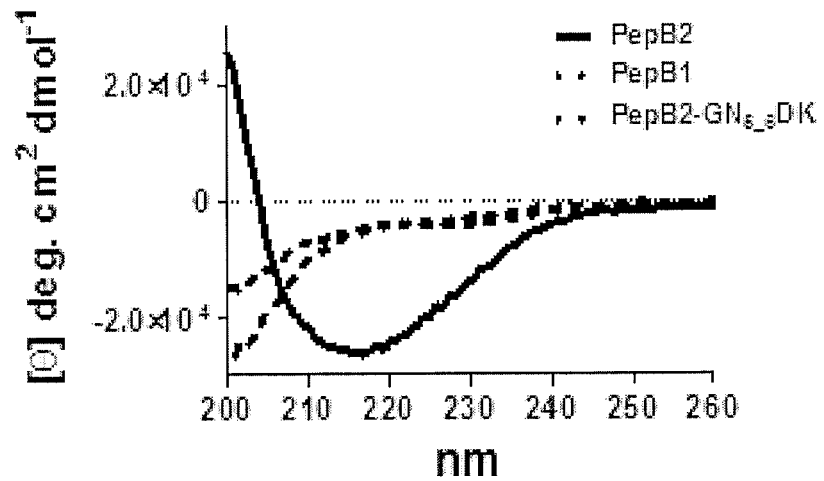
FIG. 8 is a comparison of CD spectra of PepB1, PepB2, and PepB2-GN$_{5-6}$DK peptides. The y-axis is presented in Molar Ellipticity [θ].

Since the fifth and sixth positions in PepB2 appear to be important for toxin inhibition, we next determined if the $GN_{5-6}$ pair was required for PepB2 to form a specific structure. Thus, circular dichroism (CD) analysis was utilized to gain structural insight into PepB2 and determine if the $GN_{5-6}$ to $DK_{5-6}$ switch results in an altered peptide structure. As shown in FIG. 8, the CD spectra of PepB1 and PepB2 are markedly different. PepB2 adopts an ordered structure that includes a significant level of α-helical content (~30% α-helix using BeStSel algorithm) while PepB1 appears to be mostly unstructured. Analysis of PepB2-$GN_{5-6}$DK revealed a CD spectrum similar to PepB1 and not PepB2 (FIG. 8). Thus, PepB2-$GN_{5-6}$DK is mostly disordered and the $GN_{5-6}$ pair contributes to the PepB2 peptide adopting an ordered structure (at least in comparison to a DK substitution at those positions). The GN motif forms a beta-turn in the peptide which appears to contribute to the ordered conformational structure of the peptide.

Figure 9:
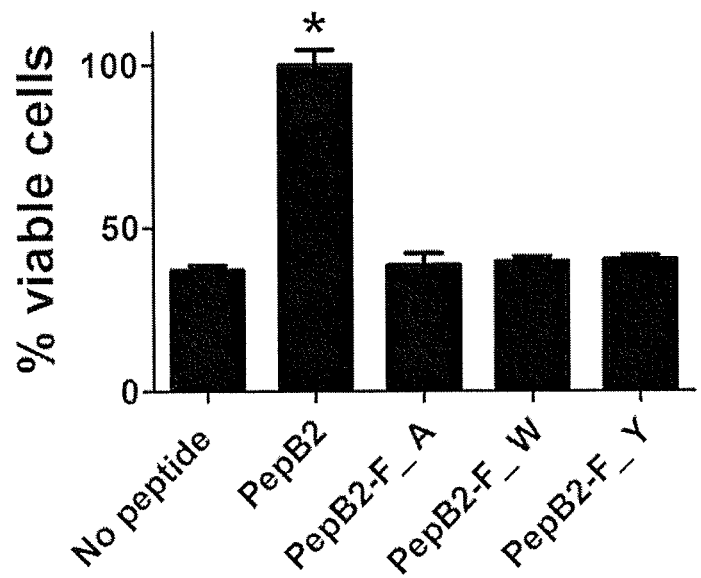
FIG. 9 shows a comparison of the TcdB inhibitory activity of PepB2 and three phenylalanine variant peptides in CHO-K1 cells. Amino acid sequences of the variant peptides are shown in Table 3. All three phenylalanine residues of PepB2 are substituted with A, W, or Y, respectively. The bar graph shows the percent of viable cells after treatment for 24 h with 0.04 pM of TcdB1 in the presence of 50 μM of each peptide. Data are presented as mean (n=3)±S.D. Asterisks indicate significant increase above toxin treated controls. *, $p<0.001$.
Figure 10:
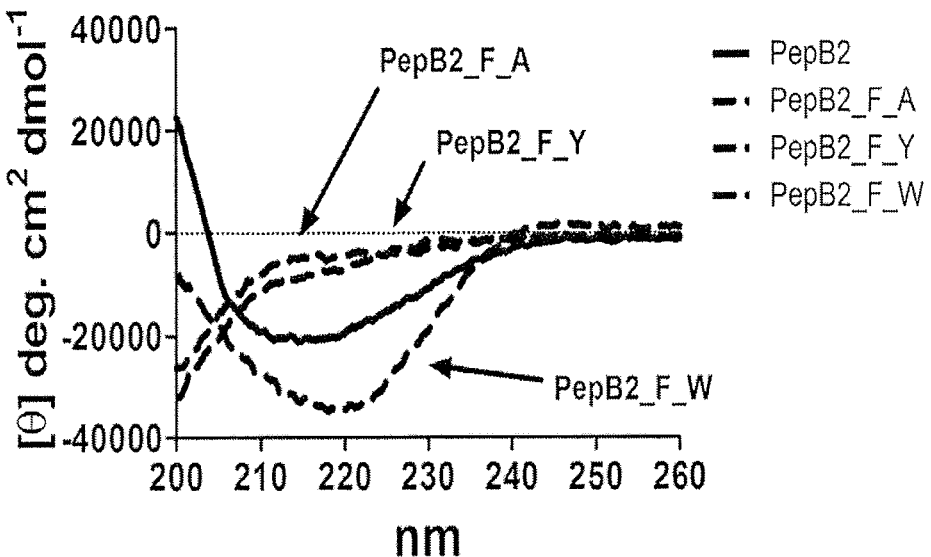
FIG. 10 is a comparison of CD spectra from PepB2 and the phenylalanine variant peptides of FIG. 9.

Other variant forms of PepB2 (Table 3) were also examined and the results revealed that TcdB inhibitory activity was reduced to near control levels when all three phenylalanines in positions 3, 14, and 16 were exchanged for alanines, tyrosines, or tryptophans (FIG. 9). CD analysis of these phenylalanine-substituted variant peptides also demonstrated a correlation between TcdB inhibitory activity and peptide conformation (FIG. 10).

TABLE 3

Variant forms of PepB2 with phenylalanine substitutions

| Peptide | Amino Acid Sequence | SEQ ID NO: |
|---|---|---|
| PepB2 | NVFKGNTISDKISFNFSDK | 6 |
| PepB2-F_A | NVAKGNTISDKISANASDK | 21 |
| PepB2-F_W | NVWKGNTISDKISWNWSDK | 22 |
| PepB2-F_Y | NVYKGNTISDKISYNYSDK | 23 |

Figure 11:
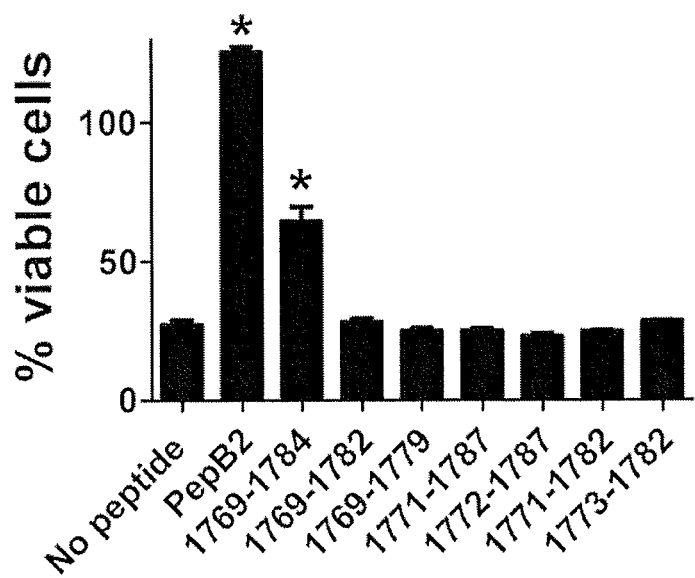
FIG. 11 is a comparison of the TcdB inhibitory activity of various truncated forms of PepB2 in CHO-K1 cells. Amino acid sequences of the truncated peptides are shown in Table 4. The bar graph shows the percent of viable cells after treatment for 24 h with 0.4 pM of TcdB1 in the presence of 50 μM of each peptide. Data are presented as mean (n=3)+S.D. Asterisks indicate significant increase above toxin treated controls. *, $p<0.001$.
Figure 12:
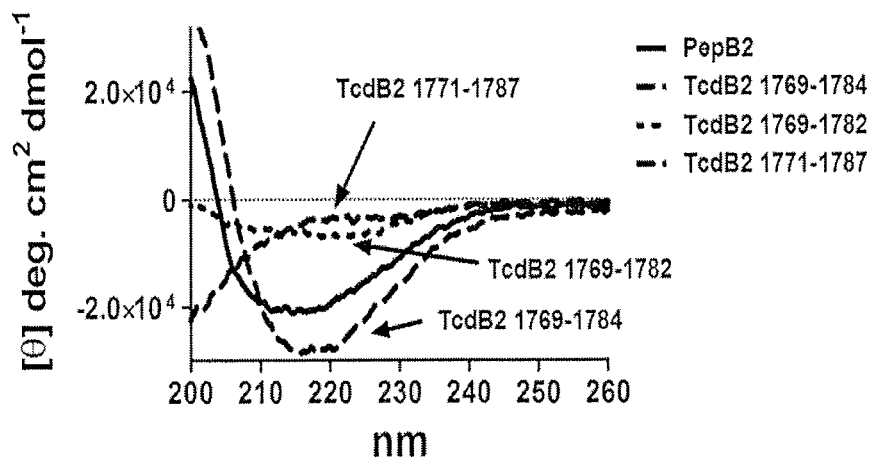
FIG. 12 is a comparison of CD spectra from PepB2 and several truncated forms of PepB2 of FIG. 11.

Other PepB2 variants formed by shortening the length of the peptide (Table 4) were also examined and the results revealed that TcdB inhibitory activity was correlated with peptide length (FIG. 11). When the three C-terminal amino acids were removed, inhibitory activity was reduced by about half. When 5 or more amino acids were removed from the C-terminal end, activity was reduced to control levels. When two or more N-terminal amino acids were removed, inhibitory activity was reduced to control levels. CD analysis of these shortened variant peptides also demonstrated a correlation between TcdB inhibitory activity and peptide conformation (FIG. 12).

TABLE 4

Shortened variants of PepB2 peptide

| Peptide | Amino Acid Sequence | SEQ ID NO: |
|---|---|---|
| TcdB2 1769-1787 (PepB2) | NVFKGNTISDKISFNFSDK | 6 |
| TcdB2 1769-1784 | NVFKGNTISDKISFNF | 24 |
| TcdB2 1769-1782 | NVFKGNTISDKISF | 25 |
| TcdB2 1769-1779 | NVFKGNTISDK | 26 |
| TcdB2 1771-1787 | FKGNTISDKISFNFSDK | 27 |
| TcdB2 1772-1787 | KGNTISDKISFNFSDK | 28 |
| TcdB2 1771-1782 | FKGNTISDKISF | 29 |
| TcdB2 1773-1782 | GNTISDKISF | 30 |

Impact of PepB2 on TcdB Enzymatic Activity and Cellular Entry

Figure 13:
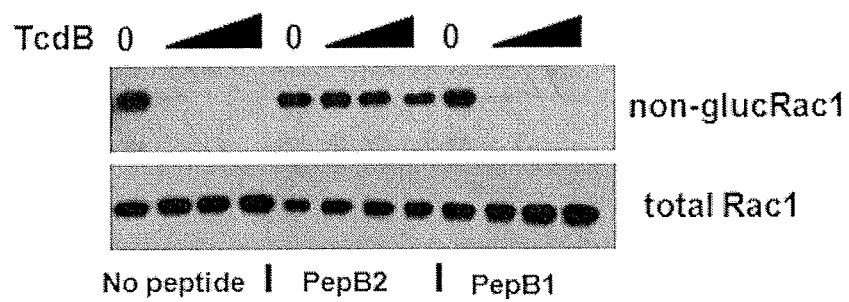
Figure 14A:
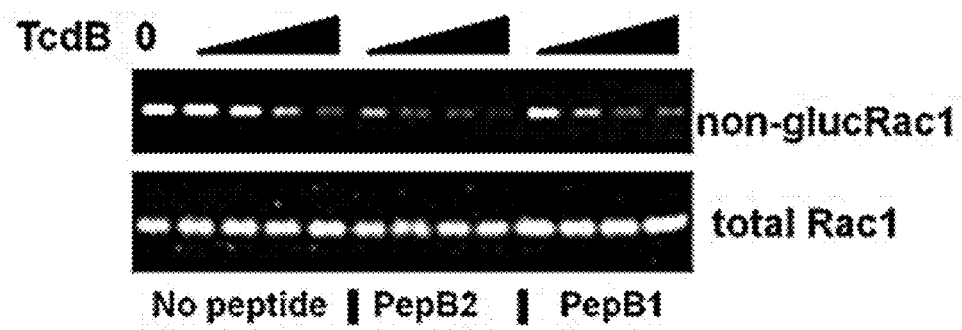
FIGS. 14A and 14B show results of an in vitro Rac1 glucosylation assay in which purified Rac1 and UDP-glucose were combined with TcdB1 (1.2 nM, 2.4 nM, 12 nM, and 24 nM. These experiments were carried out in the presence and absence of 50 μM PepB1 or PepB2 and then analyzed by immunoblot with antibodies recognizing non-glucosylated Rac1 and antibodies against total Rac1. The immunoblot data were quantified by densitometry analysis from a series of three reactions.
Figure 14B:
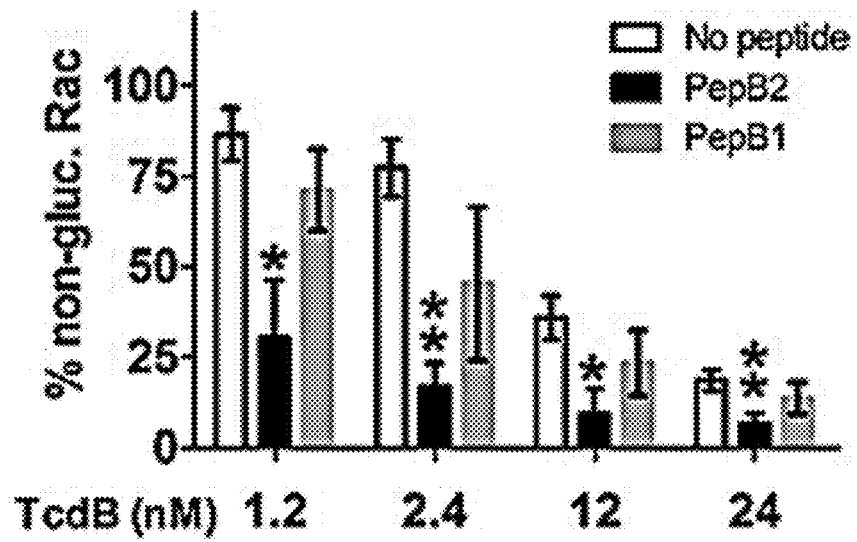
Figure 15A:
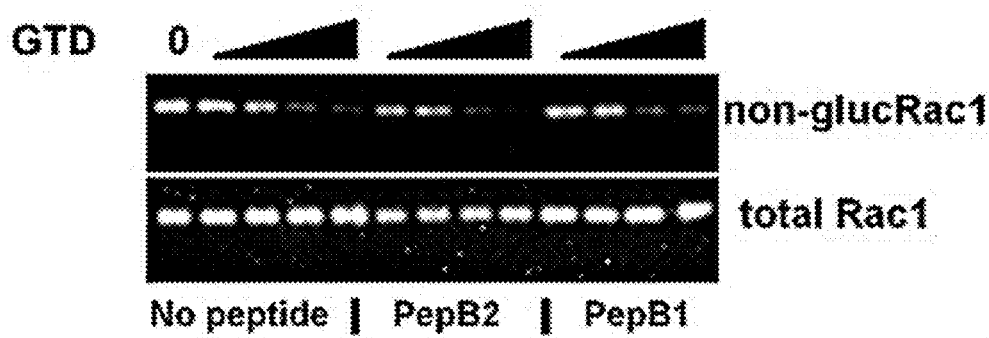
FIGS. 15A and 15B show results of an in vitro Rac1 glucosylation assay in which purified Rac1 and UDP-glucose were combined with GTD$_{TcdB1}$ (0.5 nM, 1 nM, 5 nM and 25 nM). These experiments were carried out in the presence and absence of 50 μM PepB1 or PepB2 and then analyzed by immunoblot with antibodies recognizing non-glucosylated Rac1and antibodies against total Rac1. The immunoblot data were quantified by densitometry analysis from a series of two reactions.
Figure 15B:
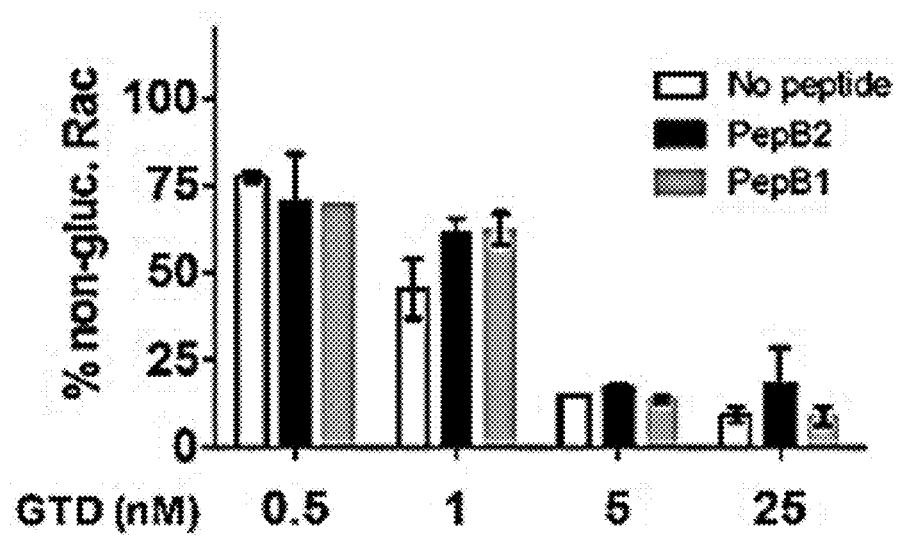
Figure 16A:
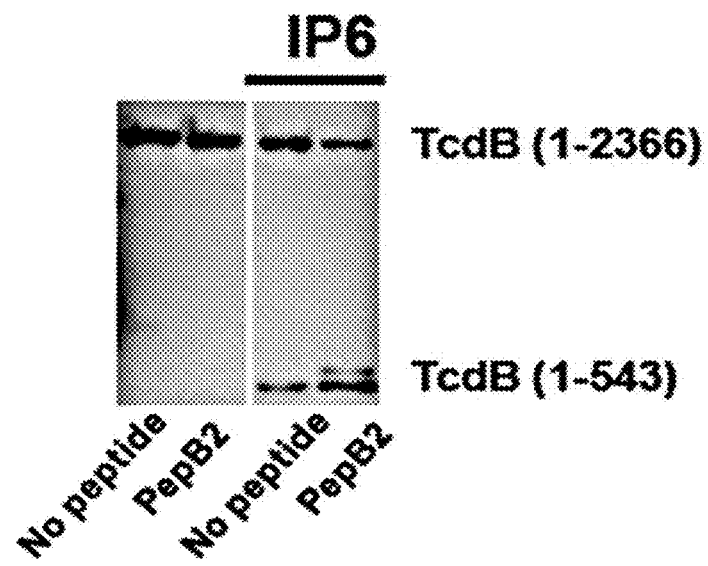
FIGS. 16A and 16B show results of an in vitro autoprocessing assay. TcdB autoprocessing was triggered by incubating TcdB1 (37 pM) for 1 h at 37° C. with 500 μM IP6 in the presence and absence of 50 μM PepB1 or PepB2. Autoprocessing activity was evaluated by immunoblot using an antibody that recognizes the amino-terminal of TcdB. From four separate reactions, densitometry analysis was performed on the bands corresponding to the GTD cleaved from full length TcdB. All bar graphs represent the mean densitometry ±S.D. Asterisks indicate significant change. *, $p<0.01$; **, $p<0.001$.
Figure 16B:
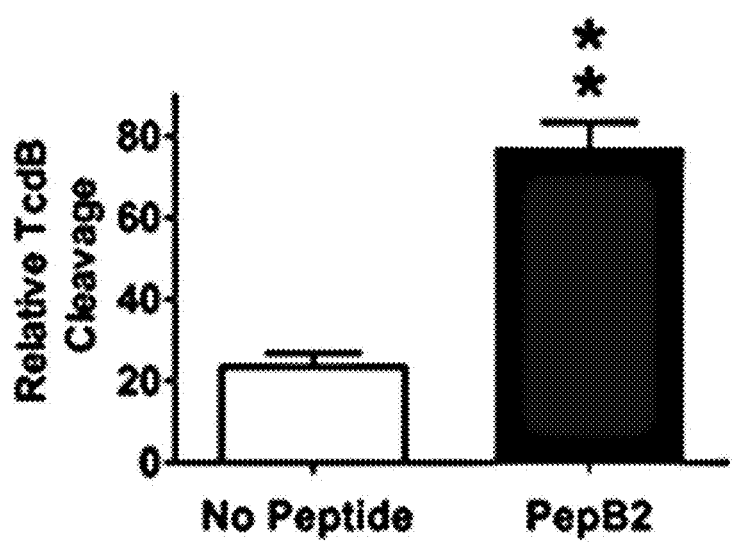

Experiments next explored the inhibitory mechanism used by PepB2. The terminal activity of TcdB is the glucosylation of intracellular small GTPases such as Rac1. Therefore in the next experiment, the impact of PepB2 on TcdB induced glucosylation of intracellular Rac1 was examined by immunoblot with an antibody recognizing non-glucosylated Rac1. As shown in FIG. 13, PepB2 prevented the intracellular glucosylation of Rac1. In contrast, the in vitro glucosyltransferase activity of TcdB was not reduced by PepB2, but instead lead to a modest increase (FIGS. 14A and 14B). We also examined the in vitro activity of the TcdB glucosyltransferase domain (GTD) in the presence of PepB2 and found that the peptide had no effect (FIGS. 15A and 15B). The impact of PepB2 on TcdB autoprocessing was also examined using an in vitro assay in the presence of inositol hexakisphosphate 6 (IP6). As shown in FIGs. 16A, and 16B, PepB2 did not reduce the IP6-induced TcdB autoproteolysis, but instead induced an increase in proteolytic cleavage. These results indicated that Pep2B does not block glucosyltransferase or autoprocessing activity, and most likely inhibits the toxin at a step earlier in cellular intoxication.

Figure 17A:
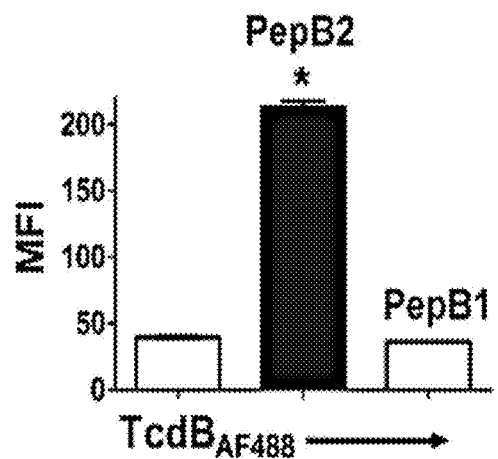
FIGS. 17A and 17B show results of a flow cytometry analysis of binding and entry of TcdB into cells. CHO-K1 cells were exposed for 10 minutes at 37° C. to 10 nM TCdB$_{AF488}$ in the presence and absence of 50 μM of peptide and then subjected to flow cytometry analysis. The results show that PepB2 disrupts the cellular entry of TcdB. To measure cellular uptake, extracellular quenching experiments were carried out in which cells were exposed to 0.2% trypan blue immediately before flow cytometry analysis. The signal that is not quenched corresponds to TcdB$_{AF488}$ taken up by cells. Histograms show TedB$_{AF488}$ that associates with cells before and after quenching. In the bar graphs, flow cytometry results are presented as median fluorescence intensity (MFI) from 3 experiments ±S.D. Asterisks indicate significant change. *, $p<0.001$.
Figure 17B:
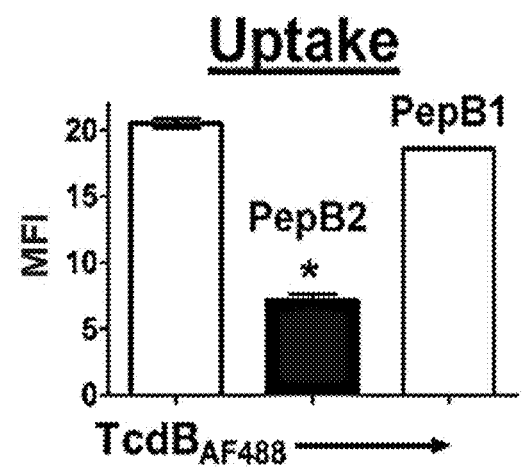
Figure 18:
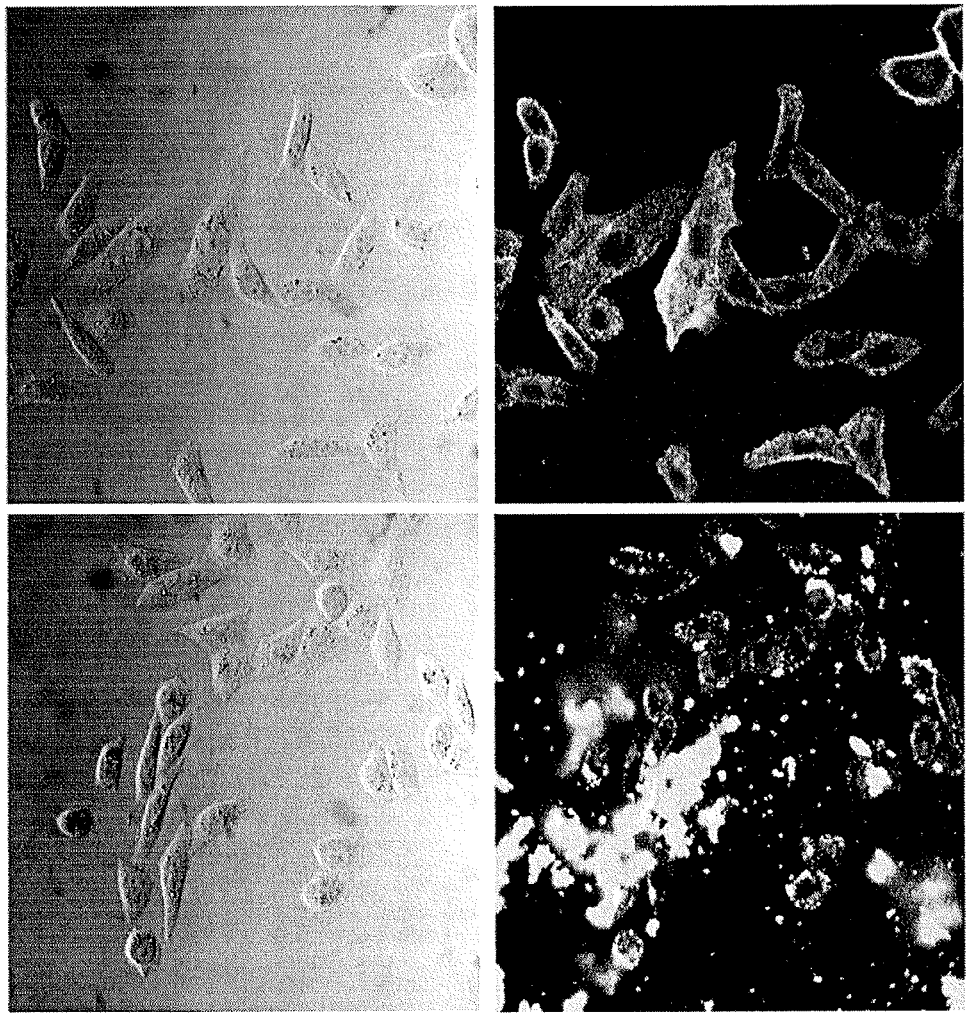
FIG. 18 show micrographs from confocal microscopy analysis of live CHO-K1 cells stained with 75 nM LysoTracker after exposure to 20 nM TcdB$_{AF488}$ for 1 h at 25° C. with 50 μM PepB1 or PepB2.
Figure 19:
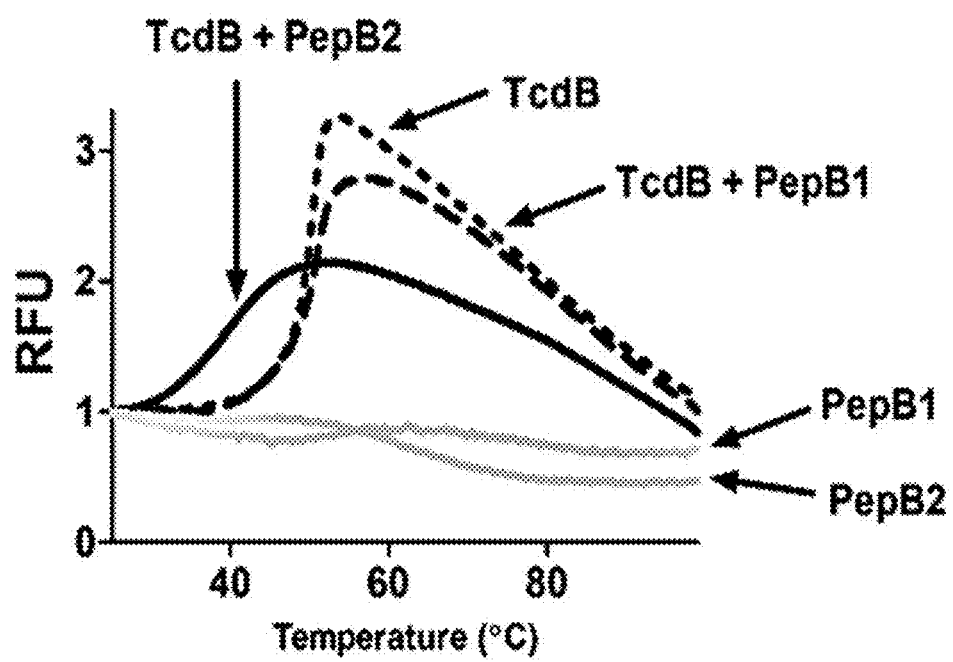
FIG. 19 shows results of differential scanning fluorimetry (DSF) used to determine the thermal stability (Tm) of TcdB (740 nM) with and without 500 μM PepB1 or PepB2. The graph depicts increases in relative fluorescence units (RFU) as SYPRO Orange binds to hydrophobic regions of proteins that undergo temperature induced unfolding. From these data, the Tm was calculated and is displayed as mean (n=4) and S.D.

The impact of Pep2B on binding and uptake of TcdB into CHO-K1 cells was measured using flow cytometry to detect interactions between cells and fluorescently labeled TcdB (TcdB$_{AF488}$) in the presence and absence of the peptide. As shown in FIGS. 17A, and 17B, TcdB interaction with cells was enhanced by PepB2 (left panel). However, when cellular uptake was evaluated using cell-impermeable trypan blue to quench extracellular fluorescence, PepB2 was found to decrease the uptake of TcdB$_{AF488}$ (right panel) This result suggested that PepB2 caused the deposition of large amounts of TcdB on the cell surface with only minor amounts entering cells. This finding was further supported by confocal microscopy images of live CHO-K1 cells. As shown in control cells with the non-inhibitory peptide, TcdB$_{AF488}$ enters the cells and traffics to endosomes marked by the pH-sensitive LysoTracker dye (FIG. 18, upper right). However, the addition of PepB2 led to a markedly different TcdB$_{AF488}$ staining pattern. These confocal images reveal PepB2 caused TcdB$_{AF488}$ to form soluble aggregates that are unable to properly enter cells (FIG. 18, lower right). These results indicate that PepB2 causes aggregates to form possibly by introducing conformational instability into TcdB. To determine if PepB2 alters TcdB structural integrity, thermal stability profiles were generated and compared between TcdB in the presence and absence of PepB2. Using SYPRO-Orange to detect exposure of hydrophobic domains across an increasing temperature gradient, the melting temperature (Tm) for TcdB alone was found to be 50.9° C., and the addition of PepB2 substantially reduced the Tm of TcdB to 40.8° C. (FIG. 19).

PepB2 Combines with Methyl Cholate to Inhibit TcdB

Figure 20A:
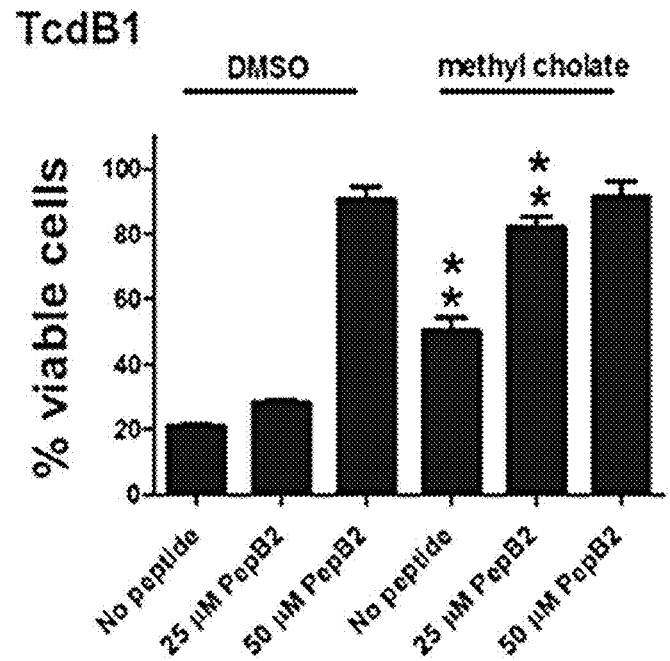
FIGS. 20A and 20B shows the inhibitory activity of PepB2 on TcdB1 and TcdB2 in combination with methyl cholate. TcdB inhibitory activity of PepB2 in CHO-K1 cells was measured in the presence and absence of 45 μM of methyl cholate. The bar graph shows the percent of viable cells after treatment for 24 h with 0.4 pM of TcdB1 or TcdB2. Data are presented as mean (n=3)±S.D. Asterisks indicate significant difference when comparing methyl cholate to DMSO control with same peptide exposure. **, $p<0.001$.
Figure 20B:
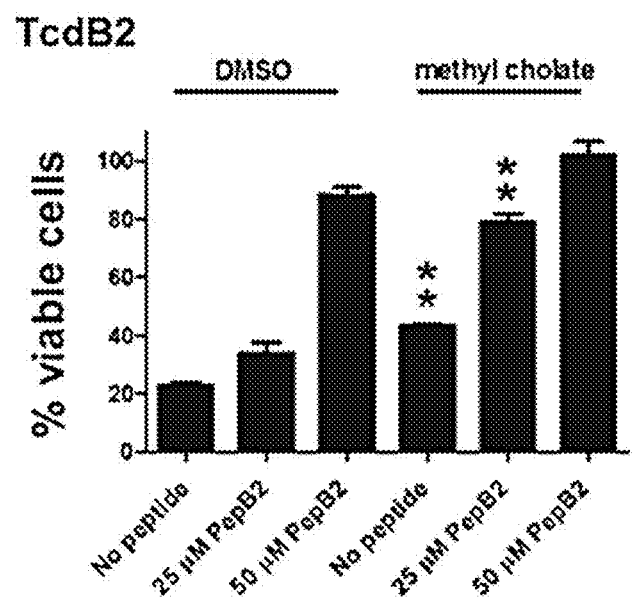

Recent studies found that methyl cholate inactivates TcdB by a process that involves increased conformational stability. Because PepB2 reduces the Tm of TcdB and thus reduces conformational stability, we predicted that methyl cholate might antagonize the effects of PepB2. However, as shown in FIGS. 20A, and 20B, methyl cholate did not reduce the inhibitory activity of PepB2 suggesting that there was no antagonistic interactions between the two inhibitors. Instead, an additive inhibitory effect was observed when the two inhibitors were combined at levels just below their inhibitory concentrations. As shown in FIGS. 20A, and 20B, 45 µM of methyl cholate or 25 µM of PepB2 had minimal impact on TcdB cytotoxicity, but strong inhibition was achieved when these two inhibitors were combined at these concentrations.

PepB2 is Enhanced by BSA Conjugation

Figure 21:
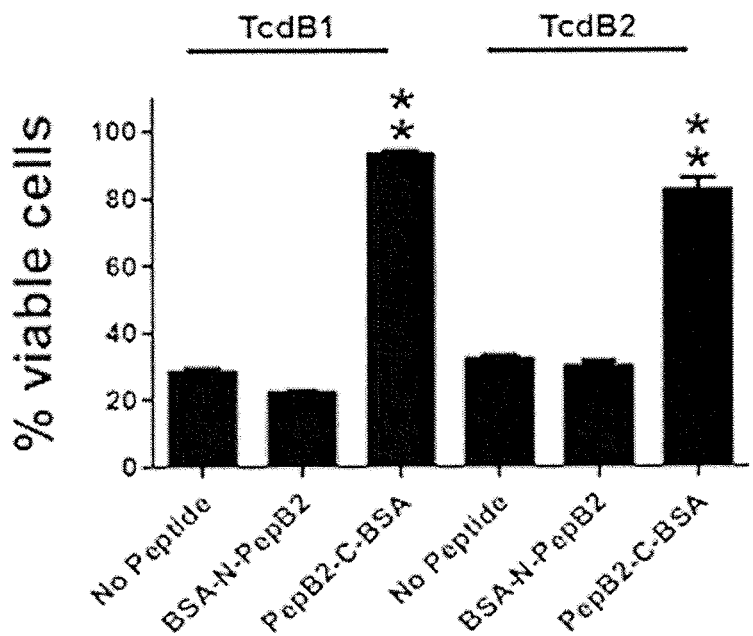
FIG. 21 shows the inhibitory activity of PepB2-BSA conjugates on TcdB1 and TcdB2. TcdB inhibitory activity of 1.5 μM of BSA-N-PepB2 or 1.5 μM of PepB2-C-BSA on CHO-K1 cells was measured. The bar graph indicates percent of viable cells after treatment for 24 h with 0.2 pM of TcdB1 or TcdB2. Data are presented as mean (n=3)±S.D. Asterisks indicate significant increase above toxin treated controls. **, $p<0.001$.

Currently, several therapeutic peptides using albumin as a drug carrier are fully approved drugs and many other peptide-albumin based drugs are under development. To this end, PepB2 was chemically attached to bovine serum albumin (BSA) either through the amino-terminal of PepB2 (BSA-N-PepB2) or through the carboxyl-terminal of PepB2 (PepB2-C-BSA). These two PepB2-BSA conjugates were then tested for inhibition of TcdB (TcdB1 or TcdB2) cytotoxicity. As shown in FIG. 21, BSA-N-PepB2 did not protect cells from TcdB cytotoxicity; however, PepB2-C-BSA was able to inhibit TcdB induced cytotoxicity. Moreover, BSA conjugation to the carboxyl-terminus of PepB2 appeared to improve PepB2 effectiveness because PepB2-C-BSA inhibited TcdB at approximately 1.5 µM while non-derivatized PepB2 inhibited in the range of 25 to 50 µM.

On the Mechanism of Inhibition of TcdB by PepB2

Our first step in elucidating how PepB2 inhibited TcdB was to examine the glucosyltransferase activity. Results from this analysis revealed that in vitro TcdB glucosyltransferase activity was not inhibited by PepB2 but was actually increased (FIGS. 13-16). The same analysis was also performed on purified GTD, and PepB2 was not found to cause any significant difference in GTD activity (FIGS. 13-16), indicating that PepB2 does not directly interact with the GTD of TcdB. Similar to glucosyltransferase activity we detected an increase in autoprocessing in the presence of PepB2 (FIGS. 13-16). These data demonstrated two interesting points. First, PepB2 does not inhibit the cytotoxicity of TcdB by directly blocking either enzymatic process. Second, PepB2 enhances glucosyltransferase and autoprocessing activity of TcdB. This second observation suggests that PepB2 places TcdB in a conformation that allows more efficient enzymatic activity. Previous studies suggested that glucosyltransferase and autoprocessing are constrained within fully intact TcdA or TcdB due to interaction with other regions of the toxin. Thus, PepB2 could be displacing these interactions and relieving the conformational restrictions on enzymatic domains within TcdB, but in doing so invokes a structure that precludes cell entry.

Since PepB2 did not directly reduce the glucosyltransferase activity of TcdB but did inhibit intracellular Rac1 glucosylation, we postulated that PepB2 might inhibit the cell entry process. The entry of TcdB into cells depends on a set of complex coordinated steps that likely involves multiple structural transitions. Thus, disrupting any one of these steps could prevent TcdB from entering cells. As shown by flow cytometry, PepB2 caused TcdB to collect on the cell surface with only minimal amounts of toxin gaining entry into cells (FIGS. 17A and 17B). The confocal images provided a direct visualization of this effect. These images demonstrate that PepB2 caused TcdB to form aggregates, some of which appear to be intimately associated with the cell surface (FIG. 18). In contrast, cells treated with toxin in the absence of PepB2 show a pattern where TcdB binds the cell surface and then radiates into cells towards the cellular region marked by LysoTracker dye (FIG. 18). These findings indicate an inhibitory model where PepB2 does not trigger a dramatic unfolding event in TcdB but rather a subtle conformational disruption. Once exposed to cells in this conformational state, the toxin adopts a structure that leads to aggregation which prevents cell entry.

The mechanism for PepB2-mediated inhibition appears to differ from that of other inhibitors reported to target TcdB. For example, human alpha defensin 1 (HNP-1) promotes unfolding of the TcdB glucosyltransferase domain and interferes with the enzymatic activity of this domain. In contrast, PepB2 did not reduce TcdB glucosyltransferase activity in vitro. HNP-1 also is less specific than PepB2 because HNP-1 inhibits *Bacillus anthracis* lethal toxin while PepB2 does not (FIG. 6). Recent work has also begun to explore the use of small molecule inhibitors of TcdB such as methyl cholate and ebselen. Methyl cholate inhibits TcdB through a mechanism that involves blocking autoprocessing and receptor binding. This inhibitory mechanism is related to the ability of methyl cholate to increase the thermal stability of TcdB, which contrasts the reduced thermal stability triggered by PepB2 (FIG. 19). In FIGS. 20A, and 20B, the combined effects of methyl cholate and PepB2 were analyzed; and despite opposing effects on thermal stability, the two inhibitors combined to produce an additive inhibitory effect on TcdB.

Developing peptides to inhibit bacterial toxins was investigated in other studies using phage libraries and selecting for random peptides that bind to and inhibit toxin activity. The present approach differs considerably from phage library screens because we have used sequences derived from the toxin itself to develop a specific peptide based inhibitor of TcdB. With the appropriate biochemical and structural information, regions like TcdB2$_{1753-1851}$ may be identified in other multidomain toxins and targeted with rationally designed peptide inhibitors.

Region of TcdB Targeted by PepB2

Figure 22:
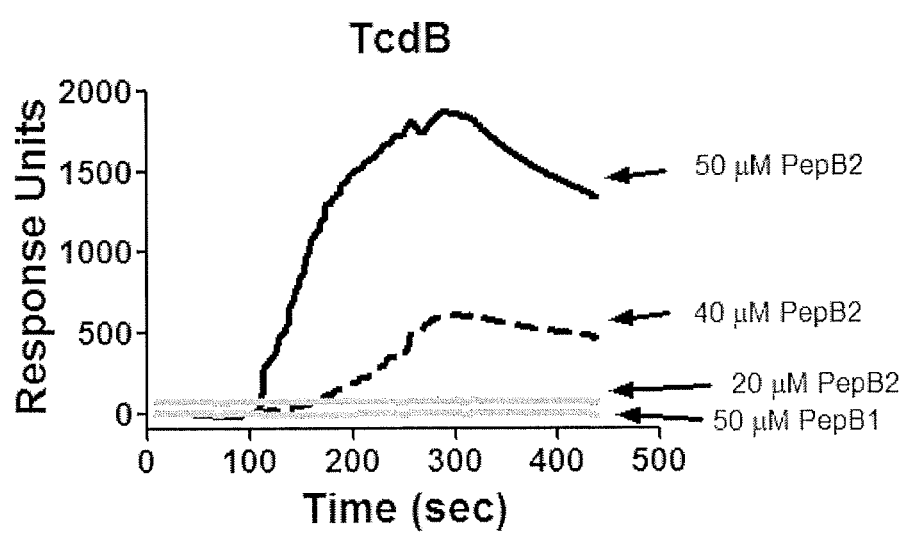
FIG. 22 shows the results of surface plasmon resonance (SPR) analysis of PepB2 binding TcdB or the CROP domain (TcdB2$_{1851-2366}$). TcdB2 was flow cell-immobilized and PepB2 or PepB1 were injected at a flow rate of 5 μl/min. The sensorgrams presented are subtracted from a reference cell containing immobilized BSA.
Figure 23:
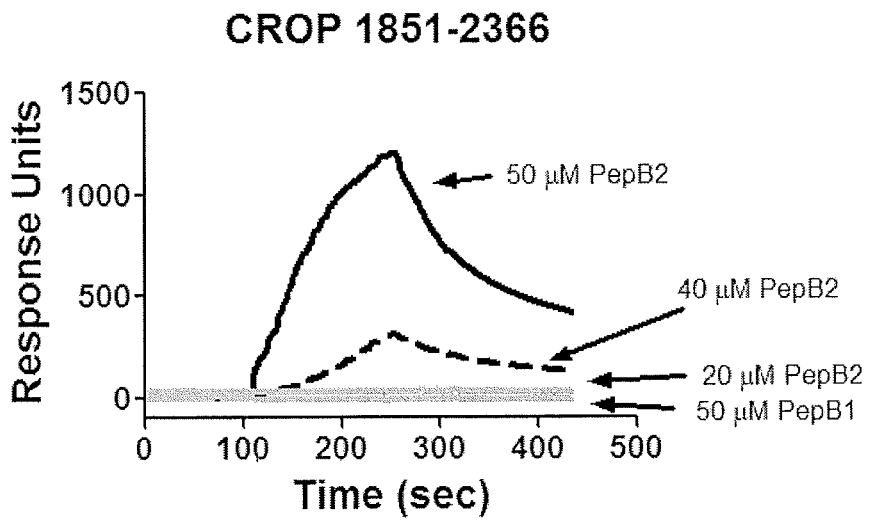
FIG. 23 shows the results of surface plasmon resonance (SPR) analysis of PepB2 binding to the CROP domain of TcdB2 (TcdB2$_{1851-2366}$). The CROP domain was flow cell-immobilized and PepB2 or PepB1 were injected at a flow rate of 5 μl/min. The sensorgrams presented are subtracted from a reference cell containing immobilized BSA.

The mechanism used by PepB2 to inhibit TcdB was investigated. Previous work demonstrated that the PepB2 sequence within intact TcdB was necessary for preserving strong intramolecular contacts. This observation led us to hypothesize that PepB2 was binding TcdB and our next experiment addressed this possibility by using surface plasmon resonance (SPR). The sensorgrams in FIG. 22 reveal that PepB2 binds sensor chip conjugated TcdB, while binding between TcdB and non-inhibitory PepB1 was not detected. A BSA coated reference channel did not bind PepB2. Examination of the sensorgrams reveals that TcdB is binding PepB2 through a multivalent interaction with approximately 250 molecules of PepB2 calculated to bind a single molecule of TcdB. The complex nature of the binding mechanism prevented saturable binding from being achieved and also prevented an affinity constant or rate constant from being determined. However, from these qualitative data, without wishing to be bound by theory, we could discern that PepB2 was binding TcdB with a relatively low affinity and that the binding appeared to utilize an avidity mechanism. Specificity of the binding interaction was confirmed by using soluble TcdB to compete away binding between PepB2 and sensor chip conjugated TcdB (FIG. 23).

Figure 24:
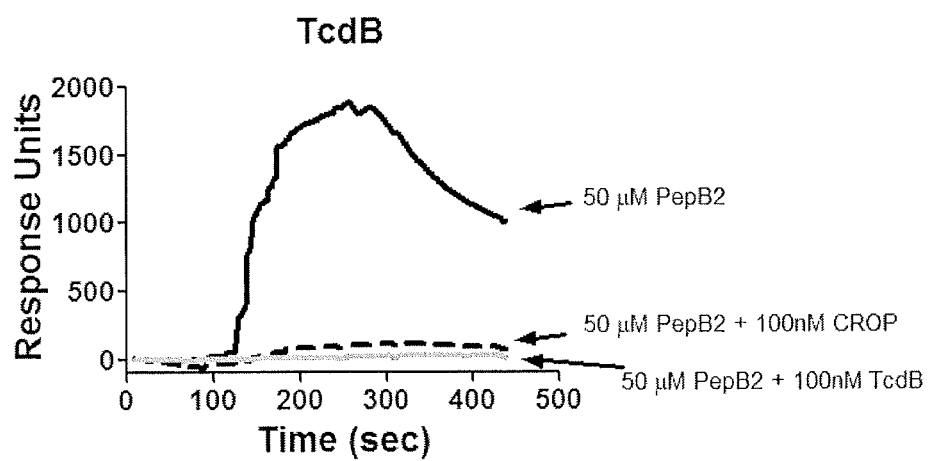
FIG. 24 shows the SPR results of a competition experiment of PepB2 binding TcdB. 100 nM of TcdB2 was combined with PepB2 before injection. TcdB2 was flow cell-immobilized and PepB2 was injected at a flow rate of 5 μl/min. The sensorgrams presented are subtracted from a reference cell containing immobilized BSA.
Figure 25:
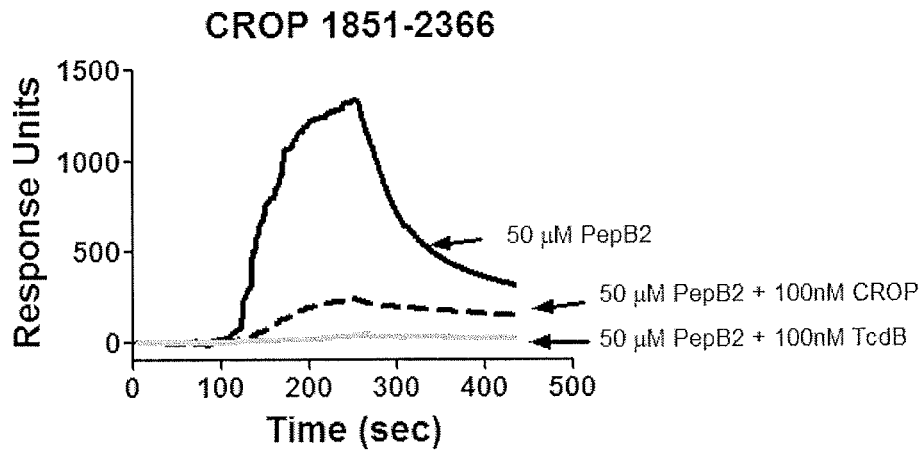
FIG. 25 shows the SPR results of a competition experiment of PepB2 binding to the CROP domain of TcdB2 (TcdB2$_{1851-2366}$). 100 nM of the CROP domain was combined with PepB2 before injection. The CROP domain was flow cell-immobilized and PepB2 or PepB1 were injected at a flow rate of 5 μl/min. The sensorgrams presented are subtracted from a reference cell containing immobilized BSA.

Because of the multivalent nature of the interaction between PepB2 and TcdB, we reasoned that PepB2 may be targeting a repeating structure such as the CROP domain found on the C-terminal portion of TcdB. Therefore, we next determined if we could compete away binding between PepB2 and TcdB using the purified CROPS (TcdB2$_{1851-2366}$). As shown in FIG. 23, the sensorgram reveals that the CROPS could compete away binding between PepB2 and TcdB. We also conjugated the CROPs to the sensorchip and obtained results that indicate a similar binding mechanism as observed with full length TcdB (FIGS. 24-25).

Figure 26:
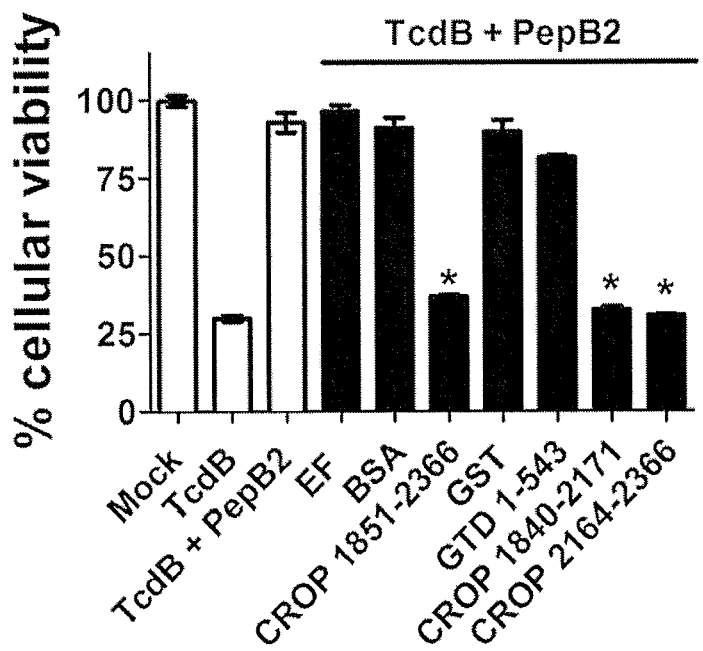
FIG. 26 shows the cytotoxicity activity of TcdB in the presence of PepB2 with proteins that absorb the peptide inhibitory activity. The bar graph shows the percent viability of CHO-K1 cells after treatment for 24 h with 0.75 pM of TcdB in the presence of 50 μM of PepB2. In this assay, PepB2 absorbing proteins were tested at a concentration of 1 μM and are listed on the graph. Data are presented as mean (n=3)±S.D. Asterisks indicate significant decrease in cytotoxicity compared to the TcdB+PepB2 condition. *, p<0.001.

Since PepB2 is binding the CROP region of TcdB, we next tested whether adding purified CROP to the cytotoxicity assay (% cell viability) described above could counteract the TcdB inhibitory activity of PepB2. In control experiments, purified CROPS (TcdB2$_{1851-2366}$) did not cause cytotoxicity by itself and did not alter the level of TcdB-induced cytotoxicity. However, TcdB2$_{1851-2366}$ was able to block PepB2 inhibitory activity when TcdB2$_{1851-2366}$, PepB2, and TcdB were combined (FIG. 26). This result suggests that excess TcdB2$_{1851-2366}$ is binding PepB2 and leaving TcdB free to intoxicate cells. Interestingly, the amount of CROP (1 μM) needed to block PepB2 (50 μM) provides further evidence of a multivalent interaction between PepB2 and the CROP domain. We were unable to compete away PepB2 inhibitory activity with control proteins such as BSA, Glutathione S-transferase (GST), or *Bacillus anthracis*'s edema factor (EF) (FIG. 26). Purified GST-tagged GTD was also unable to compete away PepB2 activity. To determine if PepB2 is binding a distinct region of the CROP domain, we also tested GST-tagged forms of shorter CROP sections such as TcdB2$_{1840-2171}$ (14 repeats) and TcdB2$_{2164-2366}$ (8 repeats). As shown in FIG. 26, both of these forms blocked PepB2 inhibitory activity.

Figure 27:
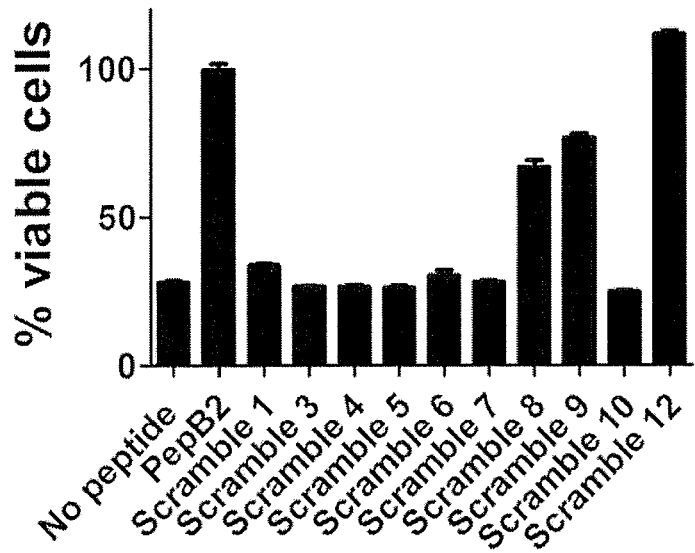
FIG. 27 shows comparative TcdB inhibitory activity of various peptide sequences. The PepB2 sequence (SEQ ID NO:6) was randomly scrambled 12 times which resulted in 10 different soluble peptides (amino acid sequences of the scrambled peptides are shown in Table 5). Anti-TcdB activity was examined in each of the 10 peptides and three (scramble peptide 8, scramble peptide 9, and scramble peptide 12) were found to have inhibitory activity. The bar graph shows the percent of viable CHO-K1 cells after treatment for 24 h with TcdB in the presence of 50 μM of each peptide tested. Data are presented as mean (n=3)±S.D.
Figure 28:
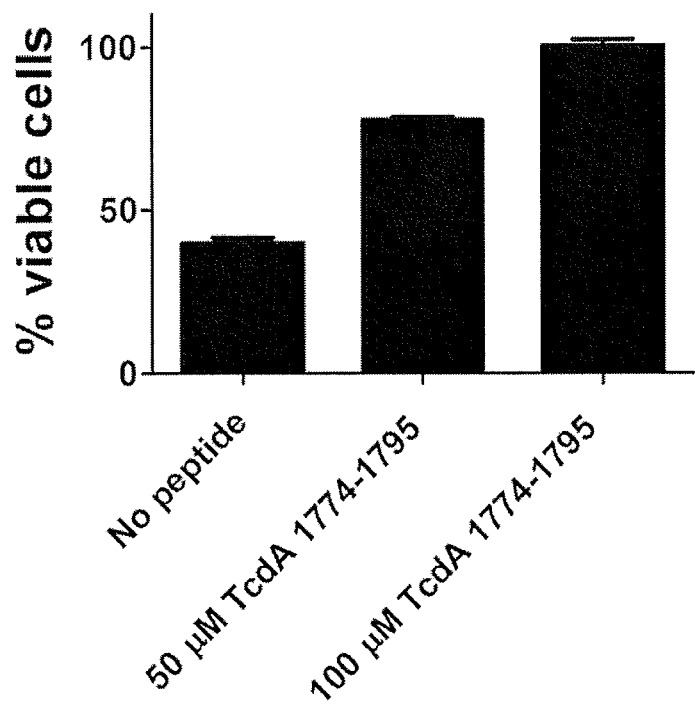
Figure 29A:
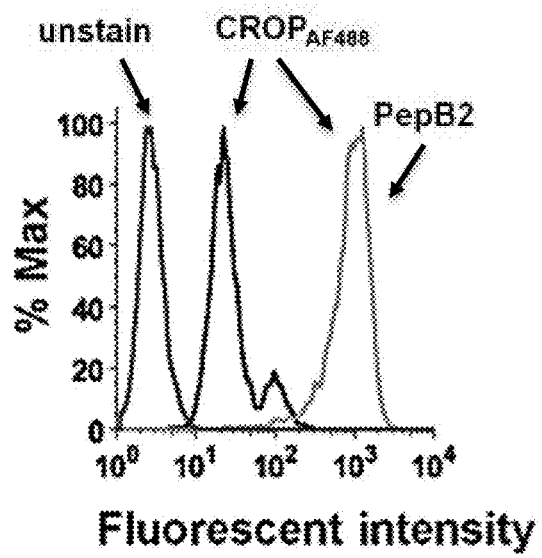
Figure 29B:
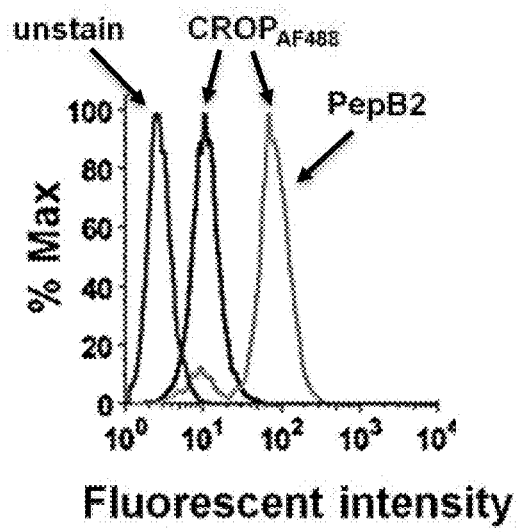
Figure 29C:
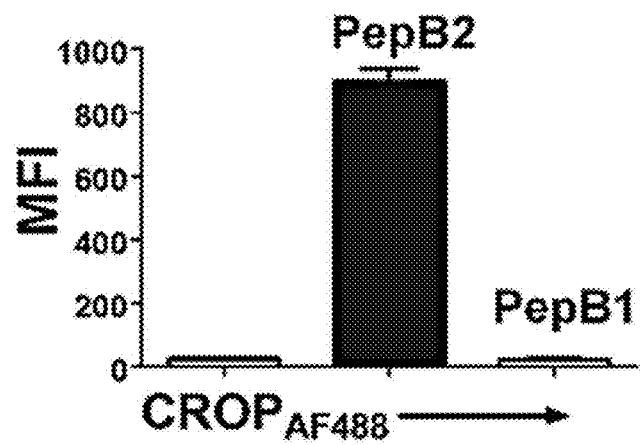
Figure 29D:
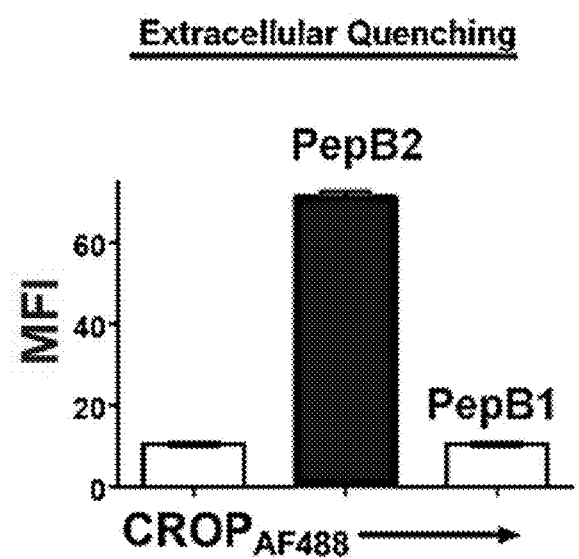
Figure 30A:
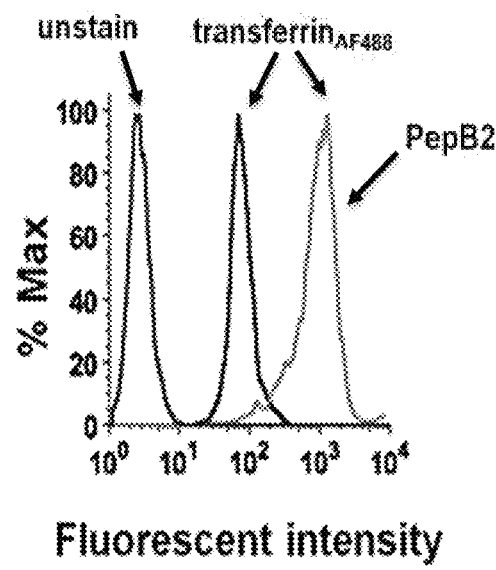
Figure 30B:
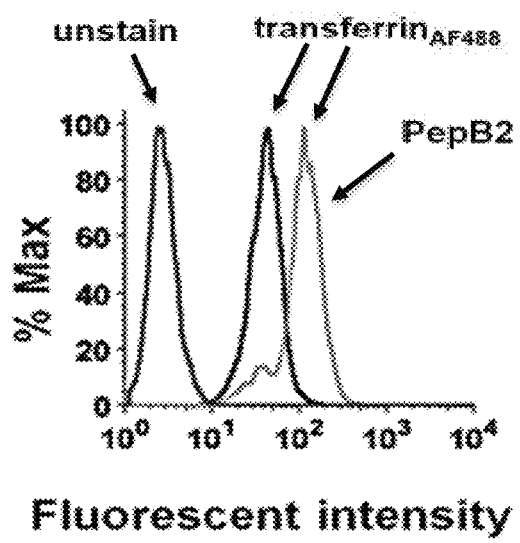
Figure 30C:
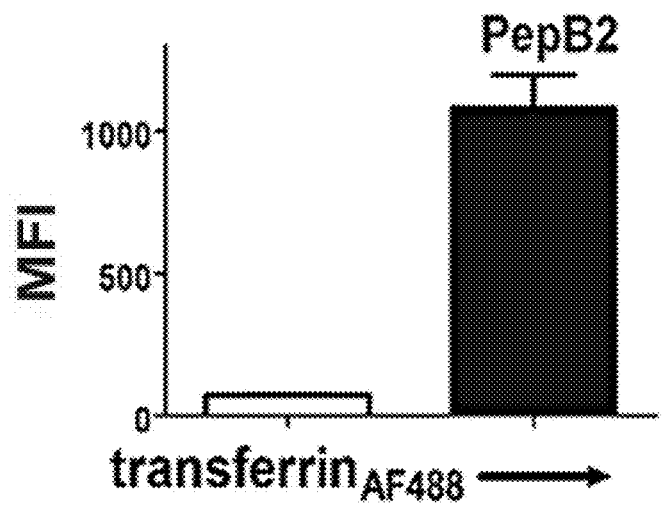
Figure 30D:
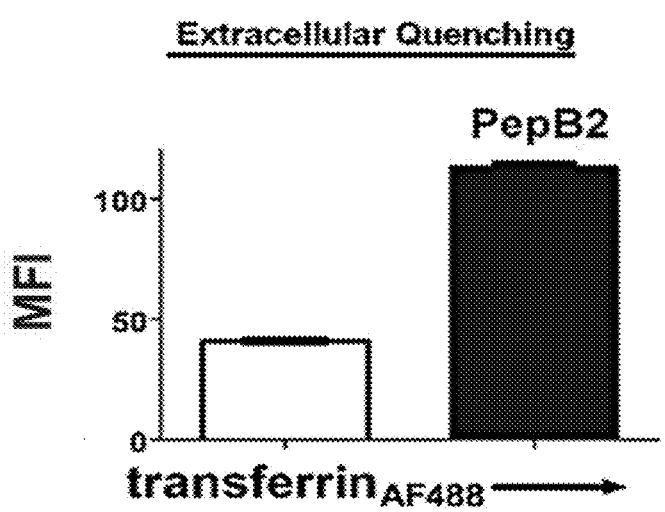
Figure 31A:
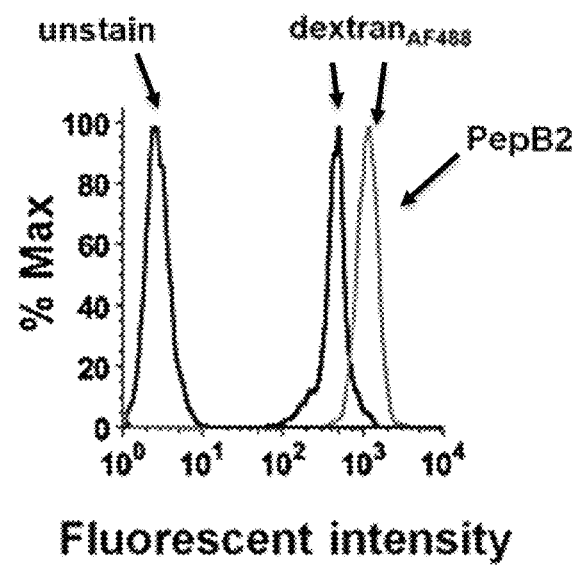
Figure 31B:
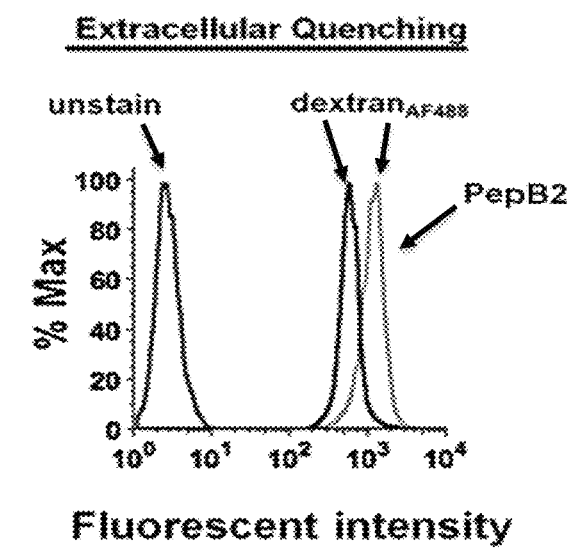
Figure 31C:
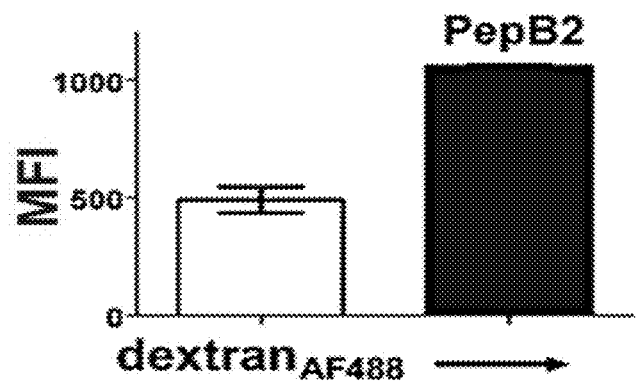
Figure 31D:
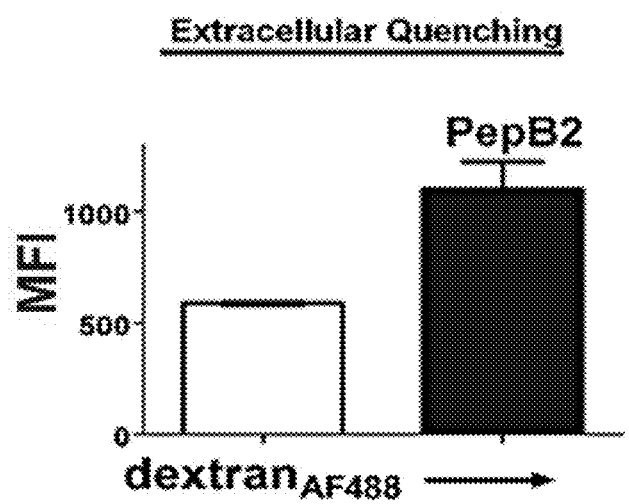
Figure 32A:
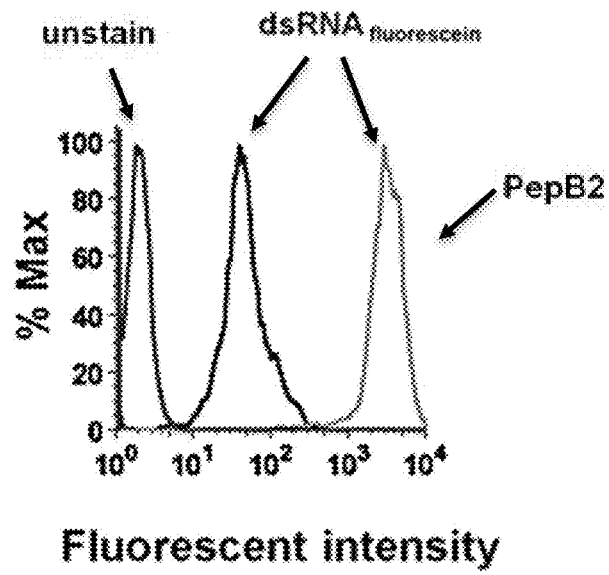
Figure 32B:
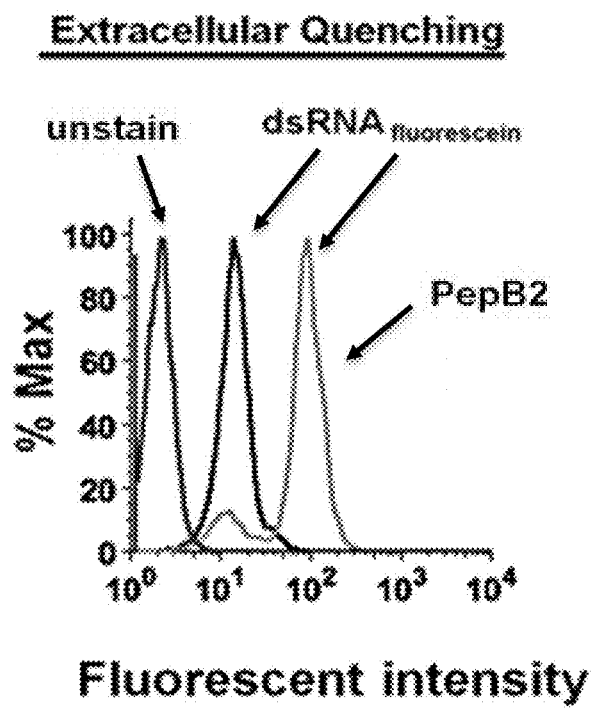
Figure 32C:
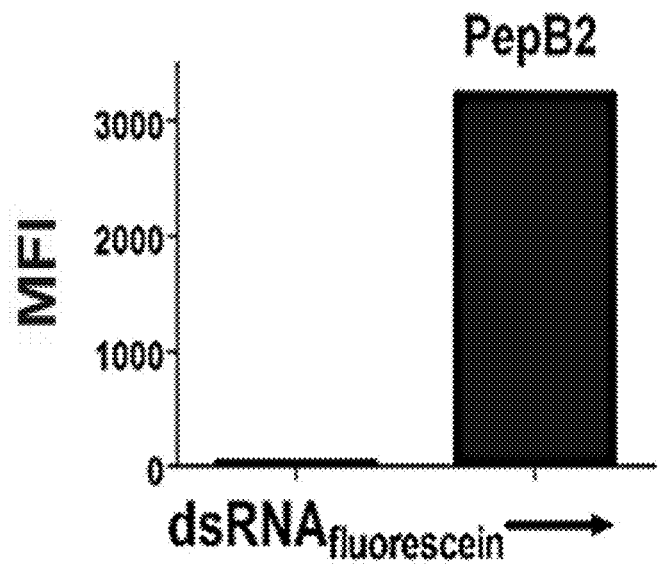
Figure 32D:
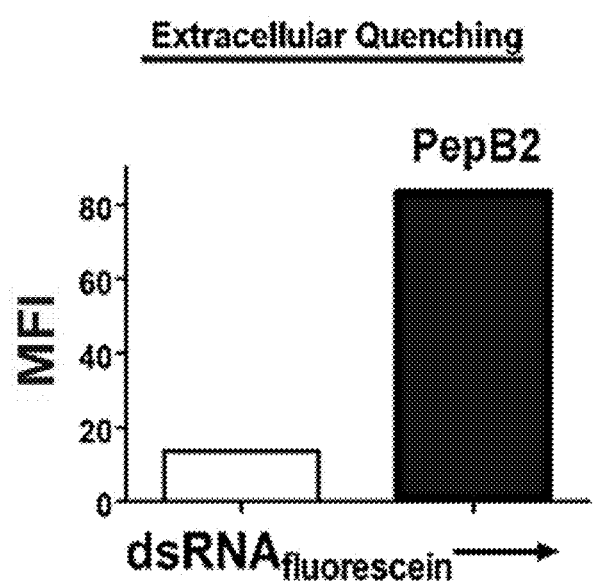
Figure 33A:
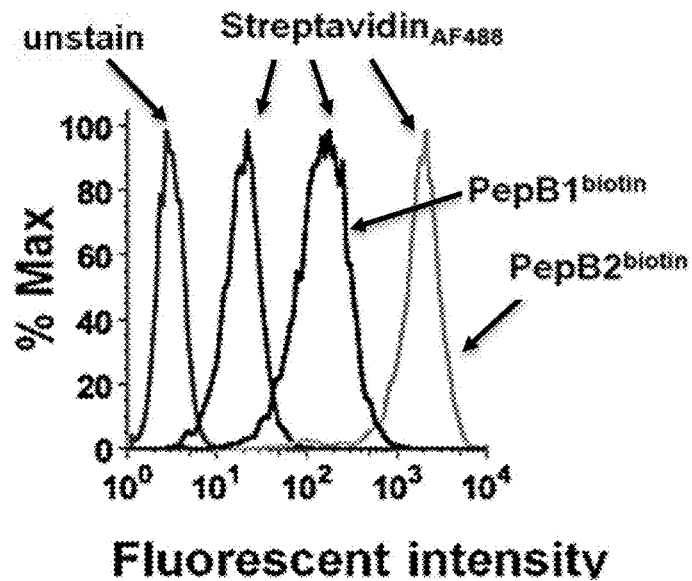
Figure 33B:
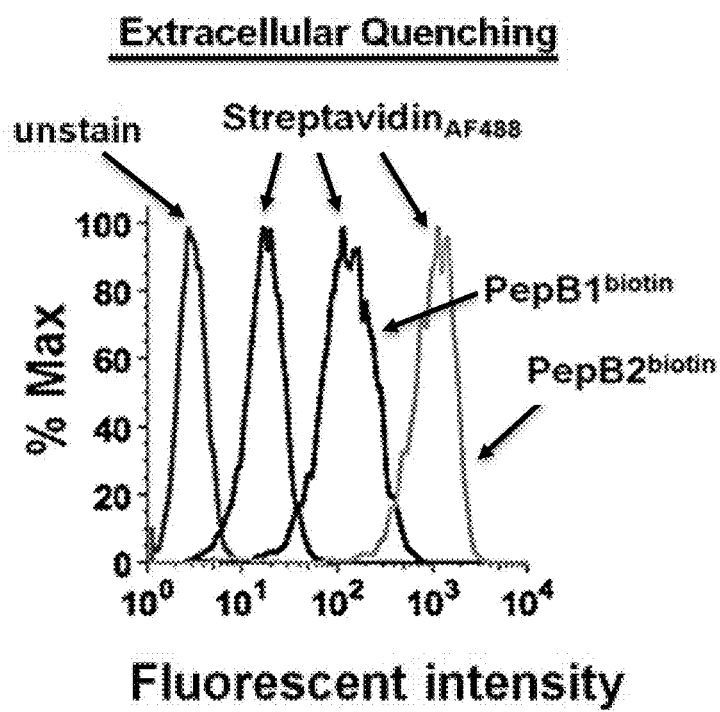
Figure 33C:
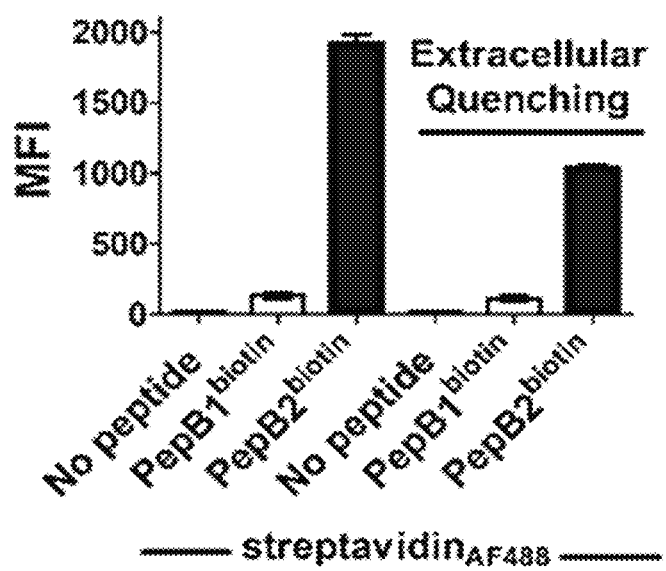
Figure 34:
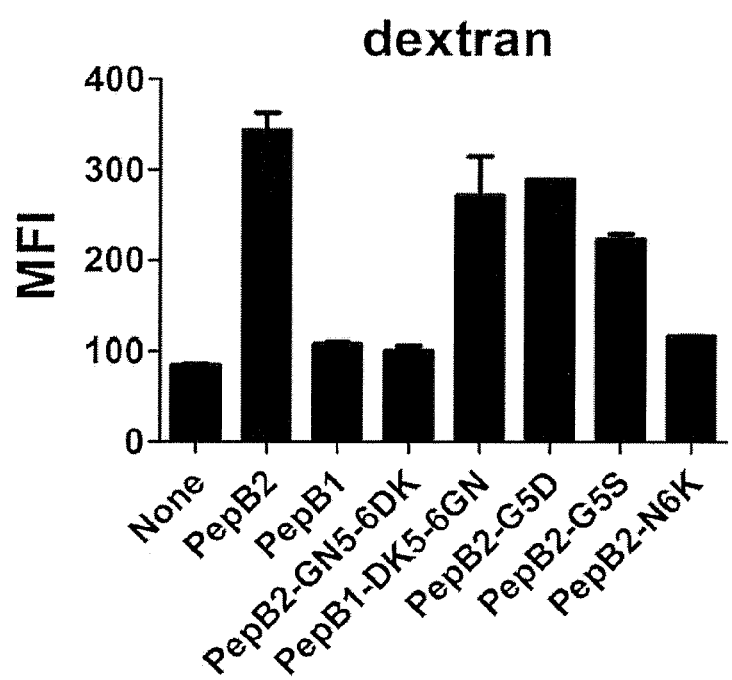
Figure 35:
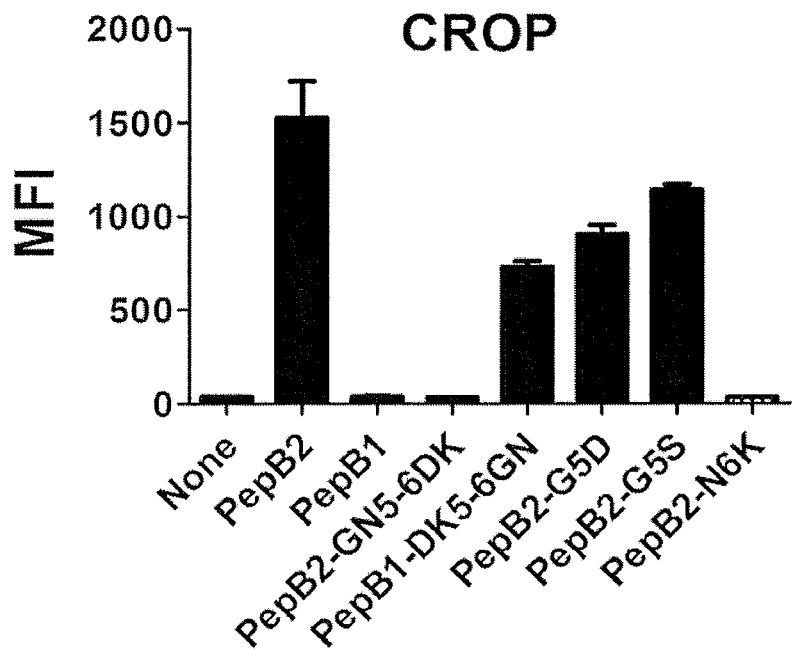
Figure 36:
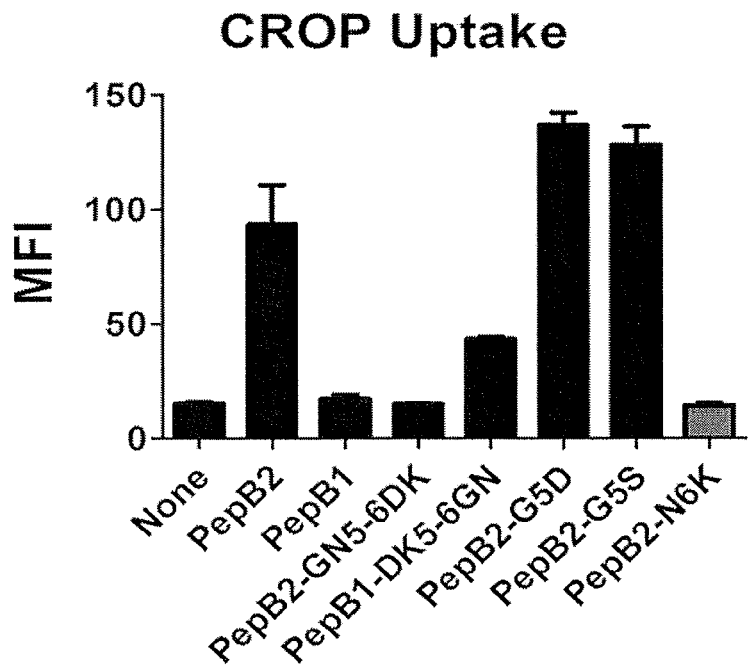
Figure 37:
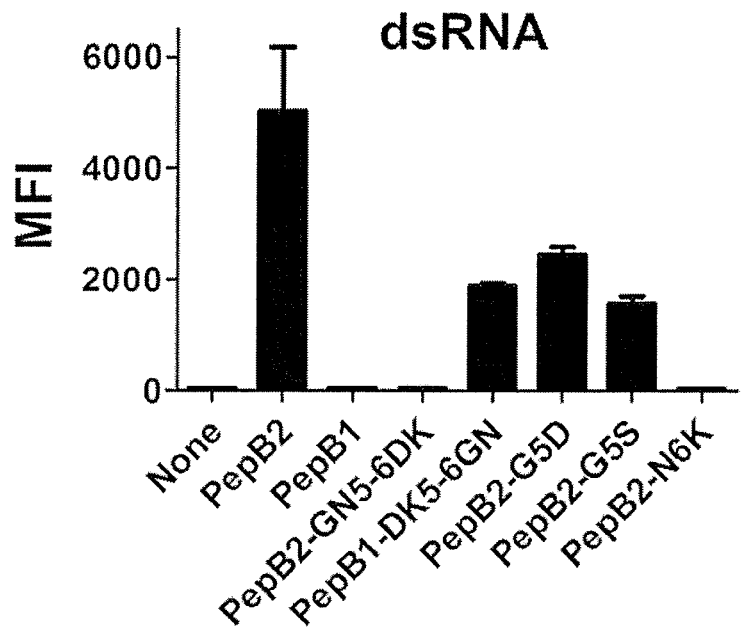
Figure 38:
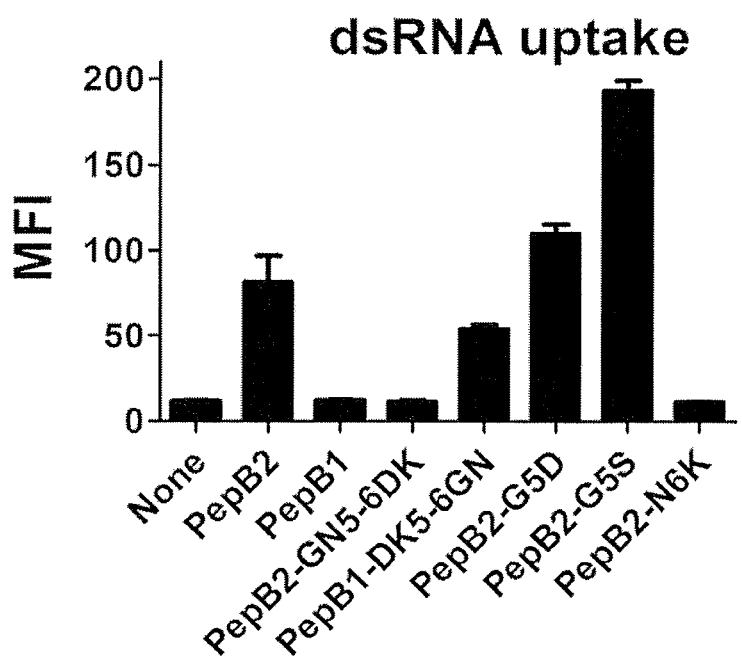

In another investigation, the PepB2 sequence (SEQ ID NO:6) was randomly scrambled 12 times which resulted in 10 different soluble peptides (Table 5). Anti-TcdB activity was examined in each of the 10 peptides and three (scramble peptide 8, scramble peptide 9, and scramble peptide 12) were found to have inhibitory activity (FIG. 27).

TABLE 5

Peptides obtained from randomly scrambling the amino acid sequence of PepB2.

| Peptide | Amino Acid Sequence | SEQ ID NO: |
| --- | --- | --- |
| PepB2 | NVFKGNTISDKISFNFSDK | 6 |
| Scramble 1 | SSKDKIVSFKNGFTFDINN | 31 |
| Scramble 3 | IKKSNVFNSFFDSINGKTD | 32 |
| Scramble 4 | FGNKFTSVDNSKIKFIDSN | 33 |
| Scramble 5 | IGVFSNDKKNINTSFDFSK | 34 |
| Scramble 6 | KFVFDDIKNSSISNKTFNG | 35 |
| Scramble 7 | GSSSIINDDFKNVTKNKFF | 36 |
| Scramble 8 | FKDNNSIIFDVKGTNFSSK | 37 |
| Scramble 9 | DKFSNSNKDKISFGNVTFI | 38 |
| Scramble 10 | NFNISVSKDFFSGKTNIDK | 39 |
| Scramble 12 | SNKNFSGIVFTNFDIDKSK | 40 |

While the initial work focused on positions 1753-1800 of TcdB2, further investigations were made into homologous regions of other large clostridia toxins (TcdB1, TcdA, TscL, and TpeL. Peptides generated from these toxins are shown in Table 6. Soluble peptides were examined for inhibitory activity against TcdB toxin.

TABLE 6

Toxin-derived peptides and anti-TcdB activity.

| Toxin | Location | Amino Acid Sequence | TcdB inhibitory activity? | SEQ ID NO: |
| --- | --- | --- | --- | --- |
| TcdB1 | 1752-1769 | MSTSEENKVSQVKIRFVN | NO | 41 |
| TcdB1 | 1761-1779 | SQVKIRFVMVFKDKTLANK | NO | 42 |
| TcdB1 | 1766-1782 | RFVNVFKDKTLANKLSF | NO | 43 |

TABLE 6-continued

Toxin-derived peptides and anti-TcdB activity.

| Toxin | Location | Amino Acid Sequence | TcdB inhibitory activity? | SEQ ID NO: |
|---|---|---|---|---|
| TcdB1 | 1769-1787 | NVFKDKTLANKLSFNFSDK | NO | 44 |
| TcdA | 1750-1766 | RYLEESNKKILQKIRIK | NO | 45 |
| TcdA | 1753-1774 | EESNKKILQKIRIKGILSNTQS | NO | 46 |
| TcdA | 1755-1774 | SNKKILQKIRIKGILSNTQS | NO | 47 |
| TcdA | 1766-1784 | KGILSNTQSFNKMSIDFKD | NO | 48 |
| TcdA | 1774-1795 | SFNKMSIDFKDIKKLSLGYIMS | YES | 49 |
| TcdA | 1789-1809 | SLGYIMSNFKSFNSENELDRD | NO | 50 |
| TcdA | 1795-1814 | SNFKSFNSENELDRDHLGFK | NO | 51 |
| TcdA | 1798-1817 | KFSNSENELDRDHLGFKIID | NO | 52 |
| TcdA | 1808-1827 | RDHLGFKIIDNKTYYYDEDS | NO | 53 |
| TscL | 1753-1770 | IANSEEDNQPQVKIRFVN | NO | 54 |
| TscL | 1762-1780 | PQVKIRFVNVFKSDTAADK | NO | 55 |
| TscL | 1767-1783 | RFVNVFKSDTAADKLSF | NO | 56 |
| TscL | 1770-1788 | NVFKSDTAADKLSFNFSDK | NO | 57 |
| TscL | 1783-1800 | FNFSDKQDVSVSKIISTF | NO | 58 |
| TpeL | 1710-1728 | KDFKWDIKGNDIILVRKKI | NO | 59 |
| TpeL | 1721-1739 | IILVRKKINGFNSTILLKD | NO | 60 |
| TpeL | 1726-1744 | KKINGFNSTILLKDTIDNN | NO | 61 |
| TpeL | 1738-1757 | KDTIDNNSYFNYVTLIFNDK | NO | 62 |

Only one of the peptides, TcdA 1774-1795, (SEQ ID NO: 49) was found to have inhibitory activity against TcdB toxin. TcdA 1752-1798 has only 28% identity with the homologous region (amino acid positions 1754-1800) of TcdB2. Dose-dependent inhibition of TcdB by TcdA 1774-1795 peptide is shown in FIG. 28. The CROPS region of TcdA (positions 1850-2701) was examined and was not inhibitory.

PepB2 Functions as a Cell Penetrating Peptide

In previous work we found that the 1753-1851 region of TcdB2 alters the exposure of proximal neutralizing epitopes in the carboxy-terminal domain (CTD) of the toxin. Because of this we hypothesized that PepB2, which is derived from this region of the toxin, alters the activity of the CTD (also known as the CROP region) of TcdB. To further explore this, a recombinant fragment of TcdB covering residues 1853-2366 and representing the CROP domain was fluorescently labeled and its interaction with cells was examined in the presence and absence of PepB2. As shown in FIGS. 29A-29D and similar to the results found with full length TcdB, PepB2 triggered increased overall interactions between $CROP_{AF488}$ and cells. However, in contrast to full-length TcdB, PepB2 increased the amount of $CROP_{AF488}$ that entered cells (FIGS. 29A-29D). In contrast, PepB1 did not display such an activity. This result suggested PepB2 might have characteristics similar to cell penetrating peptides (CPPs) that have been described in a variety of other systems and this led us to determine if PepB2 is itself a cell penetrating peptide. CPPs are small peptides, usually shorter than 30 amino acids, that can be used to drive DNA or protein into cells. Because of their potential biotechnology applications, a large number of CPPs are underdevelopment that utilize various mechanisms to penetrate into cells. We investigated the ability of PepB2 to deliver heterogenous molecules into cells. The cellular uptakes of transferrin, dextran, and double stranded RNA (dsRNA) were determined in the presence of PepB2. We detected a significant increase in cell entry of these molecules facilitated by PepB2 (FIGS. 30A-32D). Subsequently, we investigated if PepB2 could directly bind to and enter cells. A biotinylated form of PepB2 was loaded with fluorescent streptavidin and then applied to cells before analysis by flow cytometry and confocal microscopy. These results, shown in FIGS. 33A-33C, demonstrated that PepB2 is able to bind and carry streptavidin into cells. PepB1 was also found to bind and carry streptavidin into cells, but at a much lower level than that observed for PepB2.

Next, the mutant peptides listed in Table 2 were examined to determine which amino acids were relevant to the cell penetrating activities of PepB2. As shown in FIGS. 34-38, the replacement of $G_5N_6$ from PepB2 with $D_5K_6$ from PepB1 resulted in loss of cell penetrating activities. If the $D_5K_6$ sequence of PepB1 was replaced with $G_5N_6$ from PepB2 (PepB1-$DK_{5-6}$GN), cell penetrating activities were gained. If $G_5$ of PepB2 is converted to the $D_5$ residue from PepB1 (PepB2-G$_5$D), the cell penetrating activities remained intact. Cell penetrating activities also remained when G$_5$ of PepB2 was changed to an S residue (PepB2-G$_5$S). However, cell penetrating activities were reduced when N$_6$ was switched to the K$_6$ from PepB1 (PepB2-N$_6$K). It was found that PepB2-G$_5$S more efficiently transports dsRNA into cells than PepB2 but this is not the case for dextran delivery.

Penetratin Inhibits the Cytotoxicity of TcdB

Figure 39:
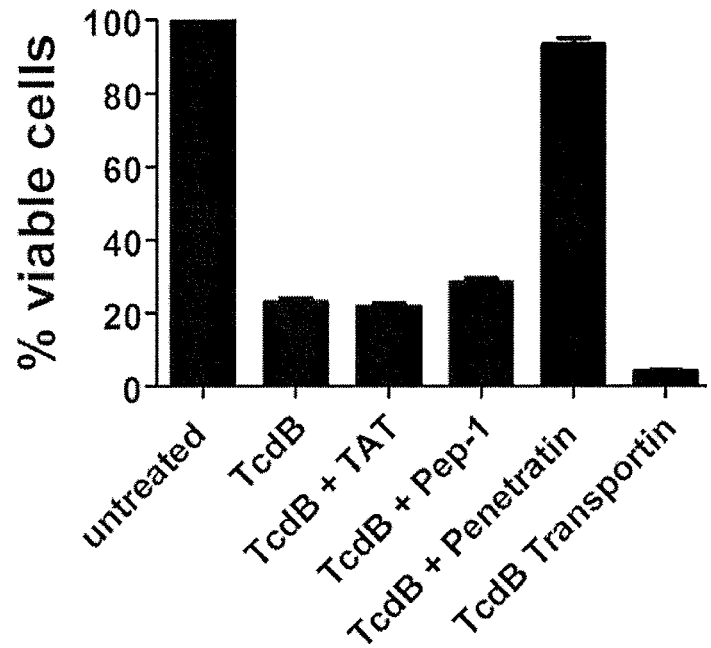
Figure 40:
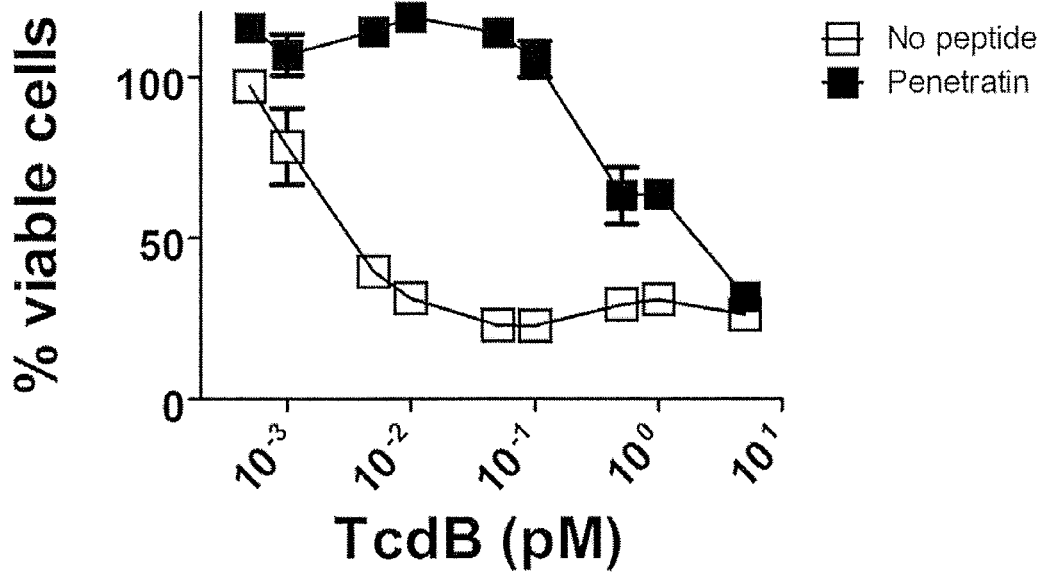

The effects of other, known, CPPs on the cytotoxicity of TcdB was investigated. Three well-studied CPPs, TAT (GRKKRRQRRRPPQ SEQ ID NO:63), Pep-1 (KETWWETWWTEWSQPKKKRKV—(SEQ ID NO: 64), Transportan (AGYLLGKINLKALAALAKKIL—SEQ ID NO:65), and Penetratin (RQIKIWFQNRRMKWKK—SEQ ID NO:66) were examined for this purpose. Penetratin is a 16 amino acid peptide derived from the homeodomain of Antennapedia, a transcription factor from *Drosophila*. Surprisingly, we found that, like PepB2, Penetratin also blocked cellular intoxication by TcdB while TAT, Pep-1, and transportan 10 did not appear to alter TcdB cytotoxicity (FIGS. 39-41).

The findings in the present disclosure indicate that certain epitopes of intracellular toxins can be effective as anti-toxins when provided as individual peptide molecules. Previous studies by others have identified toxin-inhibitory peptides through library screens; however, the concept of using peptides derived from the toxin itself is previously unknown. In addition to its inhibitory activity on TcdB toxins, PepB2 and variants thereof described herein also exhibit cell penetrating activity and have the ability to deliver heterogenous cargo into cells. Though the mechanisms of toxin cell entry have been studied for many years, PepB2 is the first reported example of a toxin-derived peptide with the ability to deliver unrelated molecules into cells.

While the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the inventive concepts of the present disclosure, it being understood that the particulars shown are by way of example and for purposes of illustrative discussion of particular embodiments only and are presented in the cause of providing what is believed to be the most useful and readily understood description of procedures as well as of the principles and conceptual aspects of the present disclosure. Changes may be made in the formulation of the various compositions described herein, the methods described herein or in the steps or the sequence of steps of the methods described herein without departing from the spirit and scope of the present disclosure. Further, while various embodiments of the present disclosure have been described in claims herein below, it is not intended that the present disclosure be limited to these particular claims. Applicants reserve the right to amend, add to, or replace the claims indicated herein below in subsequent patent applications.

What is claimed is:

1. A pharmaceutical composition, comprising:
a peptide disposed in a pharmaceutically-acceptable carrier or vehicle, the peptide comprising an amino acid sequence $X_1 X_2 X_3 X_4 X_5 X_6 X_7 X_8 X_9 X_{10} X_{11}$ (SEQ ID NO:67), wherein
each of $X_1$, $X_2$, $X_3$, $X_4$, $X_7$, $X_8$, $X_9$, $X_{10}$, and $X_{11}$ is independently selected from the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val;
$X_5$ is selected from gly, L-ala, L-ser, D-ala, and D-ser;
$X_6$ is selected from L-asn, L-asp, L-gln, L-his, L-ser, L-thr, D-asn, D-asp, D-gln, D-his, D-ser, and D-thr; and
wherein the amino acid sequence SEQ ID NO:67 has at least 90% identity with SEQ ID NO:1, has a length of from 15 to 100 amino acids, and has anti-*Clostridium difficile* toxin B activity and/or has cell penetrating activity.

2. The pharmaceutical composition of claim 1, wherein $X_3$ is selected from the group consisting of L-phe, L-met, L-leu, L-ile, D-phe, D-met, d-leu, and D-ile.

3. The pharmaceutical composition of claim 1, wherein $X_5$ is gly, and $X_6$ is D-asn or L-asn.

4. The pharmaceutical composition of claim 1, wherein positions $X_5$ and $X_6$ comprise at least a portion of a beta-turn motif.

5. The pharmaceutical composition of claim 1, wherein the peptide is linked to a carrier protein or polymer molecule.

6. The pharmaceutical composition of claim 1, comprising a formulation for extended release of the peptide.

7. A pharmaceutical composition, comprising:
a peptide disposed in a pharmaceutically-acceptable carrier or vehicle, the peptide comprising an amino acid sequence:
$X_1 X_2 X_3 X_4 X_5 X_6 X_7 X_8 X_9 X_{10} X_{11} X_{12} X_{13} X_{14} X_{15} X_{16} X_{17} X_{18} X_{19}$ (SEQ ID NO:68), wherein
each of $X_1$, $X_2$, $X_3$, $X_4$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, and $X_{19}$ is independently selected from the group consisting of gly, L-ala, L-arg, L-asn, L-asp, L-cys, L-glu, L-gln, L-his, L-ile, L-leu, L-lys, L-met, L-phe, L-pro, L-ser, L-Thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val;
$X_5$ is selected from gly, L-ala, and D-ala; and
$X_6$ is selected from L-asn, L-gln, L-his, D-asn, D-gln, and D-his; and
wherein the peptide has at least 89% identity with SEQ ID NO:6, has a length of from 15 to 100 amino acids and has inhibitory activity against *Clostridium difficile* toxin B toxins and/or cell penetrating activity.

8. The pharmaceutical composition of claim 7, wherein $X_3$ is selected from the group consisting of L-phe, L-met, L-leu, L-ile, D-phe, D-met, d-leu, and D-ile.

9. The pharmaceutical composition of claim 7, wherein $X_5$ is gly, and $X_6$ is D-asn or L-asn.

10. The pharmaceutical composition of claim 7, wherein the amino acid sequence SEQ ID NO:68 has at least 94% identity with SEQ ID NO:6.

11. The pharmaceutical composition of claim 7, wherein positions $X_5$ and $X_6$ comprise at least a portion of a beta-turn motif.

12. The pharmaceutical composition of claim 7, wherein the peptide is linked to a carrier protein or polymer molecule.

13. The pharmaceutical composition of claim 7, comprising a formulation for extended release of the peptide.

14. A method of treating a *Clostridium difficile* infection in a subject in need of such treatment, comprising:
administering to the subject an effective amount of a pharmaceutical composition of claim 1 comprising at least one of:
(1) a peptide disposed in a pharmaceutically-acceptable carrier or vehicle, the peptide comprising an amino acid sequence $X_1$ $X_2$ $X_3$ $X_4$ $X_5$ $X_6$ $X_7$ $X_8$ $X_9$ $X_{10}$ $X_{11}$ (SEQ ID NO:67), wherein
each of $X_1$, $X_2$, $X_3$, $X_4$, $X_7$, $X_8$, $X_9$, $X_{10}$, and $X_{11}$ is independently selected from the group consisting of gly, L-ala, L-arg, L-asn, L-asp, L-cys, L-glu, L-gln, L-his, L-ile, L-leu, L-lys, L-met, L-phe, L-pro, L-ser, L-thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val;
$X_5$ is selected from gly, L-ala, L-ser, D-ala, and D-ser;
$X_6$ is selected from L-asn, L-asp, L-gln, L-his, L-ser, L-thr, D-asn, D-asp, D-gln, D-his, D-ser, and D-thr; and
wherein the amino acid sequence SEQ ID NO:67 has at least 90% identity with SEQ ID NO:1, has a length of from 15 to 100 amino acids, and has anti-*Clostridium difficile* toxin B activity and/or has cell penetrating activity; and
(2) a peptide disposed in a pharmaceutically-acceptable carrier or vehicle, the peptide comprising an amino acid sequence:
$X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $X_{17}$ $X_{18}$ $X_{19}$ (SEQ ID NO:68), wherein
each of $X_1$, $X_2$, $X_3$, $X_4$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$ and $X_{19}$ is independently selected from the group consisting of gly, L-ala, L-arg, L-asn, L-asp, L-cys, L-glu, L-gln, L-his, L-ile, L-leu, L-lys, L-met, L-phe, L-pro, L-ser, L-Thr, L-trp, L-tyr, L-val, D-ala, D-arg, D-asn, D-asp, D-cys, D-glu, D-gln, D-his, D-ile, D-leu, D-lys, D-met, D-phe, D-pro, D-ser, D-thr, D-trp, D-tyr, and D-val;
$X_5$ is selected from gly, L-ala, and D-ala; and
$X_6$ is selected from L-asn, L-gln, L-his, D-asn, D-gln, and D-his; and
wherein the peptide has at least 89% identity with SEQ ID NO:6, has a length of from 15 to 100 amino acids and has inhibitory activity against *Clostridium difficile* toxin B toxins and/or cell penetrating activity.

15. A method of treating a *Clostridium difficile* infection in a subject in need of such treatment, comprising:
administering to the subject an effective amount of a pharmaceutical composition comprising
a peptide disposed in a pharmaceutically-acceptable carrier or vehicle, the peptide comprising the amino acid sequence:
$X_1$, $X_2$, $X_3$, $X_4$, $X_5$, $X_6$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, $X_{19}$ (SEQ ID NO:68), wherein
each of $X_1$, $X_2$, $X_3$, $X_4$, $X_7$, $X_8$, $X_9$, $X_{10}$, $X_{11}$, $X_{12}$, $X_{13}$, $X_{14}$, $X_{15}$, $X_{16}$, $X_{17}$, $X_{18}$, and $X_{19}$ is independently selected from the group consisting of gly, L-ala, L-arg, L-asn, L-asp, L-cys, L-glu, L-gln, L-his, L-ile, L-leu, L-lys, L-met, L-phe, L-pro, L-ser, L-Thr, L-trp, L-tyr, L-val, D-ala, D-arg, D-san, D-sap, D-cys, D-glu, D-gln, D-his, D-ile, D-leu, D-lys, D-met, D-phe, D-pro, D-ser, D-thr, D-trp, D-tyr, and D-val;
$X_5$ is selected from gly, L-ala, and D-ala; and
$X_6$ is selected from L-asn, L-gln, L-his, D-asn, D-gln, and D-his; and
wherein the peptide has at least 89% identity with SEQ ID NO:6, has a length of from 15 to 100 amino acids and has inhibitory activity against *Clostridium difficile* toxin B toxins and/or cell penetrating activity.

16. The method of claim 15, wherein $X_3$ of SEQ ID NO:68 is selected from the group consisting of L-phe, L-met, L-leu, L-ile, D-phe, D-met, d-leu, and D-ile.

17. The method of claim 15, wherein $X_5$ of SEQ ID NO:68 is gly, and $X_6$ of SEQ ID NO:68 is D-asn or L-asn.

18. The method of claim 15, wherein the amino acid sequence SEQ ID NO:68 has at least 94% identity with SEQ ID NO:6.

19. The method of claim 15, wherein positions $X_5$ and $X_6$ of SEQ ID NO:68 comprise at least a portion of a beta-turn motif.

20. The method of claim 15, wherein the peptide of the pharmaceutical composition is linked to a carrier protein of polymer molecule.

21. The method of claim 15, wherein the pharmaceutical composition comprises a formulation for extended release of the peptide.

* * * * *